(12) United States Patent
Mulder et al.

(10) Patent No.: US 12,377,054 B2
(45) Date of Patent: Aug. 5, 2025

(54) TARGETING THE INNATE IMMUNE SYSTEM TO INDUCE LONG-TERM TOLERANCE AND TO RESOLVE MACROPHAGE ACCUMULATION IN ATHEROSCLEROSIS

(71) Applicant: Icahn School of Medicine at Mount Sinai, New York, NY (US)

(72) Inventors: Willem Mulder, Eindhoven (NL); Jordi Ochando, New York, NY (US); Zahi Fayad, Larchmont, NY (US); Mounia Braza, New York, NY (US); Raphaël Duivenvoorden, Gelderland (NL); Francois Fay, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 18/121,527

(22) Filed: Mar. 14, 2023

(65) Prior Publication Data

US 2023/0218537 A1 Jul. 13, 2023

Related U.S. Application Data

(62) Division of application No. 16/097,013, filed as application No. PCT/US2017/030444 on May 1, 2017, now abandoned.

(60) Provisional application No. 62/329,676, filed on Apr. 29, 2016.

(51) Int. Cl.
| | |
|---|---|
| *A61K 9/51* | (2006.01) |
| *A61K 9/00* | (2006.01) |
| *A61K 31/436* | (2006.01) |
| *A61K 38/13* | (2006.01) |
| *A61K 45/06* | (2006.01) |
| *A61K 51/12* | (2006.01) |
| *A61P 37/06* | (2006.01) |

(52) U.S. Cl.
CPC .......... *A61K 9/5169* (2013.01); *A61K 9/0019* (2013.01); *A61K 9/5123* (2013.01); *A61K 31/436* (2013.01); *A61K 38/13* (2013.01); *A61K 45/06* (2013.01); *A61K 51/1224* (2013.01); *A61P 37/06* (2018.01)

(58) Field of Classification Search
CPC .. A61K 9/5169; A61K 9/0019; A61K 9/5123; A61K 31/436; A61K 38/13; A61K 45/06; A61K 51/1224; A61K 9/1275; A61P 37/06
See application file for complete search history.

(56) References Cited

U.S. PATENT DOCUMENTS

| | | |
|---|---|---|
| 4,406,890 A | 9/1983 | Tarcsay et al. |
| 4,640,911 A | 2/1987 | Baschang |
| 5,349,060 A | 9/1994 | Kao et al. |
| 5,540,931 A | 7/1996 | Hewitt et al. |
| 5,543,158 A | 8/1996 | Gref et al. |
| 5,552,157 A | 9/1996 | Yaai et al. |
| 5,565,213 A | 10/1996 | Nakamori et al. |
| 5,567,434 A | 10/1996 | Szoka, Jr. |
| 5,665,772 A | 9/1997 | Cottens et al. |
| 5,738,868 A | 4/1998 | Shinkarenko |
| 5,741,516 A | 4/1998 | Webb et al. |
| 5,795,587 A | 8/1998 | Gao et al. |
| 5,985,890 A | 11/1999 | Cottens et al. |
| 6,200,985 B1 | 3/2001 | Cottens et al. |
| 6,440,990 B1 | 8/2002 | Cottens et al. |
| 7,488,802 B2 | 2/2009 | Collins et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,563,603 B2 | 10/2013 | Chavez |
| 8,865,644 B2 | 10/2014 | Cho |
| 9,408,829 B2 | 8/2016 | Lutgens et al. |
| 10,485,884 B2 | 11/2019 | Sahin et al. |
| 10,525,152 B2 | 1/2020 | Sigalov |
| 11,859,021 B2 | 1/2024 | Janssen et al. |
| 2002/0086049 A1 | 7/2002 | Bolton et al. |
| 2005/0182243 A1 | 8/2005 | Sligar et al. |
| 2005/0234234 A1 | 10/2005 | Gu et al. |
| 2005/0287636 A1 | 12/2005 | Cho |
| 2006/0002852 A1 | 1/2006 | Saltzman et al. |
| 2006/0222652 A1 | 10/2006 | Sebbel et al. |
| 2006/0251677 A1 | 11/2006 | Bachmann et al. |
| 2008/0145441 A1 | 6/2008 | Penades et al. |
| 2009/0028910 A1 | 1/2009 | DeSimone et al. |
| 2009/0226525 A1 | 9/2009 | Rios et al. |

(Continued)

FOREIGN PATENT DOCUMENTS

| | | |
|---|---|---|
| CN | 101096386 | 1/2008 |
| CN | 101888780 | 11/2010 |

(Continued)

OTHER PUBLICATIONS

Kim et al., ACS Nano, vol. 7, No. 11, 9975-9983 (2013) (Year: 2013).*

(Continued)

*Primary Examiner* — Robert S Cabral
(74) *Attorney, Agent, or Firm* — Fish & Richardson P.C.

(57) ABSTRACT

Methods and compositions for inducing long-term tolerance by hybrid nanoparticles are provided. Compositions and formulations comprising hybrid nanoparticles with inherent affinity for innate immune cells are provided.

18 Claims, 49 Drawing Sheets

(56) References Cited

U.S. PATENT DOCUMENTS

| | | |
|---|---|---|
| 2011/0237435 A1 | 9/2011 | Ryan |
| 2011/0256224 A1 | 10/2011 | Sigalov |
| 2013/0045161 A1 | 2/2013 | Sigalov |
| 2013/0252879 A1* | 9/2013 | Cho .................... A61K 31/439 514/1.9 |
| 2015/0182461 A1 | 7/2015 | Kim et al. |
| 2016/0317647 A1 | 11/2016 | Ciaramella et al. |
| 2018/0250419 A1 | 9/2018 | Schwendeman et al. |
| 2018/0263907 A1 | 9/2018 | Hefesha et al. |
| 2019/0008918 A1 | 1/2019 | Upmanyu et al. |
| 2019/0153443 A1 | 5/2019 | Fitzgerald et al. |
| 2019/0290593 A1 | 9/2019 | Mulder et al. |
| 2020/0253884 A1 | 8/2020 | Mulder et al. |
| 2020/0261591 A1 | 8/2020 | Mulder et al. |
| 2020/0376102 A1 | 12/2020 | Mulder et al. |
| 2020/0376146 A1 | 12/2020 | Mulder et al. |
| 2022/0332762 A1 | 10/2022 | Janssen et al. |
| 2023/0355537 A1 | 11/2023 | Mulder et al. |
| 2024/0190921 A1 | 6/2024 | Janssen et al. |

FOREIGN PATENT DOCUMENTS

| | | |
|---|---|---|
| CN | 101903018 | 12/2010 |
| CN | 102027019 | 4/2011 |
| CN | 102178954 | 9/2011 |
| CN | 102264364 A | 11/2011 |
| CN | 103118691 | 5/2013 |
| CN | 103354749 | 10/2013 |
| CN | 103533934 | 1/2014 |
| CN | 103589699 A | 2/2014 |
| CN | 105828834 | 8/2016 |
| CN | 106714836 | 5/2017 |
| CN | 106831614 A | 6/2017 |
| CN | 111971028 A | 11/2020 |
| EP | 0003833 | 9/1979 |
| EP | 0021367 | 1/1981 |
| EP | 0025495 | 3/1981 |
| EP | 0102319 | 3/1984 |
| EP | 0163286 | 12/1985 |
| EP | 0173960 | 3/1986 |
| EP | 0192609 | 8/1986 |
| EP | 0192611 | 8/1986 |
| JP | 55-28933 | 2/1980 |
| JP | 58-172399 | 10/1983 |
| JP | 2007532134 | 11/2007 |
| KR | 10-2198900 B1 | 1/2021 |
| WO | WO 1993/010148 | 5/1993 |
| WO | WO 1994/009010 | 4/1994 |
| WO | WO 1995/010293 | 4/1995 |
| WO | WO 1995/016691 | 6/1995 |
| WO | WO 1996/001645 | 1/1996 |
| WO | WO 1996/009063 | 3/1996 |
| WO | WO 1996/041807 | 12/1996 |
| WO | WO 1998/009989 | 3/1998 |
| WO | WO 2003/042402 | 5/2003 |
| WO | WO 2006/053430 | 5/2006 |
| WO | WO 2007/022474 | 2/2007 |
| WO | WO 2008/156712 | 12/2008 |
| WO | WO 2009/051837 | 4/2009 |
| WO | WO 2009/106999 | 9/2009 |
| WO | WO 2010/036959 | 4/2010 |
| WO | WO 2010/047839 | 4/2010 |
| WO | WO 2010/089411 | 8/2010 |
| WO | WO 2011/066342 | 6/2011 |
| WO | WO 2011/082400 | 7/2011 |
| WO | WO 2011/159877 | 12/2011 |
| WO | WO 2011/161699 | 12/2011 |
| WO | WO 2015/079411 | 6/2015 |
| WO | WO 2016/019333 | 2/2016 |
| WO | WO 2016/138286 | 9/2016 |
| WO | WO 2016/154544 | 9/2016 |
| WO | WO 2016/172146 | 10/2016 |
| WO | WO 2016/172615 A1 | 10/2016 |
| WO | WO 2017/011685 | 1/2017 |
| WO | WO 2017/024312 | 2/2017 |
| WO | WO-2017106690 A1 * | 6/2017 | ............ A61K 33/00 |
| WO | WO 2017/190145 | 11/2017 |
| WO | WO 2017/205536 A2 | 11/2017 |
| WO | WO 2018/071549 | 4/2018 |
| WO | WO 2018/187515 | 10/2018 |
| WO | WO 2019/103998 | 5/2019 |
| WO | WO 2023/192956 | 10/2023 |

OTHER PUBLICATIONS

Office Action in European Appln. No. 22155443.9, mailed on Aug. 28, 2023, 6 pages.

Costello et al., "A Review of the current status and concept of the emerging implications of zinc and zinc transporters in the development of pancreatic cancer," Pancreatic disorders & therapy, Jan. 2013, 19 pages.

Wang et al., "Tumor cell-intrinsic PD-1 receptor is a tumor suppressor and mediates resistance to PD-1 blockade therapy," PNAS, Mar. 24, 2020, 117(12):6640-6650.

International Preliminary Report on Patentability in International Appln. No. PCT/US2023/065166, mailed on Oct. 10, 2024, 10 pages.

Invitation to Pay Additional Fees in International Appln. No. PCT/US2023/065166, mailed on Jul. 14, 2023, 2 pages.

Office Action in Australian Appln. No. 2018370828, mailed on Nov. 8, 2023, 5 pages.

Office Action in Australian Appln. No. 2022204675, dated Aug. 19, 2024, 4 pages.

Office Action in Japanese Appln. No. 2023-060872, mailed on Apr. 16, 2024, 5 pages (with English translation).

Office Action in Japanese Appln. No. 2023-130072, mailed on Sep. 10, 2024, 9 pages (with English translation).

Office Action in Japanese Appln. No. 2023-163975, mailed on Aug. 6, 2024, 4 pages (with English translation).

Cecil Textbook of Medicine, 20th Edition, Bennett et al. (ed), vol. 1, Edition, vol. 1, 1996, pp. 1004-1010.

Gura et al., "Systems for Identifying New Drugs Are Often Faulty," Science, Nov. 7, 1997, 278:1041-1042.

Johnson et al., "Relationships between drug activity in NCI preclinical in vitro and in vivo models and early clinical trials," British Journal of Cancer, 2001, 84:1424-1431.

Office Action in Colombian Appln. No. 202302783, mailed on Dec. 12, 2024, 28 pages (with Machine translation).

Office Action in Japanese Appln. No. 2023-060872, mailed on Jan. 7, 2025, 6 pages (with English translation).

Office Action in Chinese Appln. No. 202410398398.2, mailed on Nov. 26, 2024, 11 pages (with English translation).

Office Action in Colombian Appln. No. NC2023/0013700, mailed on Nov. 5, 2024, 18 pages (with Machine translation).

Sun, "The Synthesis of Novel Carbonylthiourea, Amide, Imidazo-[2, 1-b]-1, 3, 4-thiadiazole Containing Pyrazole Ring," Master's e-Journal, Engineering Science and Technology I, 2009, Issue 2, 7 pages (with English abstract).

U.S. Appl. No. 16/097,013, filed Oct. 26, 2018, Willem J. M. Mulder.

U.S. Appl. No. 16/862,564, filed Apr. 30, 2020, Willem J. M. Mulder.

U.S. Appl. No. 16/862,570, filed Apr. 30, 2020, Willem J. M. Mulder.

U.S. Appl. No. 17/743,342, filed May 12, 2022, Willem J. M. Mulder.

U.S. Appl. No. 18/076,759, filed Dec. 7, 2022, Willem J. M. Mulder.

U.S. Appl. No. 18/927,572, filed Oct. 25, 2024, Willem J. M. Mulder.

U.S. Appl. No. 16/863,333, filed Apr. 30, 2020, Willem J. M. Mulder.

U.S. Appl. No. 16/863,438, filed Apr. 30, 2020, Willem J. M. Mulder.

U.S. Appl. No. 18/806,189, filed Aug. 15, 2024, Willem J. M. Mulder.

U.S. Appl. No. 17/698,971 (U.S. Pat. No. 11,859,021), filed Mar. 18, 2022 (Jan. 2, 2024), Henricus Marie Janssen.

(56) References Cited

OTHER PUBLICATIONS

U.S. Appl. No. 18/510,323, filed Nov. 15, 2023, Henricus Marie Janssen.
U.S. Appl. No. 18/850,960, filed Sep. 25, 2024, Abraham J. Teunissen.
[No. Author], "Highlights of Prescribing Information - RAPAMUNE (sirolimus) oral solution; RAPAMUNE (sirolimus) tablets, for oral use," Distributed by Wyeth Pharmaceuticals Inc., Pfizer, revised on Apr. 2017, 56 pages.
[No Author], Rationale of Drug Design, 1st Ed., China Campeering, Chinese Pharmaceutical Science Press, Apr. 1990, pp. 199-200 (Relevance Explained in Chinese Office Action in Chinese Patent Application No. 201880086231.5, dated Nov. 3, 2022).
Adamczyk et al., "Lipase Mediated Hydrolysis of Rapamycin 42-Hemisuccinate Benzyl and Methyl Esters," Tetrahedron Letters, 1994, 35(7); 1019-1022.
Ahmed et al., "Immunological memory and protective immunity: understanding their relation," Science, 1996, 272(5258):54-60.
Ahonen et al., "The CD40-TRAF6 axis controls affinity maturation and the generation of long-lived plasma cells," Nat. Immunol., May 2002, 3(5):451-456.
Anders et al., "HTSeq—a Python framework to work with high-throughput sequencing data," Sep. 25, 2014, 31(2):166-169.
Andre et al., "CD40L stabilizes arterial thrombi by a β3 integrin-dependent mechanism," Nature, Mar. 2002, 8(3):247-252.
Arnold et al., "Inflammatory monocytes recruited after skeletal muscle injury switch into antiinflammatory macrophages to support myogenesis," The Journal of Experimental Medicine, 2007, 204(5):1057-1069.
Assanga et al., "Cell growth curves for different cell lines and their relationship with biological activities," Int. J. Biotechnol. Mol. Biol. Res., Aug. 2013, 4(4):60-70.
Auchincloss, "No. tolerance for depletion," Nature Medicine, 2004, 10:21-23.
Back et al., "Anti-inflammatory therapies for atherosclerosis," Nature Reviews Cardiology, Feb. 10, 2015, 12:199-211.
Bayle et al., "Rapamycin analogs with differential binding specificity permit orthogonal control of protein activity," Chemistry & Biology, Jan. 2006, 13(1):99-107.
Bekkering et al., "In Vitro Experimental Model of Trained Innate Immunity in Human Primary Monocytes," Clinical and Vaccine Immunology, Dec. 2016, 23(12):926-933.
Benichou et al., "Innate immunity and resistance to tolerogenesis in allotransplantation," Frontiers in Immunology, 2012, 3:73.
Berge et al., "Pharmaceutical Salts," Journal of Pharmaceutical Sciences, Jan. 1977, 66(1):1-19.
Boussiotis et al., "Molecular and Biochemical Aspects of the PD-1 Checkpoint Pathway," New England Journal of Medicine, 2016, 375:1767-1778.
Braza et al., "Inhibiting Inflammation with Myeloid Cell-Specific Nanobiologics Promotes Organ Transplant Acceptance," Immunity, 2018, 49, 819-828.
Bregoli et al., "Nanomedicine applied to translational oncology: A future perspective on cancer treatment," Nanomedicine: Nanotechnology, Biology and Medicine, 2016, 12(1):81-103.
Bricarello et al., "Reconstituted lipoprotein: a versatile class of biologically-inspired nanostructures," ACS Nano, 2011, 5:42-57.
Brignone et al., "A soluble form of lymphocyte activation gene-3 (IMP321) induces activation of a large range of human effector cytotoxic cells," Journal of Immunology, Sep. 15, 2007, 179(6):4202-4211.
Brundish et al., "Synthesis of N-[2-$^3$H] acetyl-D-muramyl-L-alanyl-D-iso-glutaminyl-L-alanyl-2-(1',2'-dipalmitoyl-sn-glycero-3'-phosphoryl) ethylamide of high specific radioactivity," Journal of Labelled Compounds and Radiopharmaceuticals, 1985, 22(1):29-35.
Buffen et al., "Autophagy Controls BCG-Induced Trained Immunity and the Response to Intravesical BCG Therapy for Bladder Cancer," PLOS Pathog., 2014, 10:e1004485, 10 pages.
Burgess et al., "Immunotherapeutic approaches to sarcoma," Current Treatment Options in Oncology, 2015, 16(6):1-4.
Cancer.org [online], "Key Statistics for Melanoma Skin Cancer," Jan. 12, 2022, retrieved on Apr. 18, 2022, retrieved from URL<https://www.cancer.org/cancer/melanoma-skin-cancer/about/key-statistics.html>, 2 pages.
CAS Registry No. 1054609-71-0, STN entry date: Sep. 29, 2008, STN Registry, chemical name unassigned, 1 page.
CAS Registry No. 1054657-07-6, STN entry date: Sep. 29, 2008, STN Registry, chemical name: D-Glutamamide, N-[(8ξ)-N-acetyl-β-muramoyl]-L-alanyl-N5-[(1S)-1-methyl-2-(octyloxy)ethyl]-, 1 page.
CAS Registry No. 1135450-63-3, STN entry date: Apr. 16, 2009, STN Registry, chemical name: L-Threonine, N-(N-acetyl-α-muramoyl)-L-valyl-D-α-glutaminyl-L-arginyl-L-prolyl-N6-L-alanyl-L-lysyl-, methyl ester, 1 page.
CAS Registry No. 1135450-66-6, STN entry date: Apr. 16, 2009, STN Registry, chemical name: L-Threonine, N-(N-acetyl-α-muramoyl)-L-valyl-D-α-glutaminyl-L-arginyl-L-prolyl-N6-L-valyl-L-lysyl-, methyl ester, 1 page.
CAS Registry No. 1135450-69-9, STN entry date: Apr. 16, 2009, STN Registry, chemical name: L-Threonine, N-(N-acetyl-α-muramoyl)-L-valyl-D-α-glutaminyl-L-arginyl-L-prolyl-N6-glycyl-L-lysyl-, methyl ester, 1 page.
CAS Registry No. 1135450-72-4, STN entry date: Apr. 16, 2009, STN Registry, chemical name: L-Threonine, N-(N-acetyl-α-muramoyl)-L-alanyl-D-α-glutaminyl-L-arginyl-L-prolyl-N6-glycyl-L-lysyl-, methyl ester, 1 page.
CAS Registry No. 1135450-74-6, STN entry date: Apr. 16, 2009, STN Registry, chemical name: L-Threonine, N-(N-acetyl-a-muramoyl)-L-alanyl-D-α-glutaminyl-L-arginyl-L-prolyl-N6-L-valyl-L-lysyl-, methyl ester, 1 page.
CAS Registry No. 130279-67-3, STN entry date: Nov. 9, 1990, STN Registry, chemical name: L-Lysine, N-[O-2-(acetylamino)-2-deoxy-β-D-glucopyranosyl-(1-→4)-O-(N-acetyl-β-muramosyl)-(1-→4)-O-2-(acetylamino)-2-deoxy-β-D-glucopyranosyl-(1-→4)-α-muramoyl]-L-alanyl-D-α-glutaminyl-N6-(1-oxooctadecyl)-, (1-→1')-amide with L-alanyl-D-α-glutaminyl-N6-(1-oxooctadecyl)-L-lysine (9CI), 1 page.
CAS Registry No. 130324-95-7, STN entry date: Nov. 9, 1990, STN Registry, chemical name: L-Lysine, N2-[N2-[N-[O-2-(acetylamino)-2-deoxy-β-D-glucopyranosyl-(1-→4)-O-2-(acetylamino)-2-deoxy-3-O-[7-(aminocarbonyl)-12- carboxy-1,4-dimethyl-2,5,10,18-tetraoxo-3,6,11,17-tetraazapentatriacont-1-yl]-β-D-glucopyranosyl-(1-→4)-O-2-(acetylamino)-2-deoxy-β-D-glucopyranosyl-(1-→4)-N-acetyl-β-muramoyl]-L-alanyl]-D-α-glutaminyl]-N6-(1-oxooctadecyl)-, [1R-(1R*,4S*,7R*)]—(9CI), 1 page.
CAS Registry No. 171669-22-0, STN entry date: Dec. 22, 1995, chemical name: D-Glutamamide, N-[N-acetyl-1-O-(phenylmethyl)-α-muramoyl]-L-alanyl-N5-[6-oxo-6-(phenylmethoxy)hexyl]—(9CI), 1 page.
CAS Registry No. 727353-41-5, STN entry date: Aug. 16, 2004, STN Registry, chemical name: L-Arginine, N-(N-acetyl-α-muramoyl)-L-2-aminobutanoyl-D-α-glutaminyl-, methyl ester (9CI), 1 page.
CAS Registry No. 739324-45-9, STN entry date: Sep. 3, 2004, STN Registry, chemical name: D-Glutamamide, N-(N-acetylmuramoyl)-L-alanyl-N5-[(7R)-4-hydroxy-4-oxido-10-oxo-7-[(1-oxohexadecyl)oxy]-3,5,9-trioxa-4-phosphapentacos-1-yl]—(9CI), 1 page.
CAS Registry No. 740048-83-3, STN entry date: Sep. 5, 2004, STN Registry, chemical name: L-Arginine, N-[N-acetyl-1,4,6-tris-O-(1-oxopropyl)-β-muramoyl]-L-2-aminobutanoyl-D-α-glutaminyl-, methyl ester (9CI), 1 page.
CAS Registry No. 74817-61-1, STN entry date: Nov. 16, 1984, STN Registry, chemical name: D-Glutamine, N-(N-acetylmuramoyl)-L-alanyl-, butyl ester, 1 page.
CAS Registry No. 760134-41-6, STN entry date: Oct. 10, 2004, STN Registry, chemical name: L-Arginine, N-(N-acetyl-1,4,6-tri-O-acetyl-α-muramoyl)-L-2-aminobutanoyl-D-a-glutaminyl-, methyl ester (9CI), 1 page.
CAS Registry No. 768320-98-5, STN entry date: Oct. 24, 2004, STN Registry, chemical name: L-Arginine, N-(N-acetyl-ß-muramoyl)-L-2-aminobutanoyl-D-a-glutaminyl-, methyl ester (9CI), 1 page.

(56) References Cited

OTHER PUBLICATIONS

CAS Registry No. 776255-37-9, STN entry date: Nov. 8, 2004, STN Registry, chemical name: L-Arginine, N-(N-acetyl-1,4,6-tri-O-acetyl-β-muramoyl)-L-2-aminobutanoyl-D-a-glutaminyl-, methyl ester (9CI), 1 page.
CAS Registry No. 777018-44-7, STN entry date: Nov. 8, 2004, STN Registry, chemical name: L-Arginine, N-[N-acetyl-1,4,6-tris-O-(1-oxopropyl)-α-muramoyl]-L-2-aminobutanoyl-D-a-glutaminyl-, methyl ester, (9CI), 1 page.
CAS Registry No. 78113-36-7, STN entry date: Nov. 16, 1984, STN Registry, chemical name: L-Lysine, N-(N-acetylmuramoyl)-L-alanyl-D-α-glutaminyl-N6-(1-oxooctadecyl)-, 1 page.
Cdc.gov [online], "Heart Disease Facts," Mar. 2017, retrieved on Mar. 24, 2022, retrieved from URL<https://www.cdc.gov/heartdisease/facts.htm# :~: text=Heart%20Disease%20in%20the%20United%20States&text=One%20person%20dies%20every%2036,United%20States%20from%20cardiovascular%20disease.&text=About%20659%2C000%20people%20in%20the,1%20in%20every%204%20deaths.&text=Heart%20disease%20costs%20the%20United,year%20from%202016%20to%202017>, 4 pages.
Chambenoit et al., "Specific Docking of Apolipoprotein A-I at the Cell Surface Requires a Functional ABCA1 Transporter," The Journal of Biological Chemistry, Mar. 2001, 276(13):9955-9960.
Chatzigeorgiou et al. "Blocking CD40-TRAF6 signaling is a therapeutic target in obesity associated insulin resistance," Proc. Natl. Acad. Sci. U.S.A., Feb. 2014., 18, 2014, 111(7):2685-91.
Cheng et al. "mTOR/HIF1a-Mediated Aerobic Glycolysis as Metabolic Basis for Trained Immunity," Science, Sep. 26, 2014, 345(6204):1-10.
Chinetti-Gbaguidi et al., "Macrophage subsets in atherosclerosis," Nature, Jan. 2015, 12:10-17.
Conde et al., "DC-SIGN+ Macrophages Control the Induction of Transplantation Tolerance, " Immunity, Jun. 16, 2015, 42:1143-1158.
Corry et al., "Primarily vascularized allografts of hearts in mice," Transplantation, 1973, 16(4):343-350.
Davankov, "International Union of Pure and Applied Chemistry—Analytical Chemistry Division Commission on Separation Methods in Analytical Chemistry (V3)—Analytical Chiral Separation Methods," Pure and Applied Chemistry, 1997, 69(7):1469-1474.
Demeester et al., "Synthesis of Functionalized N-Acetyl Muramic Acids To Probe Bacterial Cell Wall Recycling and Biosynthesis," J. Am. Chem. Soc., 2018, 140(30):9458-9465.
Demir et al., "Cancer screening of renal transplant patients undergoing long-term immnunosuppressive therapy," Transplantation Proceedings, Jun. 2015, 47(5):1413-1417.
Demirkiran et al., "Conversion From Calcineurin Inhibitor to Mycophenolate Mofetil-Based Immunosuppression Changes the Frequency and Phenotype of CD4+ FOXP3+ Regulatory T Cells," Clinical and Translation Research, Apr. 15, 2009, 87(7):1062-1068.
Ding et al., "Enalapril inhibits tubulointerstitial inflammation and NLRP3 inflammasome expression in BSA-overload nephropathy of rats," Acta Pharmacologica Sinica (2014) 35: 1293-1301.
Dotti, "Blocking PD-1 in cancer immunotherapy," Blood, Aug. 20, 2009, 114(8): 1457-1459.
Duarte et al., "Abstract CT099: A phase I study of intralesional *Bacillus Calmette-Guerin* (BCG) followed by ipilimumab therapy in patients with advanced metastatic melanoma," Cancer Research, 2017, 77(13_Supplement):CT099.
Duivenvoorden et al., "A statin-loaded reconstituted high-density lipoprotein nanoparticle inhibits atherosclerotic plaque inflammation," Jan. 20, 2014, 5(3065):12 pages.
Dutta et al., "Myocardial infarction accelerates atherosclerosis," Nature, Jul. 19, 2012, 487(7407):325-329.
Dzierzbicka et al., "New conjugates of muramyl dipeptide and nor-muramyl dipeptide linked to tuftsin and retro-tuftsin derivatives significantly influence their biological activity," Pharmacological Reports, 2012, 64:217-223.
Dzierzbicka et al., "Synthesis of Conjugates of Muramyl Dipeptide and nor-Muramyl Dipeptide with Retro-Tuftsin (Arg-Pro-Lys-ThrOMe) as Potential Immunostimulants," Polish Journal of Chemistry, 2004, 78:409-416.
Dzierzbicka et al., "Synthesis of new conjugates of MDP and nor-MDP with retro-tuftsin derivatives as potential immunomodulators," Polish Journal of Chemistry, 2008, 82(7):1431-1439.
Endo et al., "Regulation of cytotoxic T lymphocyte triggering by PIR-B on dendritic cells," Proceedings of the National Academy of Sciences of the United States of America, Sep. 23, 2008, 105(38):14515-14520.
Engels et al., "Spectrum of cancer risk among US solid organ transplant recipients," JAMA, 2011, 306(17):1891-1901.
Everett et al., "Rationale and design of the cardiovascular inflammation reduction trial (CIRT): A test of the inflammatory hypothesis of atherothrombosis," Am. Heart J., Aug. 2013, 166(2):199-207.
Extended European Search Report for European Application No. 17790646.8, dated Nov. 25, 2019, 9 pages.
Extended European Search Report for European Application No. 18877470.7, dated Jun. 21, 2023, 7 pages.
Extended European Search Report for European Application No. 18880348.0, dated May 21, 2021, 7 pages.
Extended European Search Report for European Application No. 22155443.9, dated May 20, 2022, 8 pages.
Fantus et al., "The Ups and Downs of TORKinibs in Transplantation," Transplantation, Aug. 2015, 99(8):e117-e118.
Farber et al., "Immunological memory: lessons from the past and a look to the future," Nature Reviews Immunology, 2016, 16(2):124-128.
Fesnak et al., "Engineered T cells: the promise and challenges of cancer immunotherapy," Nature Reviews Cancer, 2016, 16(9):566-581.
Fourcade et al., "Upregulation of Tim-3 and PD-1 expression is associated with tumor antigen-specific CD8+ T cell dysfunction in melanoma patients," Journal of Experimental Medicine, Sep. 27, 2010, 207(10):2175-2186.
Fujimoto et al., "Synthesis of crosslinked peptidoglycan fragments for investigation of their immunobiological functions, " Tetrahedron Letters, 2009, 50(26):3631-3634.
Garcia et al., "Monocytic suppressive cells mediate cardiovascular transplantation tolerance in mice," Jul. 2010, J. Clin. Invest., 120(7):2486-2496.
Gardiner et al., "Multinational Evaluation of Mycophenolic Acid, Tacrolimus, Cyclosporin, Sirolimus, and Everolimus Utilization," Ann. Transplant, Jan. 5, 2016, 21:1-11.
Garrod et al., "Murine Skin Transplantation," Journal of Visualized Experiments, 2008, 2 pages.
Geissmann et al., "Blood Monocytes Consist of Two Principal Subsets with Distinct Migratory Properties, " Jul. 2003, 19:71-82.
Gemeiner et al., "Immunomodulating Activity of 1,2-Difattyacyl-3-mercaptoglycerol Adducts," Biological Chemistry Hoppe-Seyler, 1992, 373(11):1085-1094.
GEO Accession No. GSE119370, "Expression data from graft infiltrating macrophages treated with mTORi-HDL nanobiologics," Oct. 31, 2018, 2 pages.
Guidelines for Prevention and Management of Complications Following Kidney Transplantation, Li et al. ed., Peoples Military Medical Press, Jan. 31, 2009, p. 227 (Relevance Explained in Chinese Office Action in Chinese Patent Application No. 201780041257.3, dated Dec. 3, 2020).
Gummert et al. "Newer Immunosuppressive Drugs," J Am Soc Nephrol, Jun. 1999, 10(6):1366-1380.
Hackstein et al., "Rapamycin inhibits IL-4-induced dendritic cell maturation in vitro and dendritic cell mobilization and function in vivo," Immunobiology, Blood, Jun. 1, 2003, 101(11):4457-463.
Han et al., "Structural and functional properties of V156K and A158E mutants of apolipoprotein AI in the lipid-free and lipid-bound states," Journal of Lipid Research., 2005, 46(3):589-596.
Hancock et al., "Costimulatory function and expression of CD40 ligand, CD80, and CD86 in vascularized murine cardiac allograft rejection," Proceedings of the National Academy of Sciences of the United States of America, Nov. 1996, 93:13967-13972.

(56) References Cited

OTHER PUBLICATIONS

Haug et al., "A phase I trial of Immunsuppression with anti-ICAM-1 (CD54) Matrix Biology in renal allograft recipients," Transplantation, Apr. 1993, 5594):766-773.
Heinzelmann et al., "Endotoxin and muramyl dipeptide modulate surface receptor expression on human mononuclear cells," Immunopharmacology, 2000, 48:117-128.
Herrera et al., "A Novel Pathway of Alloantigen Presentation by Dendritic Cells," The Journal of Immunology, 2004, 173:4828-4837.
Hiroyuki et al., "Synergistic Effect of Nod1 and Nod2 Agonists with Toll-Like Receptor Agonists on Human Dendritic Cells to Generate Interleukin-12 and Helper Type 1 Cells," American Society for Microbiology Infection and Immunity, Dec. 2005, 73(12):7967-7976.
Hodi et al., "Abstract CT001: Durable, long-term survival in previously treated patients with advanced melanoma (MEL) who received nivolumab (NIVO) monotherapy in a phase I trial," Cancer Research, 2016, 76(Issue 14_Supplement):CT001.
Hotchkiss et al., "Sepsis-induced immunosuppression: from cellular dysfunctions to immunotherapy," Nature Reviews Immunology, 2013, 13(12):862-874.
Huang et al., "Mammalian Septins Are Required for Phagosome Formation," Mol. Biol. Cell, Apr. 2008, 19:1717-1726.
Iknl.nl [online], "The Netherlands Cancer Registry," May 12, 2020, retrieved on Mar. 24, 2022, retrieved from URL<https://iknl.nl/en>, 2 pages.
Imhof et al., "Adhesion mechanisms regulating the migration of monocytes," Nature Reviews Immunology, Jun. 2004, 4(6):432-444.
Inamura et al., "Synthesis of peptidoglycan fragments and evaluation of their biological activity," Organic & Biomolecular Chemistry, 2006, 4(2):232-242.
International Preliminary Report on Patentability in International Application No. PCT/US2017/030444, dated Oct. 30, 2018, 8 pages.
International Preliminary Report on Patentability in International Application No. PCT/US2018/061935, dated May 26, 2020, 25 pages.
International Preliminary Report on Patentability in International Application No. PCT/US2018/061939, dated May 26, 2020, 20 pages.
International Preliminary Report on Patentability in International Appln. No. PCT/US2022/021035, mailed on Sep. 28, 2023, 9 pages.
International Search Report and Written Opinion in International Appln. No. PCT/US2023/065166, mailed on Sep. 29, 2023, 16 pages.
International Search Report and Written Opinion of the International Searching Authority for International Application No. PCT/US2017/030444, dated Sep. 22, 2017, 11 pages.
International Search Report and Written Opinion of the International Searching Authority for International Application No. PCT/US2018/061935, dated Apr. 19, 2019, 31 pages.
International Search Report and Written Opinion of the International Searching Authority for International Application No. PCT/US2018/061939, dated Feb. 22, 2019, 22 pages.
International Search Report and Written Opinion of the International Searching Authority for International Application No. PCT/US2022/021035, dated Jul. 25, 2022, 13 pages.
Invitation to Pay Additional Fees in International Appln. No. PCT/US2022/021035, dated May 19, 2022, 2 pages.
Ishida, "Synthesis and Immunoadjuvant Activity of NAcetyl-6-O-phosphono-muramoy1-1-alanyl-d-isoglutamine Methyl Ester and Its Lipophilic Derivatives," Agricultural and Biological Chemistry, 1989, 53:1057-1063.
Jeek et al., "Synthesis of tetrasaccharide containing glycopeptides related to bacterial cell wall starting from free tetrasaccharide by the pentafluorophenyl ester method," Collection of Czechoslovak Chemical Communications, 1990, 55(5), 1326-1335.
Jonas, "Reconstitution of High-Density Lipoproteins," Methods in Enzymology, 1986, 128:553-582.
Kanehisa et al., "KEGG for integration and interpretation of large-scale molecular data sets," Nucleic Acids Research, 2012, 40:D109-D114.
Kawai et al., "Thromboembolic complications after treatment with monoclonal antibody against CD40 ligand," Nature Medicine, Feb. 2000, 6(2):114.
Khalil et al., "The future of cancer treatment: immunomodulation, CARs and combination immunotherapy," Nature Reviews Clinical Oncology, 2016, 13(5):273-290.
Kidner et al., "Combined intralesional Bacille Calmette-Guerin (BCG) and topical imiquimod for in-transit melanoma," Author Manuscript, J. Immunother., 2012, 35(9):716-20.
Kim et al., "S6K1 Negatively Regulates TAK1 Activity in the Toll-Like Receptor Signaling Pathway," Molecular and Cellular Biology, 2014, 34(3):510-521.
Kingwell et al., "HDL-targeted therapies: progress, failures and future," Nature Reviews Drug Discovery, 2014, 13:445-464.
Kirk et al., "Treatment with humanized monoclonal antibody against CD154 prevents acute renal allograft rejection in nonhuman primates," Nature Medicine, Jun. 1999, 5(6):686-693.
Krivorutchenko et al., "Study of the adjuvant activity of new MDP derivatives and purified saponins and their influence on HIV-1 replication in vitro," Vaccine, 1997, 15(Dec. 2013):1479-1486.
Kruidenier et al., "A selective jumonji H3K27 demethylase inhibitor modulates the proinflammatory macrophage response," Nature, 2012, 488(7411):404-408.
Kuai et al., "High-Density Lipoproteins: Nature's Multifunctional Nanoparticles," ACS Nano, 2016, 10(3):3015-3041.
Kupel et al., "Long-term risk of pulmonary embolism in solid-organ transplant recipients," Experimental and Clinical Transplantation, Apr. 2015, 13(Suppl 1):223-227.
Kur'yanov et al., "Synthesis of alkyl ß-glycosides of 6-(N-acetylmuramoyl-L-alanyl-D-isoglutaminylamino)hexanoic acid and its 4-aminobutyl ester," Chemistry of Natural Compounds, 1994, 30(3):390-394.
Kuryanov et al., "Synthesis of muramyldipeptide lipophilic derivatives," Bioorganicheskaya Khimiya, 1994, 20(4):439-447 (with English abstract).
Lai et al., "Development of Luciferase Reporter-Based Cell Assays," ASSAY and Drug Development Technologies, 2006, 4(3):307-315.
Lameijer, "Targeting macrophage dynamics to regulate the cardiovascular immune response," University of Amsterdam, Jan. 16, 2018,.
Langmead et al., "Fast gapped-read alignment with Bowtie 2," Nat. Methods, 2013, 9(4):357-359.
Larosa et al., "The Innate Immune System in Allograft Rejection and Tolerance," J Immunol, 2007, 178:7503-7509.
Leeper et al., "High-Density Lipoprotein Nanoparticle Imaging in Atherosclerotic Vascular Disease," JACC: Basic to Translational Science, 2017, 2(1):98-100.
Leman et al., "Molecules That Mimic Apolipoprotein A-I: Potential Agents for Treating Atherosclerosis," J. Med. Chem., 2014, 57:2169-2196.
Lien, "Top 10 things primary care physicians should know about maintenance immunosuppression for transplant recipients," The American Journal of Medicine, 2015, 17 pages.
Linsel-Nitschke et al., "HDL as a target in the treatment of atherosclerotic cardiovascular disease," Nature Reviews Drug Discovery, 2005, 4(3):193-205.
Liu et al., "Innate NK Cells and Macrophages Recognize and Reject Allogeneic Nonself In Vivo via Different Mechanisms," J. Immunol., 2012, 188:2703-2711.
Liu et al., "Insight into the Glucose Metabolism of Immune Cells in Sepsis," Journal of Anesthesia and Perioperative Medicine, 2017, 4(1):38-44.
Liu et al., "Rat CD8+ FOXP3+ T suppressor cells mediate tolerance to allogeneic heart transplants, inducing PIR-B in APC and rendering the graft invulnerable to rejection," Transplant Immunology, Dec. 2004, 13:239-247.

(56) References Cited

OTHER PUBLICATIONS

Liu et al., "Solid-phase synthesis of muramyl dipeptide (mdp) derivatives using a multipin method," Bioorganic & Medicinal Chemistry Letters, 2000, 10:1361-1363.
Loo et al., "Development of an Fc-enhanced anti-B7-H3 monoclonal antibody with potent antitumor activity," Clinical Cancer Research, May 21, 2012, 18(14):3834- 3845.
Lutgens et al., "Atherosclerosis: Targeting the immune system," ISA meeting, Amsterdam, May 23-26, 2015, 48 pages.
Lutgens et al., "Both early and delayed anti-CD40L antibody treatment induces a stable plaque phenotype," PNAS, 2000, 97(13):7464-7469.
Lutgens et al., "Deficient CD40-TRAF6 signaling in leukocytes prevents atherosclerosis by skewing the immune response toward an antiinflammatory profile," The Journal of Experimental Medicine, 2010, 207:391-404.
Lutgens et al., "Requirement for CD154 in the progression of atherosclerosis," Nature Medicine, Nov. 1999, 5(11):1313-1316.
Ma et al., "Paclitaxel Nano-Delivery Systems: A Comprehensive Review," J Nanomed Nanotechnol., Feb. 18, 2013, 4(2): 1000164.
Mach et al., "Reduction of atherosclerosis in mice by inhibition of CD40 signaling," Nature, Jul. 9, 1998, 394:200-203.
Maldonado et al., "Polymeric synthetic nanoparticles for the induction of antigen- specific immunological tolerance," PNAS, 2014, E156-E165.
Martner et al. Fundamentals of Practical Clinical Immunology, 1st Ed., Vinca Press, Jun. 1993, pp. 314-315 (Relevance Explained in Chinese Office Action in Chinese Patent Application No. 201880086231.5, dated Nov. 3, 2022).
Matsumoto et al., "Stimulation of nonspecific resistance to infection induced by 6-O-acyl muramyl dipeptide analogs in mice," Infect. and Immun., 1981, 32(2):748-758.
Maury et al., "Raised Serum Levels of Cachectin/Tumor Necrosis Factor a In Renal Allograft Rejection," J. Exp. Med., 1987, 166:1132-1137.
Medical Immunology, He et al. ed., Henan Science and Technology Press, Jan. 31, 1990, p. 116 (Relevance Explained in Chinese Office Action in Chinese Patent Application No. 201780041257.3, dated Dec. 3, 2020).
Megias et al., "TLR2, TLR4 and Dectin-1 signalling in hematopoietic stem and progenitor cells determines the antifungal phenotype of the macrophages they produce," Microbes and Infection, 2016, 18:354-363.
Meshcheryakova et al., "Evidence for correlation between the intensities of adjuvant effects and NOD2 activation by monomeric, dimeric and lipophylic derivatives of N- acetylglucosaminyl-N-acetylmuramyl peptides," Vaccine, 2007, 25:4515-4520.
Mills et al., "Succinate Dehydrogenase Supports Metabolic Repurposing of Mitochondria to Drive Inflammatory Macrophages," Cell, 2016, 167:457-470.
Mitroulis et al., "Modulation of Myelopoiesis Progenitors is an Integral Component of Trained Immunity," Cell, Jan. 2018, 172:147-161.
Miyake et al., "Critical role of macrophages in the marginal zone in the suppression of immune responses to apoptotic cell-associated antigens," J. Clin. Invest., Aug. 2007, 117(8):2268-2278.
Modern Diagnosis and Therapy of Arteriosclerotic Diseases, Wei et al. ed., Jindun Publishing House, May 30, 2015, p. 598 (Relevance Explained in Chinese Office Action in Chinese Patent Application No. 201780041257.3, dated Dec. 3, 2020).
Mohammadi et al., "Specificity of the Transport of Lipid II by FtsW in Escherichia coli," The Journal of Biological Chemistry, 2014, 289(21):14707-14718.
Moore et al., "Macrophages in atherosclerosis: a dynamic balance," Oct. 2013, 13(10):709-721.
Moroder et al., "Synthesis of thiol-functionalized N-acetylmuramyl peptide congeners suitable for their conjugation to target molecules," Biological Chemistry Hoppe- Seyler, 1989, 370:365-375.
Moroi et al., "Physico-chemical properties of muroctasin," Arzneimittel-Forschung, 1988, 38(7A):953-959.
Morton et al., "BCG immunotherapy of malignant melanoma: summary of a seven- year experience," Annals of Surgery, 1974, 180:635-643.
Mudge et al., "Creating reference gene annotation for the mouse C57BL6/J genome assembly," Mamm Genome, Jul. 18, 2015, 26:366-378.
Mulder et al., "Therapeutic targeting of trained immunity," Nat. Rev. Drug Discov., 2019, 18(7):553-566.
Naesens et al., "Calcineurin Inhibitor Nephrotoxicity," Clin. J. Am. Soc. Nephrol., 2009, 4:481-508:481-508.
Nahrendorf et al., "The healing myocardium sequentially mobilizes two monocyte subsets with divergent and complementary functions," The Journal of Experimental Medicine, Nov. 26, 2007, 204(12):3037-47.
Nakamura et al., "Rapamycin prolongs cardiac allograft survival in a mouse model by inducing myeloid-derived suppressor cells," American Journal of Transplantation, Sep. 2015, 15(9):2364-77.
Netea et al., "Hypothesis: stimulation of trained immunity as adjunctive immunotherapy in cancer," Journal of Leukocyte Biology, Dec. 2017, 102:1323-1331.
Netea et al., "Innate immune memory: a paradigm shift in understanding host defense," Nature Immunology, 2015, 16(7):675-679.
Netea et al., "Trained immunity: A program of innate immune memory in health and disease," Science, Apr. 2016, 352(6284): aaf1098, 23 pages.
Nicodeme et al., "Suppression of inflammation by a synthetic histone mimic," Nature, 2010, 468(7327):1119-1123.
Oberbarnscheidt et al., "Innate allorecognition," Immunological Reviews, Mar. 2014, 258(1):145-9.
Oberbarnscheidt et al., "Non-self recognition by monocytes initiates allograft rejection," The Journal of Clinical Investigation, Aug. 1, 2014, 124(8):3579-89.
Ochando et al., "Alloantigen-presenting plasmacytoid dendritic cells mediate tolerance to vascularized grafts," Nature Immunology, Jun. 2006, 7(6):652-62.
Ochando et al., "Innate immune cell collaborations instigate transplant tolerance," American Journal of Transplantation, 2014, 14:2441-2443.
Office Action in Australian Appln. No. 2017257189, dated Feb. 28, 2022, 3 pages.
Office Action in Australian Appln. No. 2017257189, dated Mar. 16, 2021, 6 pages.
Office Action in Australian Appln. No. 2018370237, mailed on Oct. 20, 2023, 6 pages.
Office Action in Canadian Appln. No. 3021645, mailed on Jul. 13, 2023, 5 pages.
Office Action in Chinese Appln. No. 201580085777.5, dated Jan. 19, 2021, 15 pages (with English Translation).
Office Action in Chinese Appln. No. 201580085777.5, dated Jul. 3, 2020, 13 pages (with English Translation).
Office Action in Chinese Appln. No. 201780041257.3, dated Apr. 15, 2022, 31 pages (with English Translation).
Office Action in Chinese Appln. No. 201780041257.3, dated Dec. 3, 2020, 26 pages (with English Translation).
Office Action in Chinese Appln. No. 201780041257.3, dated Oct. 18, 2021, 34 pages (with English Translation).
Office Action in Chinese Appln. No. 201880086231.5, dated Jan. 28, 2022, 23 pages (with English Translation).
Office Action in Chinese Appln. No. 201880086231.5, dated May 29, 2023, 21 pages (with English Translation).
Office Action in Chinese Appln. No. 201880086231.5, dated Nov. 3, 2022, 24 pages (with English Translation).
Office Action in Chinese Appln. No. 201880087082.4, dated Apr. 13, 2022, 17 pages (with English Translation).
Office Action in Chinese Appln. No. 201880087082.4, dated Jan. 12, 2023, 9 pages (with English Translation).
Office Action in Chinese Appln. No. 201880087082.4, dated Jun. 14, 2023, 10 pages (with English translation).
Office Action in Japanese Appln. No. 2018-556339, dated Feb. 1, 2022, 6 pages (with English Translation).
Office Action in Japanese Appln. No. 2018-556339, dated Nov. 22, 2022, 6 pages (with English Translation).

(56) References Cited

OTHER PUBLICATIONS

Office Action in Japanese Appln. No. 2020-545063, dated Nov. 15, 2022, 9 pages (with English Translation).
Office Action in Japanese Appln. No. 2020-545063, mailed on Jul. 3, 2023, 6 pages (with English translation).
Office Action in Japanese Appln. No. 2020-545065, dated Nov. 22, 2022, 7 pages (with English Translation).
Office Action in United States U.S. Appl. No. 18/121,527, mailed on Oct. 6, 2023, 10 pages.
Organ Transplantation, Yuyuan Liu ed., Human Science and Technology Press, Oct. 31, 2009, p. 52 (Relevance Explained in Chinese Office Action in Chinese Patent Application No. 201780041257.3, dated Dec. 3, 2020).
Pahl et al., "Macrophages inhibit human osteosarcoma cell growth after activation with the bacterial cell wall derivative liposomal muramyl tripeptide in combination with interferon-y," J Exp Clin Cancer Res. 2014; 33:27, 13 pages.
Paolicelli et al., "Surface-modified PLGA-based Nanoparticles that can Efficiently Associate and Deliver Virus like Particles," Nanomedicine, Aug. 24, 2010, 5(6):843-853.
Pardoll et al., "The blockade of immune checkpoints in cancer immunotherapy," Nature Reviews Cancer, 2012, 12(4):252-264.
Pardoll, "Immunology beats cancer: a blueprint for successful translation," Nat. Immunol., 2012, 13(12):1129-1132.
Pérez-Medina et al., "In vivo PET imaging of HDL in multiple atherosclerosis models," JACC: Cardiovascular Imaging, Aug. 2016, 9(8):950-61.
Pérez-Medina et al., "Nanoreporter PET predicts the efficacy of anti-cancer nanotherapy," Nature Communications, 2016, 7:11838.
Pérez-Medina et al., "PET imaging of tumor-associated macrophages with 89Zr- labeled high-density lipoprotein nanoparticles," Journal of Nuclear Medicine, Aug. 2015, 56(8):1272-7.
Potteaux et al., "Suppressed monocyte recruitment drives macrophage removal from atherosclerotic plaques of Apoe / mice during disease regression," The Journal of Clinical Investigation, May 2, 2011, 121(5):2025-36.
Priem et al., "Trained Immunity-Promoting Nanobiologic Therapy Suppresses Tumor Growth and Potentiates Checkpoint Inhibition," Cell 2020, 183:786-801.
Pritchard, "Sourcing a chemical succession for cyclosporin from parasites and human pathogens," Drug Discovery Today, May 2005, 10(10):688-691.
PubChem [Online], "SID 40944914," Dec. 5, 2007, [Retrieved on Aug. 9, 2022], retrieved from URL<https://pubchem.ncbi.nlm.nih.gov/substance/40944914>, 5 pages.
Pullen et al., "CD40-tumor necrosis factor receptor-associated factor (TRAP) interactions: regulation of CD40 signaling through multiple TRAP binding sites and TRAP hetero-oligomerization," Biochemistry, 1998, 37:11836-11845.
Ramos-Cabrer et al., "The effect of loading nascent HDL with gadolinium phospholipids in the structural stability of the particles," Proceedings of the International Society for Magnetic Resonance in Medicine, 2014, 22(2014), 1 page.
Ridker et al., "Interleukin-1ß inhibition and the prevention of recurrent cardiovascular events: rationale and design of the Canakinumab Anti-inflammatory Thrombosis Outcomes Study (CANTOS)," American Heart Journal, Oct. 1, 2011, 162(4):597- 605.
Ritchie et al., "limma powers differential expression analyses for RNA-sequencing and microarray studies," Nucleic Acids Research, Apr. 20, 2015, 43(7):e47-, 13 pages.
Robbins et al., "Local proliferation dominates lesional macrophage accumulation in atherosclerosis," Nature Medicine, Sep. 2013, 19(9): 1166-1172, 15 pages.
Saeed et al., "Epigenetic programming of monocyte-to-macrophage differentiation and trained innate immunity," Science, 2014, 345(6204):1251086.
Sakuishi et al., "Targeting Tim-3 and PD-1 pathways to reverse T cell exhaustion and restore anti-tumor immunity," Journal of Experimental Medicine, Sep. 27, 2010, 207(10):2187-2194.
Sanchez-Gaytan et al., "HDL-mimetic PLGA nanoparticle to target atherosclerosis plaque macrophages," Author Manuscript, Bioconjug. Chem., 2015, 26(3):443-451.
Sanchez-Gaytan et al., "Real-Time Monitoring of Nanoparticle Formation via FRET Imaging," Author Manuscript, Angewandte Chemie International Edition, 2017, 56(11):2923-2926.
Schönbeck et al., "CD40 signaling and plaque instability," Circulation Research, Dec. 7, 2001, 89(12):1092-103.
Schönbeck et al., "Inhibition of CD40 signaling limits evolution of established atherosclerosis in mice," Proceedings of the National Academy of Sciences, Jun. 20, 2000, 97(13):7458-7463.
Schwarz et al."Identification of differentially expressed genes induced by transient ischemic stroke," Brain Res Mol Brain Res, 2002; 101(1-2):12-22.
Scientificamerican.com [online], "Cancer Immunotherapy: The Cutting Edge Gets Sharper," Oct. 1, 2015, retrieved on Mar. 24, 2022, retrieved from URL<https://www.scientificamerican.com/article/cancer-immunotherapy-the-cutting-edge-gets-sharper/# :~: text=Artificially%20boosting%20the%20body's%20immune,the%20past%20couple%20of%20years>, 5 pages.
Segrest et al., "The Amphipathic a Helix: A Multifunctional Structural Motif in Plasma Apolipoproteins," Advances in Protein Chemistry, 1994, 45:303-369.
Shah et al., "Effects of recombinant apolipoprotein A-IMilano on aortic atherosclerosis in apolipoprotein E-deficient mice, " Circulation, Mar. 3, 1998, 97(8):780-5.
Shi et al., "Monocyte recruitment during infection and inflammation," Nature Reviews Immunology, Nov. 2011, 11(11): 762-74.
Shimizu et al., "Host CD40 ligand deficiency induces long-term allograft survival and donor-specific tolerance in mouse cardiac transplantation but does not prevent graft arteriosclerosis," The Journal of Immunology, Sep. 15, 2000, 165(6):3506-18.
Shuchman, "Trading restenosis for thrombosis? New questions about drug-eluting stents," New England Journal of Medicine, Nov. 9, 2006, 355(19): 1949-52.
Skajaa et al., "High-density lipoprotein-based contrast agents for multimodal imaging of atherosclerosis," Arteriosclerosis, Thrombosis, and Vascular Biology, 2010, 30(2):169-176.
Skajaa et al., "The biological properties of iron oxide core high-density lipoprotein in experimental atherosclerosis," Biomaterials, 2011, 32:206-213.
Song et al., "Immune Training Unlocks Innate Potential," Cell, Jan. 11, 2018, 172:3-5.
Sporri et al., "Inflammatory mediators are insufficient for full dendritic cell activation and promote expansion of CD4+ T cell populations lacking helper function," Nature immunology, 2005, 6:163-170.
Stone et al., "A prospective natural-history study of coronary atherosclerosis," New England Journal of Medicine, Jan. 20, 2011, 364(3):226-35.
Sun et al., "Interactions of NIPAM nanogels with model lipid multi-bilayers: A neutron reflectivity study," Journal of Colloid and Interface Science, 2018, 536:598- 608.
Swirski et al., "Leukocyte behavior in atherosclerosis, myocardial infarction, and heart failure," Science, Jan. 11, 2013, 339(6116): 161-6.
Swirski et al., "Ly-6Chi monocytes dominate hypercholesterolemia-associated monocytosis and give rise to macrophages in atheromata," The Journal of Clinical Investigation, Jan. 2, 2007, 117(1): 195-205.
Swirski et al., "Monocyte accumulation in mouse atherogenesis is progressive and proportional to extent of disease," Proceedings of the National Academy of Sciences of the United States of America, Jul. 5, 2006, 103(27): 10340-10345.
Swirski et al., "Myeloperoxidase-rich Ly-6C+ myeloid cells infiltrate allografts and contribute to an imaging signature of organ rejection in mice," The Journal of Clinical Investigation, Jul. 1, 2010, 120(7):2627-34.
Tang et al., "Immune cell screening of a nanoparticle library improves atherosclerosis therapy," PNAS, Oct. 2016, 113(44):E6731-E6740.
Tang et al., "Inhibiting macrophage proliferation suppresses atherosclerotic plaque inflammation," Science Advances, Apr. 1, 2015, 1(3):e1400223, 10 pages.

(56) References Cited

OTHER PUBLICATIONS

Tehranirokh et al., "Microfluidic devices for cell cultivation and proliferation," Biomicrofluidics, 2013, 7:51502.
Tenahrench et al., "The Basic and Clinical of Coliform Cancer," 1st Ed., Shanghai Scientific and Technical Literature Press, Sep. 1999, pp. 252-253 (Relevance Explained in Chinese Office Action in Chinese Patent Application No. 201880086231.5, dated Nov. 3, 2022).
Thomson et al., "Immunoregulatory functions of mTOR inhibition," Nature Reviews Immunology, May 2009, 9(5):324-37.
Transplantatiestichting.nl [online], "Cijfers over donatie en transplantatie," available on or before Mar. 2020, retrieved on Mar. 24, 2022, retrieved from URL<https://www.transplantatiestichting.nl/publicaties-en-naslag/cijfers-over-donatie-en-transplantatie>, 5 pages.
Unos.org [online], "Data," Nov. 2002, retrieved on Mar. 24, 2022, retrieved from URL<https://unos.org/data/>, 3 pages.
Valenta et al., "Macrophage PLTP is atheroprotective in LDLr-deficient mice with systemic PLTP deficiency," Journal of Lipid Research, Jan. 1, 2008, 49(1):24-32.
Van den Berg et al., "Blocking CD40-TRAF6 interactions by small-molecule inhibitor 6860766 ameliorates the complications of diet-induced obesity in mice," International Journal of Obesity, May 2015, 39(5):782-90.
Van der Valk et al., "Prednisolone-containing liposomes accumulate in human atherosclerotic macrophages upon intravenous administration," Author Manuscript, Nanomedicine, 2015, 11:1039-1046.
Vanneman et al., "Combining immunotherapy and targeted therapies in cancer treatment," Nature Reviews Cancer, 2012, 12(4):237-251.
Vannieuwenhze et al., "The total synthesis of lipid I," J. Am. Chem. Soc., 2001, 123:6983-6988.
Vugts et al., "Synthesis of Phosphine and Antibody—Azide Probes for in Vivo Staudinger Ligation in a Pretargeted Imaging and Therapy Approach," Bioconjugate Chem., 2011, 22:2072-2081.
Wang et al., "Glycan sequence-dependent Nod2 activation investigated by using a chemically synthesized bacterial peptidoglycan fragment library," ChemBioChem, 2013, 14:482-488.
Wang et al., "GO-function: deriving biologically relevant functions from statistically significant functions," Briefings in Bioinformatics, Mar. 1, 2012, 13(2):216-27.
Wang et al., "Peptidoglycan microarray as a novel tool to explore protein-ligand recognition," Biopolymers (Pept. Sci.), 2016, 106(4):422-429.
Wang et al., "Synthesis of characteristic Mycobacterium peptidoglycan (PGN) fragments utilizing with chemoenzymatic preparation of meso-diaminopimelic acid (DAP), and their modulation of innate immune responses," Organic & Biomolecular Chemistry, 2016, 14:1013-1023.
Wasan et al., "Impact of lipoproteins on the biological activity and disposition of hydrophobic drugs: implications for drug discovery," Nature Review Drug Discovery, 2008, 7:84-99.
Wells et al., "Requirement for T-cell apoptosis in the induction of peripheral transplantation tolerance," Nature Medicine, Nov. 1999, 5(11):1303-7.
Willems et al., "Lipophilic Muramyl Dipeptide-Antigen Conjugates as Immunostimulating Agents," ChemMedChem Communications, 2016, 11:190-198.
Wu et al., "Homeostatic proliferation is a barrier to transplantation tolerance," Nature Medicine, Jan. 2004, 10(1):87-92.
Yan et al., "Indexing TNF-a gene expression using a gene-targeted reporter cell line," BMC Biology, 2009, 7:8.
Yang et al., "Rapamycin-conditioned dendritic cells induced immune tolerance through the regulation of Treg/Th17 cells in mice," Natl. Med. J. China, 2015, 95(30):2469-2473 (with English Abstract).
Yang et al., "Scavenger receptor-BI is a receptor for lipoprotein(a)," Journal of Lipid Research, Sep. 1, 2013, 54(9):2450-7.
Ye et al., "Imaging Macrophage and Hematopoietic Progenitor Proliferation in Atherosclerosis," Circulation Research, 2015, 117(10):835-845.
Zamanian-Daryoush et al., "The Cardioprotective Protein Apolipoprotein A1 Promotes Potent Anti-tumorigenic Effects," Journal of Biological Chemistry, Jul. 19, 2013, 288(29):21237-21252.
Zarzycka et al., "Discovery of small molecule CD40-TRAF6 inhibitors," Journal of Chemical Information and Modeling, Jan. 27, 2015, 55:294-307.
Zecher et al., "An innate response to allogeneic nonself mediated by monocytes," The Journal of Immunology, Dec. 15, 2009, 183(12):7810-6.
Zemlyakov et al., "Synthesis of muramyldipeptide and their isotyped-labeled analogues," Khimiya Prirodnykh Soedinenii, 1990, 2:245-248 (English Translation only).
Zemlyakov et al., "Synthesis of the y-octadecylamide of N-acetylmuramoyl-L-alanyl-D-isoglutamine," Khimiya Prirodnykh Soedinenii, 1988, 6:892-893 (English Translation only).
Zemlyakov, "Immobilization of synthetic glycopeptides on polymeric supports," Chemistry of Natural Compounds, 1998, 34(1):80-85.
Zhang et al., "A General Framework for Weighted Gene Co-Expression Network Analysis," Statistical Applications in Genetics and Molecular Biology, Aug. 12, 2005, 4(1): 45 pages.
Zhao et al., "Augmenting Drug-Carrier Compatibility Improves Tumour Nanotherapy Efficacy," Nature Communications, Apr. 2016, 7:11221, 11 pages.
Zheng et al., "HDL mimetic CER-001 targets atherosclerotic plaques in patients," Atherosclerosis, 2016, 251:381-388.
Zou et al., "PLGA/liposome hybrid nanoparticles for short-chain ceramide delivery," Pharmaceutical Research, Mar. 2014, 31(3):684-693.
Extended European Search Report in European Appln. No. 22772322.8, mailed on Feb. 11, 2025, 5 pages.
Ogawa et al., "Muramyl Dipeptide and its Derivatives: Peptide Adjuvant in Immunological Disorders and Cancer Therapy", Curr Bioact Compd, Sep. 2011, 7(3):180-197 (Author Manuscript, 37 pages).

* cited by examiner

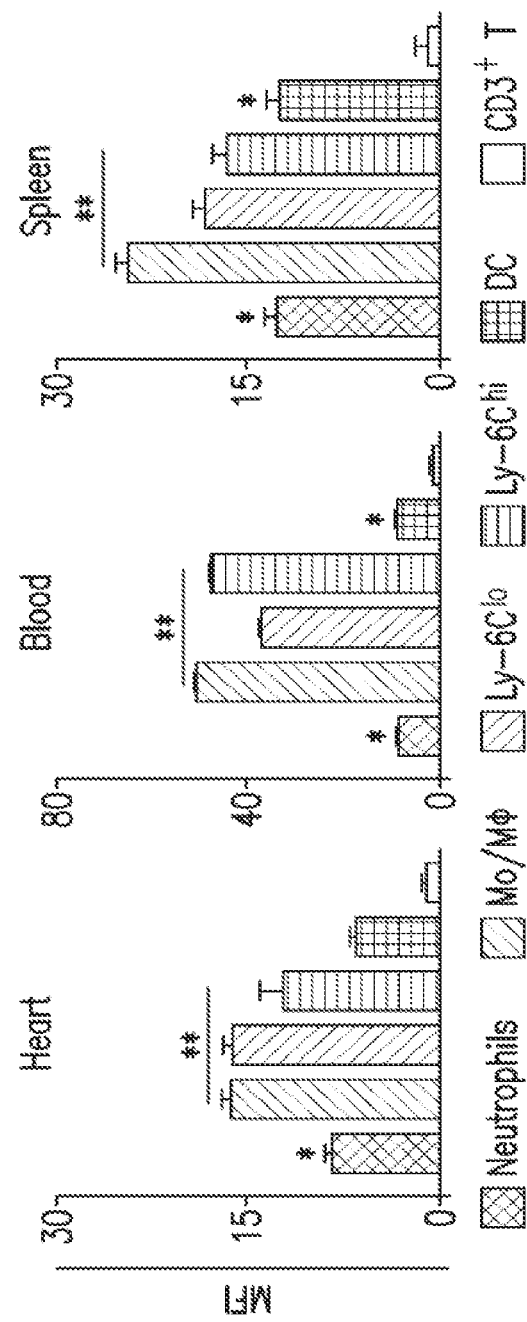

| | Placebo | HDL | TRAF6i-HDL | p-value |
|---|---|---|---|---|
| Red blood cells (M/uL) | 9.03 ±0.38 | 8.54 ±0.20 | 8.84 ±0.50 | 0.0632 |
| Hemoglobin (g/dL) | 13.13 ±0.61 | 12.58 ±0.36 | 13.01 ±0.72 | 0.2450 |
| Hematocryt (%) | 50.77 ±2.67 | 48.32 ±1.93 | 48.31 ±2.43 | 0.0947 |
| Reticulocytes (K/uL) | 345.80 ±49.82 | 729.06 ±186.0 | 675.00 ±98.80 | 0.0005 |
| Platelets (K/uL) | 546.11 ±138.2 | 807.00 ±167.6 | 576.13 ±148.4 | 0.0256 |
| White blood cells (K/uL) | 0.62 ±0.25 | 1.276 ±0.63 | 0.92 ±0.32 | 0.0343 |
| Neutrophils (K/uL) | 0.27 ±0.09 | 0.506 ±0.27 | 0.30 ±0.13 | 0.0536 |
| Lymphocytes (K/uL) | 0.29 ±0.16 | 0.53 ±0.31 | 0.52 ±0.17 | 0.0590 |
| Monocytes (K/uL) | 0.044 ±0.03 | 0.136 ±0.06 | 0.089 ±0.06 | 0.0156 |
| Eosinophils (K/uL) | 0.014 ±0.007 | 0.088 ±0.077 | 0.021 ±0.016 | 0.0055 |
| Basophils (K/uL) | 0.009 ±0.008 | 0.016 ±0.005 | 0.003 ±0.002 | 0.0113 |

FIG. 20

| | Placebo | TRAF6i-HDL | p-value |
|---|---|---|---|
| Alkaline phosphatase (U/L) | 56,77 ±7.99 | 74,3 ±17.16 | 0.02 |
| Alanine aminotransferase (U/L) | 348,8 ±293.6 | 434,3 ±342.7 | 0.70 |
| Aspartate aminotransferase (U/L) | 784,3 ±463 | 636,5 ±260.2 | 0.66 |
| Creatine kinase (U/L) | 155,8 ±138.4 | 121,3 ±0.25 | 0.76 |
| Blood urea nitrogen (mg/dL) | 24,77 ±5.93 | 21 ±2.31 | 0.12 |
| Cholesterol (mg/dL) | 1265,6 ±403.9 | 1481,6 ±251.8 | 0.32 |
| Triglyceride (mg/dL) | 121,55 ±47.19 | 162,7 ±43.03 | 0.11 |
| Glucose (mg/dL) | 232,11 ±113.9 | 298 ±174.5 | 0.33 |
| Calcium (mg/dL) | 8,89 ±1.27 | 8,9 ±1.10 | 0.93 |
| Phosphorus (mg/dL) | 12,44 ±2.50 | 12,1 ±1.10 | 0.61 |
| Bicarbonate (mmol/L) | 8 ±2.06 | 8,8 ±2.44 | 0.59 |
| Total protein (g/dL) | 4,89 ±0.78 | 5,2 ±0.42 | 0.32 |

FIG.21

| GO ID | GO term | Fold enrichment | Adjusted p-value | Genes |
|---|---|---|---|---|
| GO:0072562 | Blood microparticle | 6.29 | 0.0005 | Serping1; C3; Clu; Cp; Eng; Apoe; Lgals3bp; Serpina3n; Trf; Ywhaz; Sdcbp; F13a1 |
| GO:0009986 | Cell surface | 2.33 | 0.0005 | Ace; Adam10; Adam8; Aoc3; Apoe; Cav2; Cd22; Cd4; Cd9; Clu; Csf1r; Eng; Ghr; Gsr; Hspa5; Itga5; Itgav; Anpep; Sept2; Plg/m; Selp; Sdc3; Tgfbr2; Trf; Vegfa; Vwf; Rala; Cd274; Tmx3; Sulf2; Mxra8; Erp44; Hnrnpm; Heg1; Siglece; Plxnb2; Stab2; Ece1; Lrrc8a |
| GO:0005925 | Focal Adhesion | 2.42 | 0.0045 | Adam10; Rhoa; Cav2; Cd9; Csrp1; Dab2; Eng; Flt1; Gna12; Hspa5; Itga5; Itgav; Ppp1cb; Pxn; Sorbs3; Tln1; Tns1; Hsp90b1; Vim; Ywhaz; G3bp1; Rala; Afap1; Dcaf6; Actr3; Rab21; Git1; Nup214 |
| GO:0005924 | Cell-substrate adherent junction | 2.39 | 0.0046 | Adam10; Rhoa; Cav2; Cd9; Csrp1; Dab2; Eng; Flt1; Gna12; Hspa5; Itga5; Itgav; Ppp1cb; Pxn; Sorbs3; Tln1; Tns1; Hsp90b1; Vim; Ywhaz; G3bp1; Rala; Afap1; Dcaf6; Actr3; Rab21; Git1; Nup214 |
| GO:0030055 | Cell-substrate junction | 2.37 | 0.0046 | Adam10; Rhoa; Cav2; Cd9; Csrp1; Dab2; Eng; Flt1; Gna12; Hspa5; Itga5; Itgav; Ppp1cb; Pxn; Sorbs3; Tln1; Tns1; Hsp90b1; Vim; Ywhaz; G3bp1; Rala; Afap1; Dcaf6; Actr3; Rab21; Git1; Nup214 |
| GO:0009897 | External side of plasma membrane | 2.96 | 0.0046 | Ace; Cd22; Cd4; Cd9; Eng; Gsr; Itga5; Itgav; Anpep; Apoe; Selp; Tgfbr2; Trf; Vwf; Cd274; Heg1; Siglece; Stab2; Ece1 |
| GO:0005912 | Adherens junction | 2.22 | 0.0055 | Adam10; Rhoa; Cav2; Cd9; Csrp1; Dab2; Dlg1; Eng; Flt1; Gna12; Hspa5; Itga5; Itgav; Ndrg1; Ppp1cb; Pxn; Sorbs3; Tln1; Tns1; Hsp90b1; Vim; Ywhaz; G3bp1; Rala; Afap1; Dcaf6; Actr3; Rab21; Git1; Nup214 |
| GO:0070161 | Anchoring junction | 2.17 | 0.0074 | Adam10; Rhoa; Cav2; Cd9; Csrp1; Dab2; Dlg1; Eng; Flt1; Gna12; Hspa5; Itga5; Itgav; Ndrg1; Ppp1cb; Pxn; Sorbs3; Tln1; Tns1; Hsp90b1; Vim; Ywhaz; G3bp1; Rala; Afap1; Dcaf6; Actr3; Rab21; Git1; Nup214 |

FIG. 22

| | | | |
|---|---|---|---|
| GO:0098552 | Side of membrane | 2.28 | 0.0109 | Cav2; Cd22; Cd4; Cd9; Dlg1; Ace; Apoe; Eng; Gna11; Gna12; Gsr; Itga5; Itgav; Anpep; S100a6; Selp; Tgfbr2; Trf; Vwf; Cd274; Hegl; Siglece; Stab2; Rab21; Ece1 |
| GO:0005615 | Extracellular space | 1.80 | 0.0217 | Serping1; C3; Cd9; Clu; Cp; Ctsk; Eef1a1; Eng; Ereg; Fbrs; Figf; Ghr; Il18bp; Anpep; Man2b1; Mertk; Tnfrsf11b; Pltp; Lgals3bp; S100a4; Cd3; Selp; Serpina3n; Tcn2; Trf; Tpt1; Vegfa; Xdh; Ywhaz; Ace; Aoc3; Apoe; Sdcbp; Twsg1; Sulf2; F13a1; Arhgdia; Spon1; Serpina3f |
| GO:0005788 | Endoplasmic reticulum lumen | 5.36 | 0.0218 | Calu; Cd4; Hspa5; Hsp90b1; Pdia6; Erp44; Sep15 |
| GO:0034663 | Endoplasmic reticulum chaperone complex | 11.33 | 0.0218 | Hspa5; Hsp90b1; Sdf2l1; Pdia6 |
| GO:0031226 | Intrinsic component of plasma membrane | 1.84 | 0.0447 | Adam8; Cacna1d; Calm2; Cav2; Cd22; Cd72; Cd9; Cyba; Dab2; Dlg1; Efna1; Flt1; Ghr; Itga5; Itgav; Laptm5; Tnfrsf11b; Tgfbr2; Tenm4; Slco2a1; Sdcbp; Kcne4; Shisa9; Abcc3; Plxnb2; Slc2a10; Stab1; Stab2; Atp13a3; Atp2c1 |
| GO:0005887 | Integral component of plasma membrane | 1.88 | 0.0458 | Adam8; Cacna1d; Calm2; Cav2; Cd22; Cd72; Cd9; Cyba; Dab2; Dlg1; Flt1; Ghr; Itga5; Itgav; Laptm5; Tnfrsf11b; Tgfbr2; Tenm4; Slco2a1; Sdcbp; Kcne4; Shisa9; Abcc3; Plxnb2; Slc2a10; Stab1; Stab2; Atp13a3; Atp2c1 |
| GO:0044432 | Endoplasmic reticulum part | 2.00 | 0.0494 | Adam10; Calu; Cd4; Cyba; Pigq; Hspa5; Scd1; Sec22b; Hsp90b1; Plgp; Sdf2l1; Spcs2; Cisd2; Magt1; Samd8; Tmx3; Pdia6; Syvn1; Erp44; Sep15; Rpn1; Sptssa; Elovl6; Osbpl8 |

FIG. 22 (cont'd)

Focal adhesion

| Genes | logFC | p-value |
|---|---|---|
| Flt1 | 0.48 | 0.008 |
| Itga5 | 0.46 | 0.006 |
| ItgaV | -0.39 | 0.001 |
| Pip5k1c | 0.57 | 0.001 |
| Pxn | 0.51 | 0.009 |
| Tln1 | 0.50 | 0.001 |
| Vav2 | 1.15 | 0.003 |
| Vwf | 0.75 | 0.001 |
| RhoA | -0.27 | 0.007 |
| Cav2 | -0.57 | 0.006 |
| Figf | -1.33 | 0.007 |
| Ppp1cb | -0.51 | 0.0004 |
| Vega | -0.74 | 0.002 |
| Rap1a | -0.42 | 0.005 |
| Rap1b | -0.36 | 0.008 |

Endocytosis

| Genes | logFC | p-value |
|---|---|---|
| Csf1r | 0.36 | 0.004 |
| Dab2 | 0.37 | 0.007 |
| Flt1 | 0.48 | 0.008 |
| Itga5 | 0.46 | 0.006 |
| ItgaV | -0.39 | 0.001 |
| Pip5k1c | 0.57 | 0.001 |
| Tgfbr2 | 0.35 | 0.009 |
| Mvb12b | 0.68 | 0.001 |
| Dnm3 | 1.79 | 0.007 |
| Arap3 | 0.61 | 0.007 |
| Git1 | 0.70 | 0.004 |
| Agap1 | 0.44 | 0.004 |
| Chmp7 | 0.69 | 0.009 |
| RhoA | -0.27 | 0.007 |
| Cav2 | -0.57 | 0.006 |
| Arfgap3 | 0.55 | 0.005 |
| Capza2 | 0.38 | 0.005 |
| Snx12 | 0.60 | 0.0002 |

FIG.23

| Genes | logFC | adj p-value |
| --- | --- | --- |
| PLTP | 1.04 | 0.007 |
| Stab1 | 1.13 | 0.007 |
| Impad1 | -0.77 | 0.01 |
| Adcy3 | 1.26 | 0.02 |
| Sept2 | -0.58 | 0.03 |
| Lgals3bp | 0.77 | 0.03 |
| Slc4a7 | -0.80 | 0.03 |
| Spcs2 | -0.75 | 0.03 |

FIG.24

| Genes | logFC | p-value |
|---|---|---|
| Cell proliferation | | |
| Ccnd1 | -0.12 | 0.49 |
| Ccnd2 | -0.36 | 0.03 |
| Ccnd3 | 0.78 | 0.02 |
| Cdk4 | -0.06 | 0.82 |
| Cdk6 | 0.09 | 0.72 |
| Migratory egress | | |
| Ntn1 | 0.20 | 0.30 |
| Ccr7 | 0.42 | 0.34 |
| Apoptosis | | |
| Casp3 | -0.43 | 0.19 |
| Casp8 | -0.16 | 0.36 |
| Casp9 | 0.39 | 0.87 |
| Bcl2 | -0.06 | 0.79 |
| Bad | 0.36 | 0.39 |
| Bax | -0.18 | 0.29 |

FIG.25

TARGETING THE INNATE IMMUNE SYSTEM TO INDUCE LONG-TERM TOLERANCE AND TO RESOLVE MACROPHAGE ACCUMULATION IN ATHEROSCLEROSIS

CROSS-REFERENCE TO RELATED APPLICATIONS

This application is a division of U.S. patent application Ser. No. 16/097,013, filed Oct. 26, 2018, which is a U.S. National Stage application, and claims priority of International Application No. PCT/US17/30444, filed May 1, 2017, which claims priority to U.S. Provisional Patent Application No. 62/329,676 filed Apr. 29, 2016. The contents of all of the prior applications are incorporated herein by reference in their entirety.

GOVERNMENT SUPPORT

This invention was made with government support under grants R01 HL118440, R01 HL125703. R01 CA 155432. R01 EB009638, K25 EB016673, and P30 CA008748 awarded by the National Institutes of Health. The government has certain rights in the invention.

FIELD OF THE INVENTION

Methods and compositions for inducing long-term tolerance by hybrid nanoparticles are provided. Compositions and formulations comprising hybrid nanoparticles with inherent affinity for innate immune cells are provided.

BACKGROUND

Indefinite allograft survival remains an elusive goal in organ transplantation. Transplantation requires suppression of the immune system to prevent organ rejection. Patients undergoing organ transplantation usually receive an immunosuppressive drug mixture that includes, but is not limited to, corticosteroids, tacrolimus, cyclosporine and sirolimus (rapamycin)[1-3]. Such immunosuppressive therapy has dramatically improved the short-term results of organ transplantation. However, all immunosuppressive agents have serious adverse effects, such as infections, and considerable metabolic toxicity[4]. There is, consequently, an ongoing need to reduce toxicity derived from chronic immunosuppressive treatment and, by extension, to improve long-term survival. Despite efforts to use currently available immunosuppressive agents in less toxic ways, no alternative regimen has seriously challenged these drugs' almost universal use.

Historically, transplant immunologists have attempted to develop novel tolerogenic protocols by targeting the adaptive immune response mechanism. Such work has been based on the observation that T cells are both necessary and sufficient to induce allograft rejection. However, the induction of transplantation tolerance achieved in murine models cannot be fully explained by mechanisms that target only the adaptive immunity, such as deletion of activated T cells[5-7]. Recent advances in our understanding of how numerous non-specific responses influence immune activity have revealed how the innate immune system (a) reacts to organ transplantation and (b) critically influences the adaptive immune response toward inducing allograft tolerance[8-14]. However, the innate immune system is a potential in vivo therapeutic target that has not been successfully explored in organ transplantation.

Rapamycin is one of the most widely used immunosuppressive drugs in transplantation. This drug blocks T and B lymphocyte activation via mTOR inhibition and efficiently inhibits T cell proliferation[18]. However, use of this drug is associated with severe side effects[19,20], including increased infection susceptibility.

In present treatments, allograft survival requires a cocktail of immunosuppressive drugs. Experimental antibodies targeting the innate immune system have been shown to induce long-term tolerance, with severe side effects.

Thus, there is a need for therapeutics which can modulate the innate immune system and induce long-term tolerance with few side effects.

Atherosclerosis is one of the leading causes of death and disability in the world. Atherosclerosis involves the deposition of fatty plaques on the luminal surface of arteries, which in turn causes stenosis, i.e., narrowing of the artery. Ultimately, this deposition blocks blood flow distal to the lesion causing ischemic damage.

There is still a need to develop more effective therapeutics for atherosclerosis and novel ones which target plaque inflammation.

DESCRIPTION OF THE DRAWINGS

FIGS. 1A-G are diagrams showing an overview of mTOR-HDL nanoimmunotherapy, allograft model, biodistribution and immune cell targeting. FIG. 1A is a diagram showing that mTOR-HDL nanoparticles, synthesized from phospholipids, human APOA1 and rapamycin, had a discoidal shape as evaluated by transmission electron microscopy (TEM) and that they can be radiolabeled with $^{89}$Zr. FIG. 1B is a schematic showing BALB/c donor hearts (H2d) transplanted into fully allogeneic C57BL/6 recipients (H2b) receiving mTOR nanoimmunotherapy, which are either radiolabeled for PET imaging and biodistribution, or fluorescently labeled for distribution among cell subsets of the innate and adaptive immune system. FIG. 1C are representative micro-PET/CT 3D fusion images of mice 24 hours after intravenous administration of mTOR-HDL radiolabeled with $^{89}$Zr ($^{89}$Zr-mTOR-HDL). The CT image was used as anatomical reference to create regions of interest to determine radioactivity concentration in the transplanted heart (3D-movie is provided as S2 A). FIG. 1D is a graph of radioactivity counting showing biodistribution of $^{89}$Zr-mTOR-HDL in tissues of interest (kidney, liver, spleen, blood, bone, skin, and muscle) 24 hours post injection. The radioactivity content was expressed as percentage of injected dose per gram of tissue (% ID/g). Error bars are standard error of the mean (SEM), n=3. FIG. 1E is autoradiography determined radiotracer distribution in native (N) vs. transplanted heart (Tx) at 24 h post-intravenous administration of $^{89}$Zr— mTOR-HDL in the same recipient. Quantification was carried out using Image J software. Error bars are standard deviations (SD), n=3. FIG. 1F are graphical representations of flow cytometry gating strategy to distinguish myeloid cells in blood, spleen and the transplanted heart. Grey histograms show immune cell distribution in the mice injected with DiO-labeled mTOR-HDL compared to control (black histogram). FIG. 1G are graphs showing mean fluorescence intensity (MFI) of neutrophils, monocytes/macrophages, Ly-6C$^{lo}$ and Ly-6C$^{hi}$ monocytes/macrophages, dendritic cells and T cells in the blood, spleen and the transplanted heart is shown. Error bars are standard error of the mean (SEM), n=4; ANOVA *P≤0.05; **p≤0.01.

FIG. 2A are graphs showing total numbers of graft-infiltrating leukocytes, neutrophils, macrophages and dendritic cells. Flow cytometric analysis of different cell subsets in the transplanted heart of placebo, Oral-Ra and mTOR-HDL-treated recipients at day 6 post-transplantation is shown (ANOVA *P≤0.05; **P≤0.01). FIG. 2B are graphical representations showing frequency of Ly-6C$^{hi}$ vs. Ly6C$^{lo}$ macrophages in the transplanted heart from placebo, Oral-Ra and mTOR-HDL-treated recipients are shown. Data represents mean±SEM; n=4 per group. ANOVA *P≤0.05; **P≤0.01. FIG. 2C displays images of GSEA gene array analysis. Results indicate that the mTOR pathway is down-regulated in Ly-6C$^{lo}$ intra-graft macrophages from mTOR-HDL treated recipients. Heatmaps derived from the GSEA data of selected genes that achieve p <0.05 in Ly-6C$^{lo}$ macrophages from the allografts of mTOR-HDL treated recipients at day 6 post-transplantation are shown (means of n=3 per group).

FIG. 3A are images showing functional characterization of graft-infiltrating Ly-6C$^{lo}$ and Ly-6C$^{hi}$ MΦ and Ly-6G neutrophils from placebo and mTOR-HDL treated mice 6 days post-transplantation. Representative and quantitative flow cytometry results for Ly-6C and Ly-6G expression in CD45$^+$ CD11b$^+$ allografts, myeloid cell subsets from the placebo and mTOR-HDL-treated allograft recipients (top). In vitro suppressive capacity of graft-infiltrating Ly-6C$^{lo}$ MΦ from placebo and mTOR-HDL-treated mice was measured. Quantitative flow cytometry results for CFSE CD8$^+$ T cells, with cell proliferation percentage measured by CSFE dilution after 72 hours are shown (middle). In vitro T-reg expansion capacity of graft-infiltrating Ly-6Clo MΦ from placebo and mTOR-HDL-treated mice was evaluated. Flow cytometric analysis indicates percentage of Foxp3 expression on CD4+ T cells after co-culture for 72 hours (bottom). Data are shown as mean±SEM; n=4 per group; t-test P≤0.01. FIG. 3B are images showing percentage of graft-infiltrating CD4$^+$CD25$^+$ vs. CD4$^+$CD25$^-$ T-cells from placebo and mTOR-HDL-treated allograft recipients. Data are shown as mean±SEM; n=4 per group; t-test P≤0.01. FIG. 3C are scatter plots and graphs showing phenotypic characterization of graft-infiltrating Ly-6C$^{lo}$ and Ly-6C$^{hi}$ MΦ and Ly-6G neutrophils, at day 6 post-transplantation, from mTOR-HDL-treated mice following Ly-6Clo MΦ depletion. Representative and quantitative flow cytometry results of graft-infiltrating CD45$^+$CD11b$^+$ myeloid cell subsets of mTOR-HDL-treated CD169-DTR recipients receiving DT for Ly-6Clo MΦ depletion. Data are shown as mean±SEM; n=4 per group; t-test P≤0.01. FIG. 3D is a Kaplan-Meier curve showing graft survival following Ly-6C$^{lo}$ macrophage depletion in mTOR-HDL treated recipients. Results indicate that adoptive transfer of wild type monocytes restore tolerance in mTOR-HDL treated macrophage depleted recipients (n=4 mice in each group; Kaplan-Meier P≤0.01). FIG. 3E is a box-plot of the gene array for the expression of CD40 in Ly-6C$_{lo}$ macrophages obtained from the allografts of placebo versus mTOR-HDL treated recipients (means of n=3 per group; t-test P≤0.01). FIG. 3F is a Kaplan-Meier curve showing graft survival of mTOR-HDL recipients receiving agonistic stimulatory CD40 mAb in vivo with or without TRAF6i-HDL nanoimmunotherapy (n=5 mice in each group; Kaplan-Meier P≤0.01). FIG. 3G is a Kaplan-Meier curve showing graft survival curves of placebo, Oral-Ra, mTOR-HDL and mTOR-HDL/TRAF6i-HDL combination therapy (n=8 mice in each group, Kaplan-Meier survival analysis; P≤0.001 placebo vs. mTOR-HDL, P≤0.01 Oral-Ra vs. mTOR-HDL, P≤0.01 TRAF6i-HDL vs. mTOR-HDL/RAF6i-HDL, P≤0.01 mTOR-HDL vs. mTOR-HDL/TRAF6i-HDL).

FIG. 5A shows representative near infrared fluorescence images (NIRF) of organs injected with either PBS control (first row of organs) or DiR-labeled mTOR-HDL 24 hours before transplantation show accumulation in liver, spleen, lung, kidney, heart and muscle. The right panel is a graph with bars representing the control to mTOR-HDL-DiR accumulation ratio in each organ, calculated by dividing the total signal of each organ in the control and mTOR-HDL-DiR groups. Error bars are standard error of the means (SEM.), n=4; *P≤0.05; P≤0.01, *P≤0.001. FIG. 5B is a graph showing myeloid cell distribution in blood and spleen. Grey histograms (right) show distribution in mice injected with DiO-labeled mTOR-HDL compared to distribution in control animals (black histogram). FIG. 5C are graphs showing mean fluorescence intensity (MFI) of neutrophils, monocyte/macrophage pool. Ly-6Clo/Ly-6Chi monocytes and dendritic cells in blood and spleen. Error bars are standard error of the means (SEM.), n=4; *P≤0.05; **P≤0.01.

FIG. 7A is scatter plot showing flow cytometry gating strategy to distinguish T cells in blood and the transplanted heart. Grey histograms (right) show the T cell distribution in mice injected with DiO-labeled mTOR-HDL compared to distribution in control animals (black histogram). FIG. 7B are graphs showing mean fluorescence intensity (MFI) of monocytes/macrophages, CD3$^+$ T, CD4$^+$ T and CD8$^+$ T-cells in blood and the transplanted heart. Error bars are standard error of the mean (SEM.), n=4; P≤0.01; *P≤0.001.

FIG. 9B are graphs showing a ratio of Ly-6C$^{hi}$ to Ly-6C$^{lo}$ monocytes in the blood, spleen and transplanted hearts of placebo, Oral-Ra and mTOR-HDL-treated allograft recipients. Data are shown as mean±SEM; n=4 per group; *P≤0.05; **P≤0.01.

FIG. 11B shows that the disc shape of the TRAF6i-HDL particles can be appreciated when particles are in stacked formation, while the size of the nanoparticles can be evaluated when observing particles from a top down perspective.

FIG. 12A are images showing skin allograft rejection in control and mTOR-HDL-treated mice at different time points post-transplantation, as documented by a microscope with a digital camera. FIG. 12B is a Kaplan-Meier curve of skin allografts (n=4 mice in each group, P≤0.01 between Placebo and mTOR-HDL).

In FIG. 13B the representative images of IHC for H&E and Sirius Red show no signs of chronic allograph vasculopathy (CAV). Heart allografts from mTor-HDL/TRAFi-HDL treated recipients were collected at dat 100 after transplantation (n=4; magnification X200). For FIG. 13B, the chronic allograft vasculopathy analysis, the sections show mild cicumferential inflammation without arteritis and no signs of intimal hyperplasia. Mouse aortic segments did not exhibit any histological alteration with no intimal thickening, and no signs of CAV.

FIG. 14A is a schematic representation of TRAF6i-HDL, which was created by combining human apoA-I, lipids (DMPC and MHPC) and a small molecule inhibitor of the CD40-TRAF6 interaction. FIG. 14B is a study overview showing the subsequent steps that were taken to investigate TRAF6i-HDL. FIG. 14C is a graph showing pharmacokinetics of $^{89}$Zr-labeled TRAF6i-HDL in Apoe-\— mice, showing the blood decay curve (left panel) and whole body 3D-rendered PET/CT fusion image at 24 hours post administration (right panel) showing the highest uptake in the liver, spleen and kidneys. FIG. 14D is a graph of gamma counting of the distribution of $^{89}$Zr-labeled TRAF6i-HDL at 24 hours post administration. Autoradiography of the aorta shows visible TRAF6i-HDL accumulation in the aortic root, which is the preferential location of atherosclerosis development in the mouse model. FIG. 14E shows NIRF imaging of DiR-labeled TRAF6i-HDL distribution in mouse aorta (n=2), and corresponding graphs showing accumulation of TRAF6i-HDL in the aortic mot area. FIG. 14F are flow cytometry data of whole mouse aortas (n=8) with DiO-labeled TRAF6i-HDL showing high targeting efficiency of macrophages and Ly6C$^{hi}$ monocytes, while lineage positive CD11b negative cells did not take up nanoparticles. *** p<0.001. FIG. 14G are images of flow cytometry analysis of bone marrow, blood, spleen and aorta cells, showing that Ly6C$^{hi}$ monocytes and macrophages took up DiO labeled TRAF6i-HDL. Neutrophils, Ly6C$^{lo}$ monocytes and dendritic cells also took up DiO-TRAF6i-HDL, while lineage positive cells (all non-myeloid cells) did not. Bars represent the standard error of the mean.

FIG. 15A are images and graphs of aortic roots showing no difference in plaque size (H&E), collagen content (Sirius Red), or number of proliferating cells (Ki67 staining) between the treatment groups. FIG. 15B are images and graphs showing Mac3 staining of aortic roots illustrating a marked decrease in macrophage positive area and a lower macrophage to collagen ratio.  p<0.01, and * p<0.001.

FIG. 16A are images and a graph of FMT/CT imaging showing markedly decreased protease activity in the aortic root in the TRAF6i-HDL (n=7) as compared to the placebo (n=8) treated group. FIG. 16B are images of flow cytometry analysis of whole aortas shows a significant reduction in the number of macrophages in the TRAF6i-HDL (n=27) treated group, compared to placebo (n=27) and rHDL (n=26). The fact that Ly6Chi monocytes are also markedly reduced in the TRAF6i-HDL group indicates impairment of Ly6Chi monocyte recruitment. FIG. 16C are images and graphs of flow cytometry analysis of bone marrow, blood and spleen showed that the decrease in plaque Ly6C$^{hi}$ monocyte content could not be attributed to systemic decreases in Ly6C$^{hi}$ monocytes. (FIG. 16D are images of in vivo BrdU incorporation experiments showing no effect of TRAF6i-HDL on plaque macrophage proliferation. FIG. 16E are graphs from in vitro experiments (n=3) of BrdU incorporation in RAW 264.7 macrophages treated for 24 hours, with either placebo, rHDL. TRAF6i-HDL, bare CD40-TRAF6 small molecule inhibitor or a combination of rHDL+bare CD40-TRAF6 small molecule inhibitor, showed no effect on macrophage proliferation.  p<0.01, and *p<0.001.

FIG. 17A is a Volcano plot, showing the distribution of differentially expressed (DE) genes in plaque monocytes/macrophages. FIG. 17B is a graph showing the total number of significantly up- and down-regulated genes, according to cut-off values of an FDR threshold of 0.2. The FDR<0.2 corresponds to a p-value <0.009. (FIG. 17C shows the gene enrichment analysis of the DE gene set within the gene ontology (GO) database, showing 15 GO terms that are significantly enriched with DE genes. FIG. 17D is a schematic representation of a macrophage showing two significantly altered pathways (focal adhesion and endocytosis) identified by mapping the 416 DE genes with the Kyoto Encyclopedia of Genes and Genomes (KEGG) pathway tool. Also depicted are the 8 most significant DE genes with FDR<0.05 and their location inside the cell (darker black genes are up-regulated, lighter gray genes are down-regulated, the genes are listing in FIGS. 23-24).

FIG. 18 A are graphs of complete blood counts showing no effects of TRAF6i-HDL therapy on lymphocytes, erythrocytes and platelets. FIG. 18B are graphs of extensive blood chemistry analysis showing no toxic effects of TRAF6i-HDL infusion on hepatic, renal, pancreatic or muscle cell biomarkers. Lipids, glucose, protein (albumin and globulin) and electrolytes were also unaffected. FIG. 18C are images of specimens from liver, kidneys and spleen that were sectioned and stained (H&E) for histological analysis and evaluated by a pathologist. No signs of tissue damage or disturbances in tissue architecture were found in any of the tissues.

FIG. 19A are dynamic PET images at 1, 5, 15, 30 and 60 minutes. Images are split up to visualize liver and other organs separately. The graph shows the quantified uptake in the represented organs at the different time points. The rotating image on the right shows a 3D representation of the distribution at 60 min. FIG. 19B are additional static PET/MR images at 24, 48 and 72 hours show the distribution and accumulation of TRAF6i-HDL. The graph shows the quantified uptake in the represented organs at the different time points. FIG. 19C includes graphs and images reflecting gamma counting distribution in NHPs at 24 and 72 hours post administration of $^{89}$Zr-TRAF6i-HDL. FIG. 19D is a graph showing blood time-activity curve for 89Zr-TRAF6i-HDL in NHPs.

FIG. 20 is a table showing complete blood count values of placebo. HDL and TRAF6i-HDL treated Apoe−/− mice. P-values were calculated with Kruskal Wallis tests.

FIG. 21 is a table showing blood chemistry values of placebo and TRAF6i-HDL treated Apoe−/− mice. P-values were calculated by Mann Whitney t tests. No significant differences between any of the groups were observed, except for a minor increase in alkaline phosphatase.

FIG. 22 is a table showing differential expression of genes in Gene Ontology terms. CD68 positive cells from aortic sinus plaques of Apoe−/− mice were isolated by laser capture microdissection. 15 GO terms showed enrichment with differential expressed genes. P-values are shown as adjusted p-values.

FIG. 23 is a table showing differential expression of genes in two main identified KEGG pathways. CD68 positive cells from aortic sinus plaques of Apoe−/− mice were isolated by laser capture microdissection. Differential expression of genes in two significant KEGG pathways. Focal adhesion and Endocytosis, between placebo and TRAF6i-HDL treated Apoe−/− mice. P-values are shown as unadjusted p-values.

FIG. 24 is a table showing differential expression of genes with FDR<0.05. CD68 positive cells from aortic sinus plaques of Apoe−/− mice were isolated by laser capture microdissection. Differential expression of genes between placebo and TRAF6i-HDL treated Apoe−/− mice are shown. P-values are shown as adjusted p-values.

FIG. 25 is a table showing differential expression of genes involved in proliferation, apoptosis and migratory egress. CD68 positive cells from aortic sinus plaques of Apoe−/− mice were isolated by laser capture microdissection. Differential expression of genes between placebo and TRAF6i-HDL treated Apoe−/− mice are shown. Unadjusted p values are shown.

SUMMARY

Figure 1A:
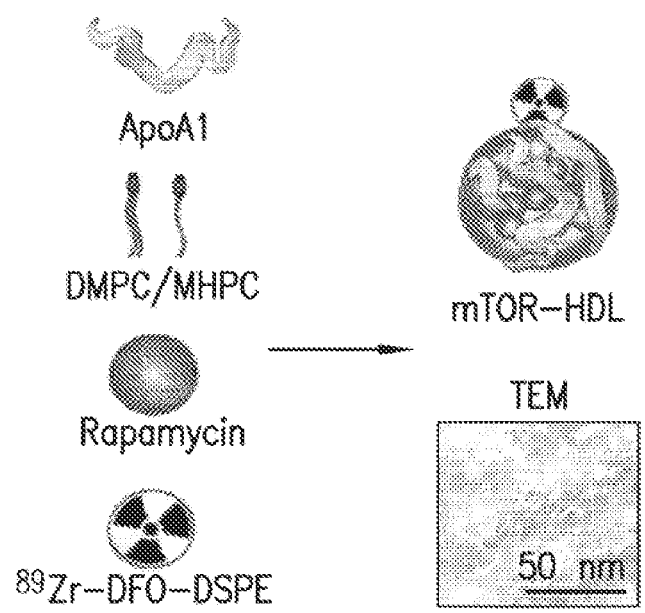

Encompassed by the present disclosure is a method for prolonging allograft survival in a patient, the method comprising administering an effective amount of the present composition to a patient in need thereof.

The present disclosure provides for a method for decreasing dendritic cell stimulatory capacity in a patient, comprising administering an effective amount of the present composition to a patient in need thereof.

The present disclosure provides for a method for promoting the development of regulatory macrophages in a patient, comprising administering an effective amount of the present composition to a patient in need thereof.

The present disclosure provides for a method of inducing transplant tolerance in a patient comprising administering an effective amount of the present composition to a patient in need thereof.

The present disclosure provides for a method of targeting myeloid cells in a patient comprising administering an effective amount of the present composition to a patient in need thereof, wherein the mTOR-HDL reduces Mo/MΦ numbers in the circulation of the patient.

In certain embodiments, the present composition specifically targets myeloid cells.

In certain embodiments, the patient has undergone a transplant and the transplanted tissue is lung tissue, heart tissue, kidney tissue, liver tissue, retinal tissue, corneal tissue, skin tissue, pancreatic tissue, intestinal tissue, genital tissue, ovary tissue, bone tissue, tendon tissue, bone marrow, or vascular tissue. In certain embodiments, the transplanted tissue is an intact organ.

In certain embodiments, the patient has received an allogeneic tissue or organ transplant. In certain embodiments, the present method is performed prior to performance of an allogeneic tissue or organ transplant. In certain embodiments, the method is performed in conjunction with an allogeneic tissue or organ transplant. In certain embodiments, the method is performed within at least two weeks after an allogeneic tissue or organ transplant.

In certain embodiments, the subject or patient is human.

In certain embodiments, the composition is administered intravenously or intra-arterially.

In certain embodiments, the present method further comprises administering to the patient one or more immunosuppressant agents, such as cyclosporine A or FK506.

The present disclosure provides for a method of inducing immune tolerance comprising administering to a patient an effective amount of (i) a composition comprising a high-density lipoprotein-derived nanoparticle (HDL) which comprises an mTOR inhibitor, and optionally (ii) a composition comprising a high-density lipoprotein-derived nanoparticle (HDL) which comprises a CD40-TRAF6 inhibitor. In certain embodiments, the mTOR inhibitor is rapamycin or a pharmaceutically acceptable salt, solvate, poly-morph, tautomer or prodrug thereof, formulated as rapamycin nanoparticle (mTOR-HDL). In certain embodiments, the CD40-

TRAF6 inhibitor is 6877002 or a pharmaceutically acceptable salt, solvate, poly-morph, tautomer or prodrug thereof, formulated as TRAF6i-HDL nanoparticle.

In certain embodiments, the administration promotes Ly-6C$^{lo}$ M/M development.

In certain embodiments, the patient has an autoimmune condition selected from the group consisting of coeliac disease, type 1 diabetes, multiple sclerosis, thyroiditis, Grave's disease, systemic lupus erythematosus, scleroderma, psoriasis, arthritis, rheumatoid arthritis, alopecia great a, ankylosing spondylitis, Churg-Strauss Syndrome, autoimmune hemolytic anemia, autoimmune hepatitis, Behcect's disease, Crohn's disease, dermatomyositis, glomerulonephritis, Guillain-Barre syndrome, irritable bowel disease (IBD), lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis, in certain embodiments, the patient is susceptible to or has an atherosclerotic condition including: coronary atherosclerosis, diabetic atherosclerosis, a sequela of atherosclerosis, such as acute coronary syndrome, myocardial infarction, angina pectoris, peripheral vascular disease, intermittent claudication, myocardial ischemia, stroke, heart failure and combinations thereof.

The present disclosure provides for a method of treating atherosclerosis, the method comprising administering to a patient an effective amount of a composition comprising a high-density lipoprotein-derived nanoparticle (HDL) which comprises a CD40-TRAF6 inhibitor. In certain embodiments, the CD40-TRAF6 inhibitor is 6877002 or a pharmaceutically acceptable salt, solvate, poly-morph, tautomer or prodrug thereof, formulated as TRA mi-HDL nanoparticle.

In certain embodiments, the present method further comprises administering to the patient an effective amount of a composition comprising a high-density lipoprotein-derived nanoparticle (HDL) which comprises an mTOR inhibitor. In certain embodiments, the mTOR inhibitor is rapamycin or a pharmaceutically acceptable salt, solvate, poly-morph, tautomer or prodrug thereof, formulated as rapamycin nanoparticle (mTOR-HDL). In certain embodiments, the HDL comprises 1,2-dimyristoyl-sn-glycero-3-phosphatidylcholine (DMPC) and 1-myristoyl-2-hydroxy-sn-glycero-phosphocholine (MHPC) and further comprises ApoA-1.

In certain embodiments, atherosclerosis includes: coronary atherosclerosis, diabetic atherosclerosis, a sequela of atherosclerosis, such as acute coronary syndrome, myocardial infarction, angina pectoris, peripheral vascular disease, intermittent claudication, myocardial ischemia, stroke, heart failure and combinations thereof.

The present disclosure provides for a method of targeting macrophages and/or monocytes in a plaque or a vascular inflammatory site, the method comprising administering to a patient an effective amount of a composition comprising a high-density lipoprotein-derived nanoparticle (HDL) which comprises a CD40-TRAF6 inhibitor. In certain embodiments, the CD40-TRAF6 inhibitor is 6877002 or a pharmaceutically acceptable salt, solvate, poly-morph, tautomer or prodrug thereof, formulated as TRAF6i-HDL nanoparticle.

In certain embodiments, the present method further comprises administering to the patient an effective amount of a composition comprising a high-density lipoprotein-derived nanoparticle (HDL) which comprises an mTOR inhibitor. In certain embodiments, the mTOR inhibitor is rapamycin or a pharmaceutically acceptable salt, solvate, poly-morph, tautomer or prodrug thereof, formulated as rapamycin nanoparticle (mTOR-HDL). In certain embodiments, the HDL comprises 1,2-dimyristoyl-sn-glycero-3-phosphatidylcholine (DMPC) and 1-myristoyl-2-hydroxy-sn-glycero-phosphocholine (MHPC) and further comprises ApoA-1.

The present disclosure provides for a method for prophylaxis of organ or tissue rejection, the method comprising the step of administering to a patient in need thereof an effective amount of a composition comprising a high-density lipoprotein-derived nanoparticle (HDL) which comprises an mTOR inhibitor. In certain embodiments, the mTOR inhibitor is rapamycin or a pharmaceutically acceptable salt, solvate, poly-morph, tautomer or prodrug thereof, formulated as rapamycin nanoparticle (mTOR-HDL). In certain embodiments, the HDL comprises 1,2-dimyristoyl-sn-glycero-3-phosphatidylcholine (DMPC) and 1-myristoyl-2-hydroxy-sn-glycero-phosphocholine (MHPC) and further comprises ApoA-1.

In certain embodiments, the patient has undergone an organ or tissue transplant and the transplanted tissue is lung tissue, heart tissue, kidney tissue, liver tissue, retinal tissue, corneal tissue, skin tissue, pancreatic tissue, intestinal tissue, genital tissue, ovary tissue, bone tissue, tendon tissue, bone marrow, or vascular tissue.

In certain embodiments, the composition is administered intravenously or intra-arterially.

In certain embodiments, the present method further comprises administering to the patient one or more immunosuppressant agents.

Also encompassed by the present disclosure is a method for slowing the progression of atherosclerosis, the method comprising the step of administering to a patient in need thereof an effective amount of a composition comprising a high-density lipoprotein-derived nanoparticle (HDL) which comprises a CD40-TRAF6 inhibitor. In certain embodiments, the CD40-TRAF6 inhibitor is 6877002 or a pharmaceutically acceptable salt, solvate, poly-morph, tautomer or prodrug thereof, formulated as TRAF6i-HDL, nanoparticle. In certain embodiments, the HDL comprises 1,2-dimyristoyl-sn-glycero-3-phosphatidylcholine (DMPC) and 1-myristoyl-2-hydroxy-sn-glycero-phosphocholine (MHPC) and further comprises ApoA-1.

The present disclosure provides for a composition comprising a high-density lipoprotein-derived nanoparticle (HDL) which comprises an m-TOR inhibitor. In certain embodiments, the HDL comprises 1,2-dimyristoyl-sn-glycero-3-phosphatidylcholine (DMPC) and 1-myristoyl-2-hydroxy-sn-glycero-phosphocholine (MHPC) and further comprises ApoA-1. In certain embodiments, the weight ratio of DMPC to MHPC is about 3:1. In certain embodiments, the mTOR inhibitor is rapamycin or a pharmaceutically acceptable salt, solvate, poly-morph, tautomer or prodrug thereof, formulated as rapamycin nanoparticle (mTOR-HDL or rapamycin-HDL).

In certain embodiments, the pharmaceutical composition further comprises one or more immunosuppressive agents or anti-inflammatory agent. In certain embodiments, the immunosuppressant agent is cyclosporine A or FK506.

Also encompassed by the present disclosure is a composition comprising a high-density lipoprotein-derived nanoparticle (HDL) which comprises a CD40-TRAF6 inhibitor. In certain embodiments, the HDL comprises 1,2-dimyristoyl-sn-glycero-3-phosphatidylcholine (DMPC) and 1-myristoyl-2-hydroxy-sn-glycero-phosphocholine (MHPC) and further comprises ApoA-1. In certain embodiments, the weight ratio of DMPC to MHPC ranges from about 8:1 to about 9:1. In certain embodiments, the CD40-TRAF6 inhibitor is 6877002, or a pharmaceutically acceptable salt, solvate, poly-morph, tautomer or prodrug thereof, formulated as TRAF6i-HDL nanoparticle.

The present disclosure also provides for a pharmaceutical composition comprising a) pharmaceutically effective amount of the present composition, and b) a pharmaceutically acceptable carrier, diluent, excipient and/or adjuvant.

The present disclosure provides for a pharmaceutical composition comprising a) a composition comprising a high-density lipoprotein-derived nanoparticle (HDL) which comprises an m-TOR inhibitor, and b) a composition comprising a high-density lipoprotein-derived nanoparticle (HDL) which comprises a CD40-TRAF6 inhibitor.

The present disclosure provides for a kit comprising the present composition. In certain embodiments, the m-TOR inhibitor is rapamycin. In certain embodiments, the kit further comprises one or more immunosuppressive agents, such as cyclosporine A, FK506 or rapamycin. In certain embodiments, the CD40-TRAF6 inhibitor is 6877002.

The present disclosure provides for use of a high-density lipoprotein-derived nanoparticle (HDL) which comprises an mTOR inhibitor, and optionally (ii) a high-density lipoprotein-derived nanoparticle (HDL) which comprises a CD40-TRAF6 inhibitor, in the preparation of a composition for inducing immune tolerance.

The present disclosure provides for use of a high-density lipoprotein-derived nanoparticle (HDL) which comprises a CD4-TRAF6 inhibitor, in the preparation of a composition for treating atherosclerosis.

The present disclosure provides for use of a high-density lipoprotein-derived nanoparticle (HDL) which comprises a CD40-TRAF6 inhibitor, in the preparation of a composition for targeting macrophages and/or monocytes in a plaque or a vascular inflammatory site.

The present disclosure provides for use of a high-density lipoprotein-derived nanoparticle (HDL) which comprises an mTOR inhibitor, in the preparation of a composition for prophylaxis of organ or tissue rejection.

The present disclosure provides for use of a high-density lipoprotein-derived nanoparticle (HDL) which comprises a CD40-TRAF6 inhibitor, in the preparation of a composition for slowing the progression of atherosclerosis.

The present disclosure provides for use of the present nanoparticles in the preparation of a composition for prolonging allograft survival in a patient in need thereof.

The present disclosure provides for use of the present nanoparticles in the preparation of a composition for decreasing dendritic cell stimulatory capacity in a patient in need thereof.

The present disclosure provides for use of the present nanoparticles in the preparation of a composition for promoting the development of regulatory macrophages in a patient in need thereof.

The present disclosure provides for use of the present nanoparticles in the preparation of a composition for inducing transplant tolerance in a patient in need thereof.

The present disclosure provides for use of the present nanoparticles in the preparation of a composition for targeting myeloid cells in a patient in need thereof. In certain embodiments, the mTOR-HDL reduces Mo/MΦ numbers in the circulation of the patient.

DETAILED DESCRIPTION

A high-density lipoprotein-derived nanoparticle (HDL) has been developed to deliver rapamycin to innate immune cells. A hybrid HDL nanoparticle, named Rapamycin-HDL (an exemplary mTOR-HDL), which encapsulates rapamycin in a corona of natural phospholipids and apolipoprotein A-1 (APOA1) was developed to prolong allograft survival. HDL-nanoparticles contain APOA1, which efficiently bind to macrophages cells through the scavenger receptor type B-1 (sr-b1) and adenosine triphosphate-binding cassette transporter A1 (ABCA1)[21,22]. As a result, mTOR-HDL nanoparticles specifically deliver rapamycin to innate immune cells in vivo, mTOR-HDL nanoparticles, ~15 nm in diameter, had a high rapamycin encapsulation efficiency of ~65%. Radiolabeled mTOR-HDL was observed to specifically accumulate in the transplanted heart and to be mainly associated with myeloid cells. The results demonstrate a significant reduction of Ly-6$C^{hi}$/Ly-6$C^{low}$ as well as CD25/CD25[4] cells in the transplanted heart. This treatment also resulted in a dramatic enhancement of allograft survival.

Additionally, the inventors developed an HDL nonbiologic that incorporates a small molecule inhibitor (TRAF-STOP) directed against the binding domain of CD40 on TRAF6 (referred to hereafter as TRAF6i-HDL). The 6877002 inhibitor was used for the development of this TRAF6i-HDL (the 6877002 inhibitor is described in Chatzigeorgiou et al. 2014, and also U.S. Pat. No. 9,408,829, as well as other inhibitors). The TRAF6i-HDL nanoparticles had a mean hydrodynamic radius of 19.2 t 3.1 nm and a drug incorporation efficiency of 84.6±8.6%. The TRAF6i-HDL nanoparticles can be used alone or in combination with the mTOR-HDL nanoparticles described herein.

In alternative embodiments, other CD40-TRAF6 inhibitors such as SMI 6860766 (described in Van der Berg et al 2015) can be used to form alternative TRAF6i-HDLs. These inhibitors can be used alone or in combination with any of the other nanobiologics as described herein. Additional suitable compounds for blocking the CD40-TRAF6 interaction are described in U.S. Pat. No. 9,408,829.

Using an experimental heart transplantation model in combination with molecular imaging and immunological techniques, the present data demonstrate that mTOR-HDL restricts dendritic cells' potent stimulatory capacity, promotes the development of regulatory macrophages, and prolongs heart allograft survival indefinitely. The regimen comprised only three intravenous tail vein injections of 5 mg/kg equivalent rapamycin during the first week after transplantation. Using a combination of in vivo positron emission tomography with computed tomography (PET-CT) imaging and an array of immunological assays, we evaluated heart allograft targeting and cellular specificity. We subsequently and extensively studied innate immune response, allograft survival and therapeutic mechanisms. Our data demonstrate that mTOR-HDL nanoparticle treatment promotes indefinite heart allograft survival. Additionally, the inventors were able to extend these results in a skin transplant model. These results provide critical information about how to manipulate the immune response toward inducing donor-specific non-response in the clinic and identify new therapeutic targets that may prevent allograft rejection in humans.

Furthermore, the present data demonstrate that a short-term therapeutic treatment with mTOR-HDL in combination with an inhibitory CD40-TRAF6 specific nanoimmunotherapy (TRAF6i-HDL) synergistically promote organ transplant acceptance leading to indefinite allograft survival.

Together, the results demonstate that HDL-based nanotherapy represents an effective treatment paradigm for the induction of transplantation tolerance. This study provides the foundation for developing novel therapeutic nanomedicinal compounds and treatments that generate tolerance-inducing immune regulatory macrophages. Additionally, the TRAF6i-HDL treatment has been shown to solve macrophage accumulation in atherosclerosis and to exhibit a desirable safety and efficacy profile in non-human primates.

Definitions and Methods

In certain embodiments, compositions of the present invention include a high-density lipoprotein-derived nanoparticle (HDL) which comprises an m-TOR inhibitor (indicated as mTOR-inhibitor-HDL), wherein an example of such as m-TOR inhibitor is rapamycin or a pharmaceutically acceptable salt, solvate, poly-morph, tautomer or prodrug thereof, formulated as rapamycin nanoparticle tan exemplary mTOR-HDL). In alternative embodiments, the composition may comprise one or more rapamycin derivatives and potential targets of the rapamycin signaling cascade (S6K).

In certain embodiments, the composition may further comprise a pharmaceutically acceptable carrier, diluent, excipient and/or adjuvant.

In certain embodiments, the HDL composition can be administered in combination with one or more additional immunosuppressive agents such as cyclosporine A, FK506, or azathioprine, mycophenolate mofetil, and any analogues thereof (e.g., everolimus, ABT-578, CCI-779, and AP23573).

In an embodiment. "patient" or "subject" refers to mammals and includes human and veterinary subjects. In an embodiment, the subject is mammalian.

In an embodiment, the compound is administered in a composition comprising a pharmaceutically acceptable carrier.

In certain embodiments, the invention relates to a method of the treatment or prophylaxis of a disorder or disease mediated by allograft rejection, comprising administering to a patient in need thereof a therapeutically effective amount of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or the pharmaceutical composition thereof. In an embodiment, the subject is at risk for allograft rejection and the method is for preventing (i.e., prophylaxis) or inhibiting allograft rejection.

Additionally, since any transplant is at risk of rejection, embodiments include adjuvant therapy using any of the methods or compositions described herein to prevent any transplant rejection.

Diseases mediated by allograft rejection include, but are not limited to heart transplant, skin transplant, liver transplant, lung transplant, bronchiolitis-obliterans syndrome (BOS), kidney transplant, pancreas transplant, pancreatic islets transplant, intestinal transplant, bone transplant, retinal transplant, bone marrow transplant, islet transplantation and corneal transplant. In certain embodiments, treatments are facilitated by administering mTOR-HDL In other embodiments, treatments are facilitated by administering a combination of mTOR-HDL and TRAF6i-HDL, either in a single HDL or in two separate HDL compositions.

In certain embodiments, the invention relates to a method of the treatment or prophylaxis of a disorder or disease mediated by allograft rejection, comprising administering to a patient in need thereof a therapeutically effective amount of a (i) high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or the pharmaceutical composition thereof and optionally (ii) TRAFi-HDL nanoparticles which comprise a CD40-TRAF6 inhibitor, wherein the CD40-TRAF6 inhibitor is 6877002, or a pharmaceutically acceptable salt, solvate, poly-morph, tautomer or prodrug thereof, formulated as an HDL nanoparticle (TRAFi-HDL), or the pharmaceutical composition thereof. In certain embodiments, the mTOR-HDL and TRAFi-HDL nanoparticles are administered in combination, or in sequence to a patient in need thereof. In an embodiment, the subject is at risk for allograft rejection and the method is for preventing (i.e., prophylaxis) or inhibiting allograft rejection. Diseases mediated by allograft rejection include, but are not limited to heart transplant, skin transplant, liver transplant, lung transplant, bronchiolitis-obliterans syndrome (BOS), kidney transplant, pancreas transplant, pancreatic islets transplant, intestinal transplant, bone transplant, retinal transplant, and corneal transplant.

In additional embodiments, the invention relates to a method of treatment or prophylaxis of an autoimmune disease. Examples of autoimmune disease include coeliac disease, type 1 diabetes, multiple sclerosis, thyroiditis, Grave's disease, systemic lupus erythematosus, scleroderma, psoriasis, arthritis, rheumatoid arthritis, alopecia greata, ankylosing spondylitis, Churg-Strauss Syndrome, autoimmune hemolytic anemia, autoimmune hepatitis, Behcet's disease, Crohn's disease, dermatomyositis, glomerulonephritis, Guillain-Barre syndrome, IBD, lupus nephritis, myasthenia gravis, myocarditis, pemphigus/pemphigoid, pernicious anemia, polyarteritis nodosa, polymyositis, primary biliary cirrhosis, rheumatic fever, sarcoidosis, Sjogren's syndrome, ulcerative colitis, uveitis, vitiligo, and Wegener's granulomatosis.

Conditions that may also be treated using the present compositions and methods include diseases which are associated with increased inflammation. Schwarz et al., Identification of differentially expressed genes induced by transient ischemic stroke, Brain Res Mol Brain Res. 2002; 101(1-2):12-22.

The present compositions and methods may be used to treat or prevent a cardiovascular disease, such as atherosclerosis, stenosis, restenosis, hypertension, heart failure, left ventricular hypertrophy (LVH), myocardial infarction, acute coronary syndrome, stroke, transient ischemic attack, impaired circulation, heart disease, cholesterol and plaque formation, ischemia, ischemia reperfusion injury, peripheral vascular disease, myocardial infection, cardiac disease (e.g, risk stratification of chest pain and interventional procedures), cardiopulmonary resuscitation, kidney failure, thrombosis (e.g., venous thrombosis, deep vein thrombosis, portal vein thrombosis, renal vein thrombosis, jugular vein thrombosis, cerebral venous sinus thrombosis, arterial thrombosis, etc.), thrombus formation, thrombotic event or complication, Budd-Chiari syndrome, Paget-Schroetter disease, coronary heart disease, coronary artery disease, need for coronary revascularization, peripheral artery disease, a pulmonary circulatory disease, pulmonary embolism, a cerebrovascular disease, cellular proliferation and endothelial dysfunction, graft occlusion or failure, need for or an adverse clinical outcome after peripheral bypass graft surgery, need for or an adverse clinical outcome after coronary artery bypass (CABG) surgery, failure or adverse outcome after angioplasty, internal mammary artery graft failure, vein graft failure, autologous vein grafts, vein graft occlusion, ischemic diseases, intravascular coagulation, cerebrovascular disease, or any other cardiovascular disease related to obesity or an overweight condition.

Any type of atherosclerotic lesion may be treated, such as coronary atherosclerosis, diabetic atherosclerosis, atherosclerosis and its sequelae (e.g., acute coronary syndrome, myocardial infarction, angina pectoris, peripheral vascular disease, intermittent claudication, myocardial ischemia, stroke, heart failure, etc.).

In certain embodiments, hydrophobicity of a compound (e.g., rapamycin, or any compound described herein) can be modified by adding a long alkyl chain to the molecule.

The compounds used in the methods of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474. (1997) JUPAC. In cases in which compounds have unsaturated carbon-carbon double bonds, both the cis (Z) and trans (F) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in *Enantiomers. Racemates and Resolutions* by J. Jacques. A. Collet and S. Wilen, Pub. John Wiley & Sons, NY, 1981. For example, the resolution may be carried out by preparative chromatography on a chiral column.

The subject invention is also intended to include use of all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include carbon-13 and carbon-14.

It will be noted that any notation of a carbon in structures throughout this application, when used without further notation, are intended to represent all isotopes of carbon, such as $^{12}C$, $^{13}C$, or $^{14}C$. Furthermore, any compounds, containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The compounds of the instant invention may be in a salt form. As used herein, a "salt" is salt of the instant compounds which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts". *J. Pharm. Sci.* 66:1-19).

As used herein, "alkyl" includes both branched and straight-chain saturated aliphatic hydrocarbon groups having the specified number of carbon atoms and may be unsubstituted or substituted. The Alkyls are C1-C10 alkyls, or a subset or individual thereof. In a non-limiting example, where the alkyl is C1-C5 as in "C1-C5 alkyl", it is defined to include groups having 1, 2, 3, 4 or 5 carbons in a linear or branched arrangement and specifically includes methyl, ethyl, n-propyl, isopropyl, n-butyl, t-butyl, and pentyl. Alkyl may optionally be substituted with phenyl or substituted phenyl to provide substituted or unsubstituted benzyl.

Heterocyclyl means a saturated or partially unsaturated monocyclic radical containing 3 to 8 ring atoms and preferably 5 to 6 ring atoms selected from carbon or nitrogen but not limited to pyrrolidine.

As used herein the term "aryl" refers to aromatic monocyclic or multicyclic groups containing from 5 to 15 carbon atoms. Aryl groups include, but are not limited to groups such as unsubstituted or substituted phenyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment. Aryl may optionally be substituted with a heterocyclyl-C(O)-moiety which includes a pyrrolidinyl-C(O)-moiety.

The term "heteroaryl" as used herein, represents a stable monocyclic, bicyclic or polycyclic ring of up to 10 atoms in each ring, wherein at least one ring is aromatic and contains from 1 to 4 heteroatoms or particularly 1 to 2 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom, selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteraryl substituent is bicyclic and one ring is non-aromatic or contains no heteroatoms it is understood that attachment is via the aromatic ring or via the heteroatom containing ring, respectively. If the heteroaryl contains nitrogen atoms, it is understood that the corresponding N-oxides thereof are also encompassed by this definition.

In the compounds of the present invention, the alkyl, aryl, or heteroaryl groups can be further substituted by replacing one or more hydrogen atoms be alternative non-hydrogen groups. These include, but are not limited to, 1-4 groups selected from alkyl, alkoxy, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon (s) or hydrogen (s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; heterocyclyl-C(O)-moiety; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. Moreover, where hydrogens are not shown in the carbon-based structures herein, implicit hydrogens are understood to complete valences as required.

The compounds of the instant invention may be in a salt form. As used herein, a "salt" is salt of the instant compounds which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts". J. Pharm. Sci. 66:1-19).

Where a numerical range is provided herein for any parameter, it is understood that all numerical subsets of that numerical range, and all the individual integer values contained therein, are provided as part of the invention. Thus, C1-C10 alkyl includes the subset of alkyls which are 1-3 carbon atoms, the subset of alkyls which are 2-5 carbon atoms etc, as well as an alkyl which has 1 carbon atom, an alkyl which has 3 carbon atoms, an alkyl which has 10 carbon atom, etc.

In an embodiment, the purines discussed herein are one or more of adenosine, inosine, hypoxanthine, or adenine. In an embodiment, "determining" as used herein means experimentally determining.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of a high-density lipoprotein-derived nanoparticle (HDL) compound which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

As used herein. "a compound of the invention" means a compound of formula 1, or a salt, solvate or physiologically functional derivative thereof.

As used herein, the term "solvate" refers to a complex of variable stoichiometry formed by a solute (e.g., a compound of formula 1, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

In certain embodiments, the term "physiologically functional derivative" refers to a compound (e.g. a drug precursor) that is transformed in vivo to yield a compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems." Vol. 14 of the A.C.S. Symposium Series, and in Bioreversible Carriers in Drug Design, ed. Edward B. Roche, American Pharmaceutical Association and Pergamon Press, 1987. Additionally, the term may encompass a compound (e.g, a drug precursor) that is transformed in vivo to yield a compound of HDL which encompasses a CD40-TRAF6 inhibitor. e.g. TRAF6i-HDL.

All combinations of the various elements described herein are within the scope of the invention unless otherwise indicated herein or otherwise clearly contradicted by context. Whilst the embodiments for each variable have generally been listed above separately for each variable, this invention also includes those compounds in which several or each embodiment for compounds of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), selected from each of the embodiments listed above. Therefore, this invention is intended to include all combinations of embodiments for each variable.

In certain embodiments, the present invention also includes compounds which further comprise a TRAF6i-HDL (also called CD40-TRAF6 inhibitor), wherein the inhibitor is 6877002 (described in Zarzycka, T. et al, *J. Chem. Inf Model.* 55:294-307 (2015) or a pharmaceutically acceptable salt, solvate, poly-morph, tautomer or prodrug thereof, formulated as TRAF6i-HDL nanoparticle (TRAF6i-HDL), selected from any of the embodiments listed above. Therefore, all combinations of embodiments for each variable are contemplated herein.

The high-density lipoprotein-derived nanoparticle (HDL) compound which comprises an in-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), and salts, solvates and physiologically functional derivatives thereof are believed to be useful for treating a subject at risk for allograft rejection and the method is for preventing (i.e., prophylaxis) or inhibiting allograft rejection. It is noted that any transplant is at risk for allograft rejection, and thus the compositions and methods described herein are contemplated for therapeutic use for any transplant condition. Furthermore, combining TRAF6i-HDL composition with the mTOR-HDL treatment regimen provides synergistic effects in preventing (i.e., prophylaxis) or inhibiting allograft rejection.

In a further embodiment, the present invention provides for the use of a compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or a pharmaceutically acceptable salt or solvate thereof, or a physiologically functional derivative thereof, in the preparation of a medicament for the treatment of a disorder mediated by certain levels of immune reactants that indicate a likelihood of immune intolerance.

Accordingly, the invention further provides a pharmaceutical composition, which comprises a compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), and salts, solvates and physiological functional derivatives thereof, and one or more pharmaceutically acceptable carers, diluents, or excipients. The compounds of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or salts, solvates and physiological functional derivatives thereof, with one or more pharmaceutically acceptable carriers, diluents or excipients.

The invention further provides a pharmaceutical composition, which comprises a compound of a high-density lipoprotein-derived nanoparticle (HDL) which comprises an CD40-TRAF6 inhibitor, wherein the CD40-TRAF6 inhibitor is 6877002, or a pharmaceutically acceptable salt, solvate, poly-morph, tautomer or prodrug thereof, formulated as CD40-TRAF6 nanoparticle (TRAF6i-HDL), and salts, solvates and physiological functional derivatives thereof, and one or more pharmaceutically acceptable carriers, diluents, or excipients. The compounds of a high-density lipoprotein-derived nanoparticle (HDL) which comprises a CD40-TRAF6 inhibitor, wherein the CD40-TRAF6 inhibitor is 6877002 or a pharmaceutically acceptable salt, solvate, poly-morph, tautomer or prodrug thereof, formulated as CD40-TRAF6 nanoparticle (TRAF6i-HDL), and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of a high-density lipoprotein-derived nanoparticle (HDL) which comprises a CD40-TRAF inhibitor, wherein the CD40-TRAF6 inhibitor is 6877002 or a pharmaceutically acceptable salt, solvate, poly-morph, tautomer or prodrug thereof, formulated as CD40-TRAF6 nanoparticle (TRAF6i-HDL), or salts, solvates and physiological functional derivatives thereof, with one or more pharmaceutically acceptable carriers, diluents or excipients.

Additionally, in certain embodiments, a combination composition comprising both the CD40-TRAF6 inhibitor and m-TOR inhibitor formulated as a combined HDL nanoparticle formulation is contemplated. In such a combination composition, the active agent/compound can be as described above, but any suitably charged CD40-TRAF6 inhibitor or m-TOR inhibitor can be formulated as a combined HDL nanoparticle formulation.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art. Exemplary dosage includes 5 mg/kg in mice.

Pharmaceutical compositions of the present invention may be adapted for administration by any appropriate route, for example by the oral (including buccal or sublingual), inhaled, nasal, ocular, or parenteral (including intravenous and intramuscular) route. Such compositions may be prepared by any method known in the art of pharmacy, for example by bringing into association the active ingredient with the carrier(s) or excipient(s).

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL) for the treatment of diseases or conditions associated with allograft rejection-including heart transplant, skin transplant, liver transplant, lung transplant, bronchiolitis-obliterans syndrome (BOS), kidney transplant, pancreas transplant, pancreatic islets transplant, intestinal transplant, bone transplant, retinal transplant, and corneal transplant will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), per se.

Compounds of the present invention, and their salts and solvates, and physiologically functional derivatives thereof, may be employed alone or in combination with other therapeutic agents for the treatment of diseases and conditions related to allograft rejection-including heart transplant, skin transplant, liver transplant, lung transplant, bronchiolitis-obliterans syndrome (BOS), kidney transplant, pancreas transplant, pancreatic islets transplant, intestinal transplant, bone transplant, retinal transplant, and corneal transplant.

Combination therapies according to the present invention thus comprise the administration of at least one compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or a pharmaceutically acceptable salt or solvate thereof, or a physiologically functional derivative thereof, and the use of at least one other pharmaceutically active agent. The compound(s) of compound of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL) and the other pharmaceutically active agent(s) may be administered together or separately and, when administered separately this may occur simultaneously or sequentially in any order. The amounts of the compound(s) of a high-density lipoprotein-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL) and the other pharmaceutically active agent(s) and the relative timings of administration will be selected in order to achieve the desired combined therapeutic effect.

In certain embodiments, combination therapies according to the present invention thus comprise the administration of (i) high-density lipoprotien-derived nanoparticle (HDL) which comprises an m-TOR inhibitor, wherein the m-TOR inhibitor is rapamycin or a pharmaceutically acceptable salt, solvate, poly-morph, tautomer or prodrug thereof, formulated as rapamycin nanoparticle (mTOR-HDL), or the pharmaceutical composition thereof and (ii) TRAF6i-HDL nanoparticles which comprises CD40-TRAF6 inhibitor, wherein the CD40-TRAF6 inhibitor is 6877002, or a pharmaceutically acceptable salt, solvate, poly-morph, tautomer or prodrug thereof, formulated as TRAF6i-HDL nanoparticle (also referred to generally as CD40-HDL), or the pharmaceutical composition thereof.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of the present invention may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of the present invention. Those skilled in the art will recognize if a stereocenter exists in compounds of the present invention. Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L Eliel, S. H. Wilen, and L. N. Mander (Wiley-Interscience, 1994).

A "transplantable graft" refers to a biological material, such as cells, tissues and organs (in whole or in part) that can be administered to a subject. Transplantable grafts may be autografts, allografts, or xenografts of, for example, a biological material such as an organ, tissue, skin, bone, nerves, tendon, neurons, blood vessels, fat, cornea, pluripotent cells, differentiated cells (obtained or derived in vivo or in vitro), etc. In some embodiments, a transplantable graft is formed, for example, from cartilage, bone, extracellular matrix, or collagen matrices. Transplantable grafts may also be single cells, suspensions of cells and cells in tissues and organs that can be transplanted. Transplantable cells typically have a therapeutic function, for example, a function that is lacking or diminished in a recipient subject. Some non-limiting examples of transplantable cells are islet cells, beta.-cells, hepatocytes, hematopoietic stem cells, neuronal stem cells, neurons, glial cells, or myelinating cells. Transplantable cells can be cells that are unmodified, for example, cells obtained from a donor subject and usable in transplantation without any genetic or epigenetic modifications. In other embodiments, transplantable cells can be modified cells, for example, cells obtained from a subject having a genetic defect, in which the genetic defect has been corrected, or cells that are derived from reprogrammed cells, for example, differentiated cells derived from cells obtained from a subject.

"Transplantation" refers to the process of transferring (moving) a transplantable graft into a recipient subject (e.g., from a donor subject, from an in vitro source (e.g., differentiated autologous or heterologous native or induced pluripotent cells)) and/or from one bodily location to another bodily location in the same subject.

"Undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health.

In an embodiment, the transplanted tissue is lung tissue, heart tissue, kidney tissue, liver tissue, retinal tissue, corneal tissue, skin tissue, pancreatic tissue, intestinal tissue, genital tissue, ovary tissue, bone tissue, tendon tissue, or vascular tissue.

In an embodiment, the transplanted tissue is transplanted as an intact organ.

As used herein a "recipient subject" is a subject who is to receive, or who has received, a transplanted cell, tissue or organ from another subject.

As used herein a "donor subject" is a subject from whom a cell, tissue or organ to be transplanted is removed before transplantation of that cell, tissue or organ to a recipient subject.

In an embodiment the donor subject is a primate. In a further embodiment the donor subject is a human. In an embodiment the recipient subject is a primate. In an embodiment the recipient subject is a human. In an embodiment both the donor and recipient subjects are human. Accordingly, the subject invention includes the embodiment of xenotransplantation.

As used herein "rejection by an immune system" describes the event of hyperacute, acute and/or chronic response of a recipient subject's immune system recognizing a transplanted cell, tissue or organ from a donor as non-self and the consequent immune response.

The term "allogenic" refers to any material derived from a different animal of the same species as the individual to whom the material is introduced. Two or more individuals are said to be allogeneic to one another when the genes at one or more loci are not identical.

The term "autologous" refers to any material derived from the same individual to whom it is later to be re-introduced into the same individual.

As used herein an "immunosuppressant pharmaceutical" is a pharmaceutically-acceptable drug used to suppress a recipient subject's immune response. Non-limiting examples include cyclosporine A, FK506 and rapamycin.

As used herein, a "prophylactically effective" amount is an amount of a substance effective to prevent or to delay the onset of a given pathological condition in a subject to which the substance is to be administered. A prophylactically effective amount refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "therapeutically effective" amount is an amount of a substance effective to treat, ameliorate or lessen a symptom or cause of a given pathological condition in a subject suffering therefrom to which the substance is to be administered.

In one embodiment, the therapeutically or prophylactically effective amount is from about 1 mg of agent/kg subject to about 1 g of agent/kg subject per dosing. In another embodiment, the therapeutically or prophylactically effective amount is from about 10 mg of agent/kg subject to 500 mg of agent/subject. In a further embodiment, the therapeutically or prophylactically effective amount is from about 50 mg of agent/kg subject to 200 mg of agent/kg subject. In a further embodiment, the therapeutically or prophylactically effective amount is about 100 mg of agent/kg subject. In still a further embodiment, the therapeutically or prophylactically effective amount is selected from 50 mg of agent/kg subject, 100 mg of agent/kg subject, 150 mg of agent/kg subject, 200 mg of agent/kg subject, 250 mg of agent/kg subject, 300 mg of agent/kg subject, 400 mg of agent/kg subject and 500 mg of agent/kg subject.

"Treating" or "treatment" of a state, disorder or condition includes:

(1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease. i.e., causing regression of the state, disorder or condition or at least one of its clinical or sub-clinical symptoms or signs.

The benefit to a subject to be treated is either statistically significant or at least perceptible to the patient or to the physician.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

"Patient" or "subject" refers to mammals and includes human and veterinary subjects. Certain veterinary subjects may include avian species.

This invention will be better understood from the Experimental Details, which follow. However, one skilled in the art will readily appreciate that the specific methods and results discussed are merely illustrative of the invention as described more fully in the claims that follow thereafter.

GENERAL METHODS

Standard methods in molecular biology are described Sambrook, Fritsch and Maniatis (1982 & 1989 $2^{nd}$ Edition. 2001 $3^{rd}$ Edition) *Molecular Cloning, A laboraory Manual. Cold Spring Harbor Laboratory Press*, Cold Spring Harbor, NY; Sambrook and Russell (2001) *Molecular Cloning.* $3^{rd}$ *ed.*, Cold Spring Harbor Laboratory Press, Cold Spring Harbor. NY; Wu (1993) *Recombinant DNA. Vol.* 217. Academic Press. San Diego, CA). Standard methods also appear in Ausbel, et at. (2001) *Current Protocols in Molecular Biology. Vols.* 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1. John Wiley and Sons, Inc., New York). Chemical analysis, chemical modification, post-translational modification, production of fusion proteins, glycosylation of proteins are described (see. e.g., Coligan, et al. (2000) *Current Protocols in Protein Science. Vol.* 2. John Wiley and Sons, Inc., New York; Ausubel, et al. (2001) *Current Protocols in Molecular Biology, Vol.* 3. John Wiley and Sons. Inc., NY, NY, pp. 16.0.5-16.22.17; Sigma-Aldrich, Co. (2001) *Products for Life Science Research*, St. Louis. MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press. Cold Spring Harbor. NY; Harlow and Lane, *supra*). Standard techniques for characterizing ligand/receptor interactions are available (see, e.g., Coligan, et al. (2001) *Current Protocols in Immunology, Vol.* 4. John Wiley, Inc., New York).

Rapamycin is a known macrolide antibiotic produced by *Streptomyces hygroscopicus*. Suitable derivatives of rapamycin include e.g. compounds of formula 1 wherein $R_1$ is $CH_3$ or $C_3$-6alkynyl, $R_2$ is H or —$CH_2$-$CH_2$-OH, and X is =O, (H,H) or (H,OH) provided that $R_2$ is other than H when X is =O and $R_1$ is $CH_3$. The structure of rapamycin is shown below:

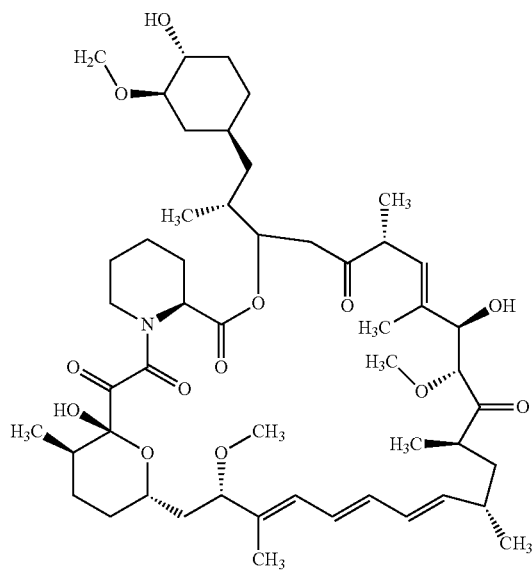

Formula I

Compounds of formula 1 are disclosed e.g. in U.S. Pat. Nos. 5,665,772: 6,440,990; 5,985,890; and 6,200,985, which are incorporated herein by reference. They may be prepared as disclosed or by analogy to the procedures described in these references.

Preferred compounds are 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-O-(2-hydroxyethyl)-rapamycin and, more preferably, 40-O-(2-hydroxyethyl)-rapamycin (referred thereafter as Compound A), disclosed as Example 8 in U.S. Pat. Nos. 5,665,772 and 6,440,990.

Compounds of formula 1 have, on the basis of observed activity, e.g. binding to macrophyllin-12 (also known as FK-506 binding protein or FKBP-12), e.g. as described in WO 94/09010. WO 95/16691 or WO 96/41807, been found to be useful e.g. as immunosuppressant, e.g. in the treatment of acute allograft rejection.

Embodiments also include nanoparticles comprising rapamycin derivatives with improved hydrophobicity and/or miscibility. For example, rapamycin may be conjugated with an alkyl chain as described in Zhao et al., Augmenting drug-carrier compatibility improves tumour nanotherapy efficacy, Nature Communications 7. Article number: 11221 (2016) doi:10.1038/ncomms11221.

In certain embodiments, the addition of cholesterol has stabilized the formulation as well as improved entrapment efficiency. In certain embodiments, the weight percentage of cholesterol ranges from about 0% to about 10% (w/w), from about 1% (w/w) to about 10% (w/w), from about 2% (w/w) to about 10% (w/w), from about 3% (w/w) to about 10% (w/w), from about 4% (w/w) to about 10% (w/w), from about 5% (w/w) to about 10% (w/w), from about 6% (w/w) to about 10% (w/w), from about 7% (w/w) to about 10% (w/w), from about 8% (w/w) to about 10% (w/w), from about 1% (w/w) to about 9% (w/w), from about 1% (w/w) to about 8% (w/w), from about 1% (w/w) to about 7% (w/w), or from about 1% (w/w) to about 6% (w/w), of the nanoparticle, of the lipids, or of the composition.

Delivery vehicles such as liposomes, nanocapsules, microparticles, microspheres, lipid particles, vesicles, and the like, may be used for the introduction of the compositions of the present invention targeting the innate immune system, e.g. targeting macrophages to induce transplantation tolerance. In addition to being formulated as a nanotherapy as mTOR-HDL, the compounds targeting macrophages may be formulated for delivery in a number of different forms and methods including either encapsulated in a lipid particle, a liposome, a vesicle, a nanosphere, or a nanoparticle or the like.

The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the compositions of the present invention targeting the innate immune system may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In certain embodiments, synthetic nanocarriers do not comprise chitosan. In other embodiments, inventive synthetic nanocarriers are not lipid-based nanoparticles. In further embodiments, synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptidic or protein-based particles (also referred to herein as protein particles. i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine, 5(6):843-853 (2010, or (11) apoptotic cells, apoptotic bodies or the synthetic or semisynthetic mimics disclosed in U.S. Publication 2002/0086049. In embodiments, synthetic nanocarriers may possess an aspect ratio greater than 1:1, 1:1.2, 1:1.5, 1:2, 1:3, 1:5, 1:7, or greater than 1:10.

Synthetic nanocarriers may have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In certain embodiments, synthetic nanocarriers may have a minimum dimension of equal to or less than about 100 nm, preferably equal to or less than 100 nm, do not comprise a surface that substantially activates complement or alternatively comprise a surface that consists essentially of moieties that do not substantially activate complement. Synthetic nanocarriers in some embodiments have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

In certain embodiments, the present composition comprises (consists essentially of, or consists of) one or more types of phospholipids.

Examples of suitable phospholipids include, without limitation, phosphatidylcholines, phosphatidylethanolamines, phosphatidylinositol, phosphatidylserines, sphingomyelin or other ceramides, as well as phospholipid-containing oils such as lecithin oils. Combinations of phospholipids, or mixtures of a phospholipid(s) and other substance(s), may be used.

Non-limiting examples of the phospholipids that may be used in the present composition include, dimyristoylphosphatidylcholine (DMPC), soy lecithin, dipalmitoylphosphatidylcholine (DPPC), distearoylphosphatidylcholine (DSPC), dilaurylolyphosphatidylcholine (DLPC), dioleoylphosphatidylcholine (DOPC), dilaurylolylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglyceml (DOPG), dimyristoyl phosphatidic acid (DMPA), dimyristoyl phosphatidic acid (DMPA), dipalmitoyl phosphatidic acid (DPPA), dipahnitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalrnitoyl phosphatidylserine (DPPS), dipalmitoyl sphingomyelin (DPSP), distearoyl sphingomyelin (DSSP), and mixtures thereof.

In certain embodiments, when the present composition comprises (consists essentially of, or consists of) two or more types of phospholipids, the weight ratio of two types of phospholipids may range from about 1:10 to about 10:1, from about 2:1 to about 4:1, from about 1:1 to about 5:1, from about 2:1 to about 5:1, from about 6:1 to about 10:1, from about 7:1 to about 10:1, from about 8:1 to about 10:1, from about 7:1 to about 9:1, or from about 8:1 to about 9:1. For example, the weight ratio of two types of phospholipids may be about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1.

In one embodiment, the present high-density lipoprotein (HDL)-derived nanoparticle comprises (consists essentially of, or consists of) 1,2-dimyristoyl-sn-glycero-3-phosphatidylcholine (DMPC), and 1-myristoyl-2-hydroxy-sn-glycero-phosphocholine (MHPC). The weight ratio of DMPC to MHPC may range from about 1:10 to about 10:1, from about 2:1 to about 4:1, from about 1:1 to about 5:1, from about 2:1 to about 5:1, from about 6:1 to about 10:1, from about 7:1 to about 10:1, from about 8:1 to about 10:1, from about 7:1 to about 9:1, or from about 8:1 to about 9:1. The weight ratio of DMPC to MHPC may be about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1.

mTor Inhibitors and Combination with Other Pharmaceutically Active Components

Examples of mTOR inhibitors include rapamycin and analogs thereof (e.g., CCL-779, RAD001, AP23573, C20-methallylrapamycin (C20-Marap). C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RADM001). KU-0063794, PI-103. PP242, temsirolimus, and WYE-354 (available from Selleck, Houston, Tex., USA).

In certain embodiments, one or more additional or alternative active ingredients targeting PIRb+ macrophages and promoting allograft survival may be utilized in combination. Any one or more of these active ingredients may be formulated in one dosage unit, or in a combination of forms such as an mTOR-HDL nanoparticle could be administered in combination with a lipid particle, a liposome, a vesicle, a nanosphere comprising a second or third active ingredient. Other suitable active agents include one or more immunosuppressive agents.

Treatment Regimens/Options

The mTOR-HDL can be used in combination with other induction therapies that target the adaptive immune response such as T and B cell depletion. For example, for kidney living donors, transplant recipients can be treated before and shortly after transplantation. Patients under current immunosuppressive therapy can be switched to the mTOR-HDL therapy, or combination mTOR-HDL/TRAF6i-H1DL therapy. In additional scenarios, mTOR-HDL treatment is administered to the patient prior to and shortly after transplantation, which can be repeated every 6 or 12 months, with the goal to eliminate or strongly reduce immunosuppressive therapy. In additional scenarios, patients are administered the mTOR-HDL, therapy, or combination mTOR-HDL/TRAF6i-HDL therapy without any additional immunosuppressive therapy.

Exemplary immunosuppressant include, but are not limited to, statins; mTOR inhibitors, such as rapamycin or a rapamycin analog; TGF-.beta, signaling agents; TGF-.beta, receptor agonists; histone deacetylase (HDAC) inhibitors; corticosteroids; inhibitors of mitochondrial function, such as rotenone; P38 inhibitors; NF—.kappa.beta, inhibitors; adenosine receptor agonists; prostaglandin E2 agonists; phosphodiesterase inhibitors, such as phosphodiesterase 4 inhibitor; proteasome inhibitor; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathioprine, 6-mercaptopurine, aspirin, niflumic acid, estriol, triptolide, interleukins (e.g., IL-1, IL-10l) cyclosporine A, siRNAs targeting cytokines or cytokine receptors and the like. Examples of statins include atorvastatin (LIPITOR.RTM., TORVAST.RTM.), cerivastatin, fluvastatin (LESCOL.RTM., LESCOL.RTM. XL), lovastatin (MEVACOR.RTM., ALTOCOR.RTM., ALTOPREV.RTM.), mevastatin (COMPACTIN.RTM), pitavastatin (LIVALO.RTM., PIAVA.RTM.), mevastatin (PRAVACHOL.RTM., SELEKTINE.RTM., LIPOSTAT.RTM.), rosuvastatin (CRESTOR.RTM.), and simvastatin (ZOCOR.RTM., LIPEX.RTM.).

The mTOR-HDL nanotherapy was tested in an allogeneic heart transplantation mouse model. The regimen comprised only three intravenous tail vein injections of 5 mg/kg equivalent rapamycin during the first week after transplantation. Using a combination of in vivo positron emission tomography with computed tomography (PET-CT) imaging and an array of immunological assays, the heart allograft targeting and cellular specificity were evaluated. Subsequently, the innate immune response was analyzed along with allograft survival and therapeutic mechanisms. These results demonstrate that mTOR-HDL nanoparticle treatment promotes indefinite heart allograft survival. Additionally, similar results were also observed for a skin transplant model. These results demonstrate how to manipulate the immune response toward inducing donor-specific non-response in the clinic and identify new therapeutic targets that may prevent allograft rejection in humans.

EXAMPLES

Example 1

Development of mTOR-HDL Nanoparticles mTOR-HDL nanoparticles (see FIG. 1A) were synthesized by hydrating a lipid film, containing rapamycin and phospholipids, with APOA1 in PBS. Subsequently, and after vigorous homogenization, the sample was sonicated to generate mTOR-HDL nanoparticles with 62±11% rapamycin encapsulation efficiency and a mean hydrodynamic diameter of 12.7±4.4 nm, as determined by high performance liquid chromatography and dynamic light scattering, respectively. The size of the nanoparticles can vary, but will typically be from about 10 nm to about 250 nm.

Figure 1B:
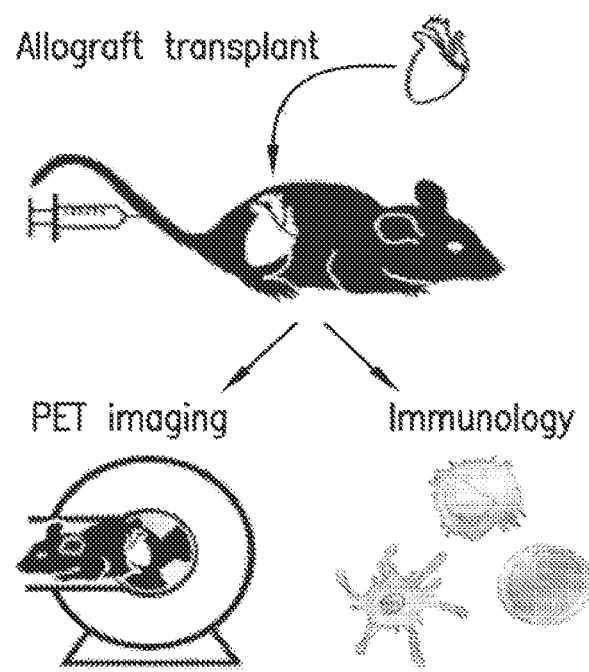
Figure 4:
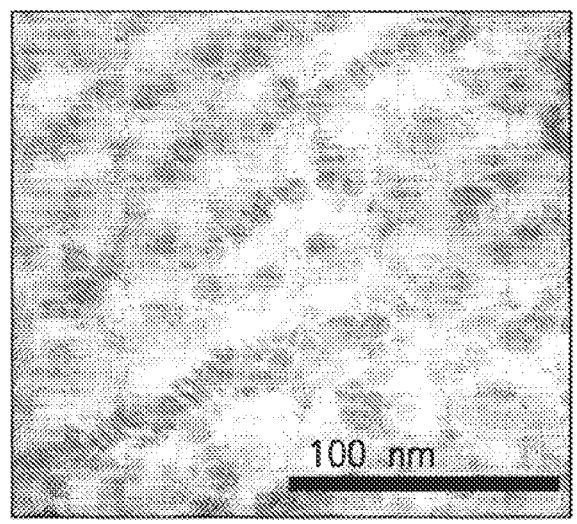
FIG. 4 is a transmission electron micrograph showing the discoidal morphology of mTOR-HDL.
Figure 5A:
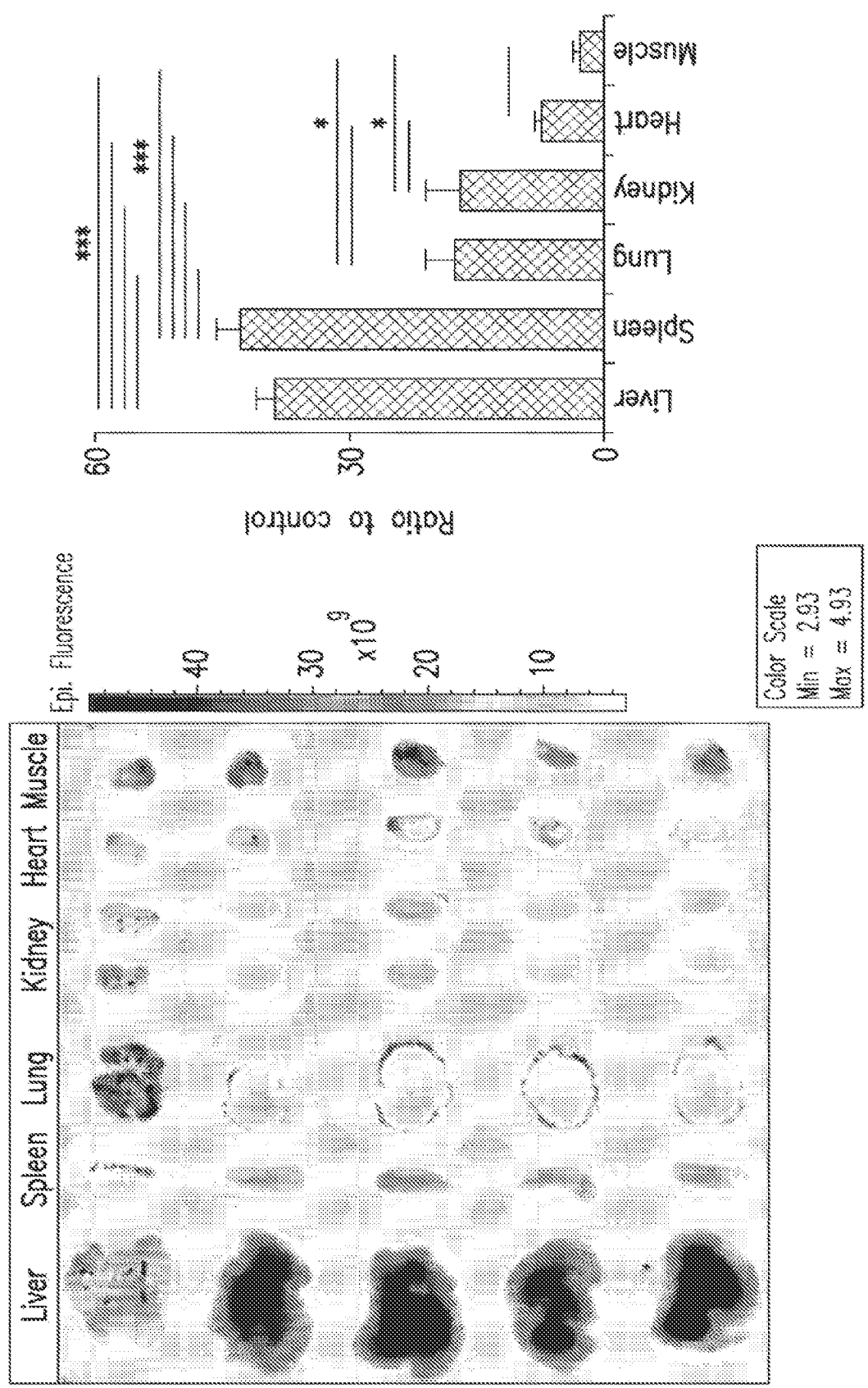
FIGS. 5A-C are graphs and images showing physiological biodistribution and mTOR-HDL targeting in C57/B16 wild type mice.
Figure 5B:
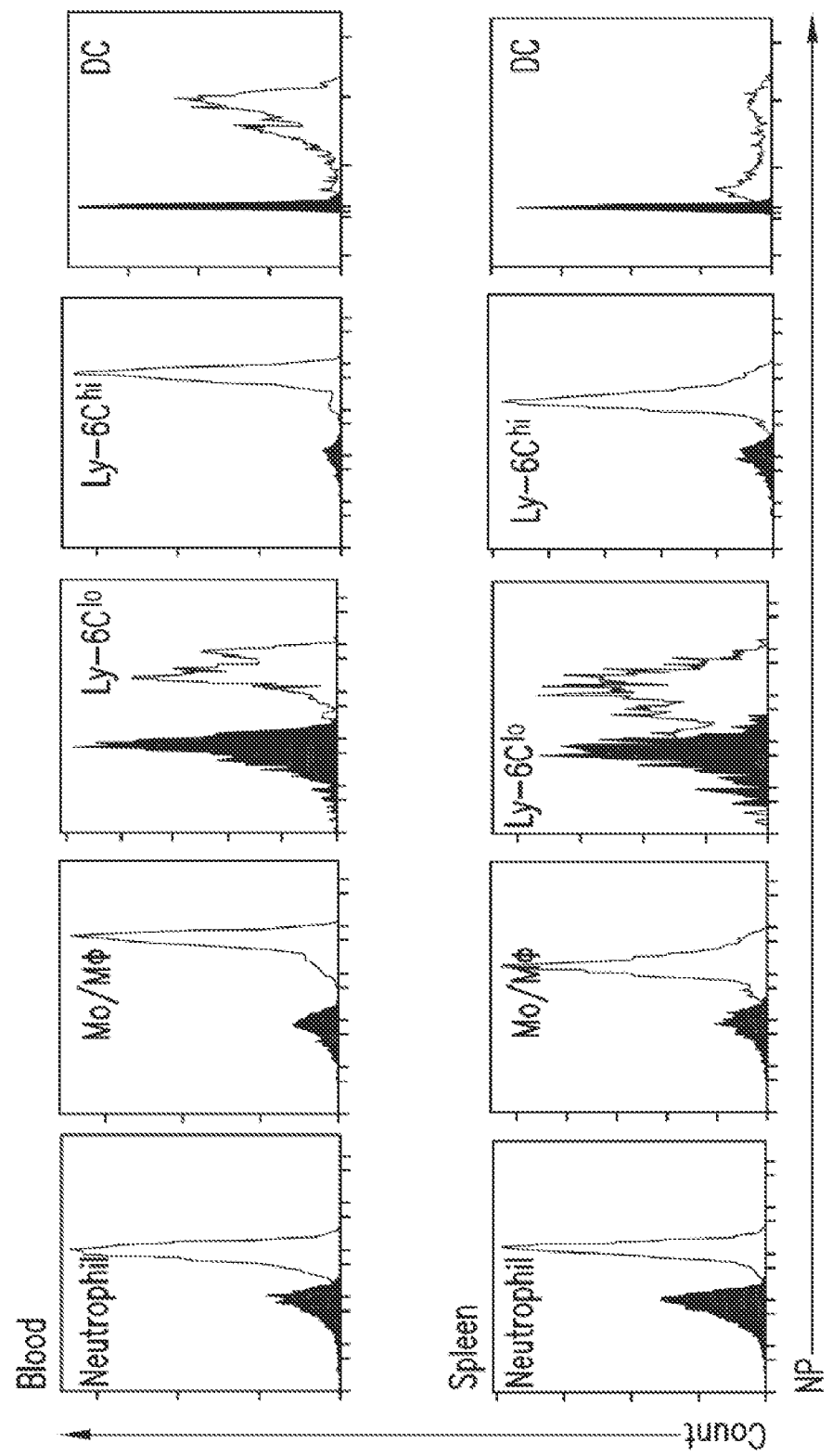
Figure 5C:
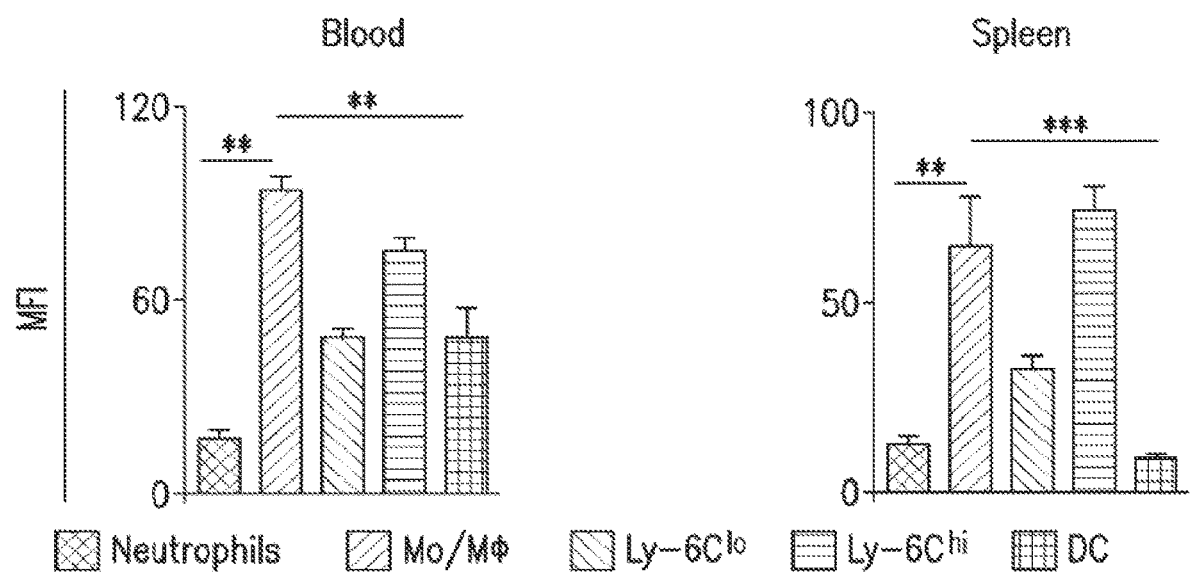
Figure 6:
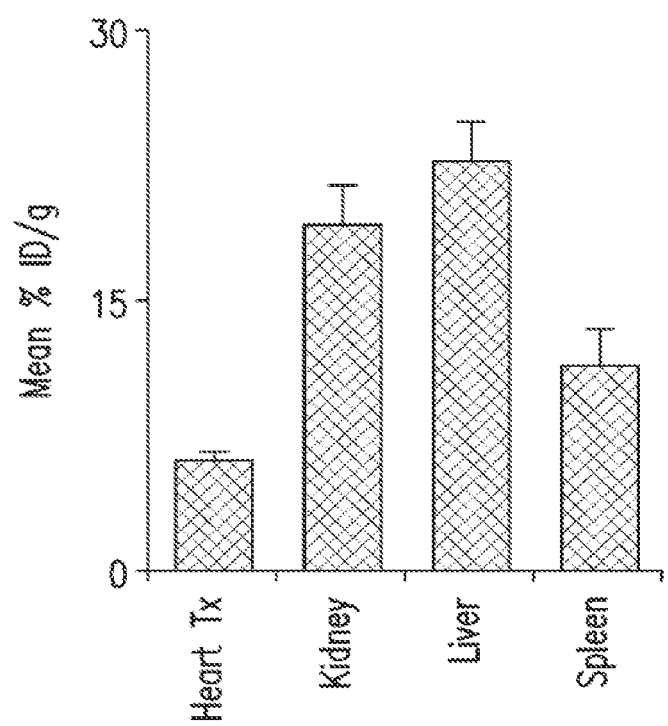
FIG. 6 is a graph showing PET-quantified uptake values according to the mean % ID/g in transplanted heart, kidney, liver and spleen, n=3.
Figure 7A:
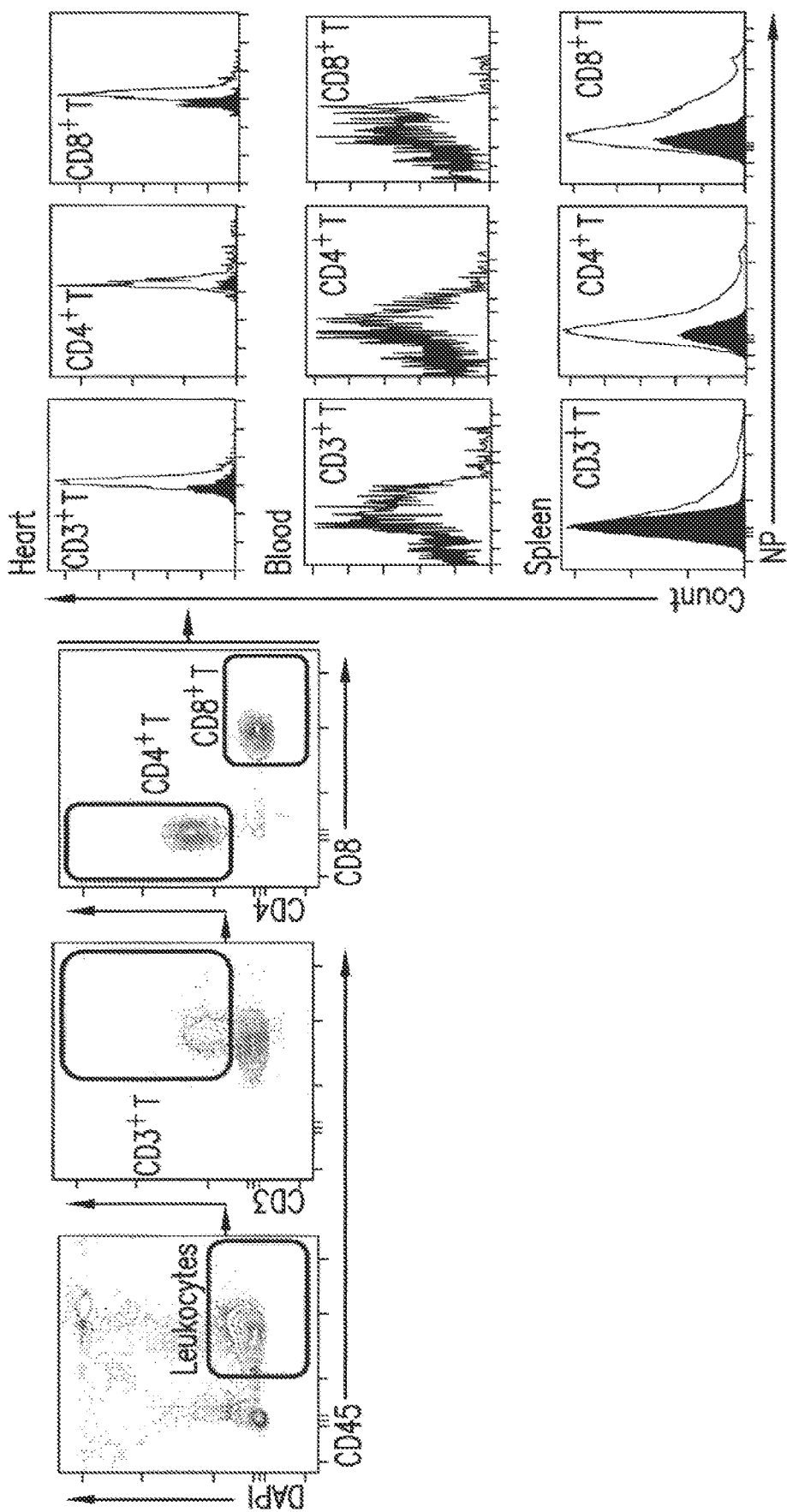
FIGS. 7A-B are graphs and flow cytometry images showing mTOR-HDL nanoimmunotherapy does not target T lymphocytes.
Figure 7B:
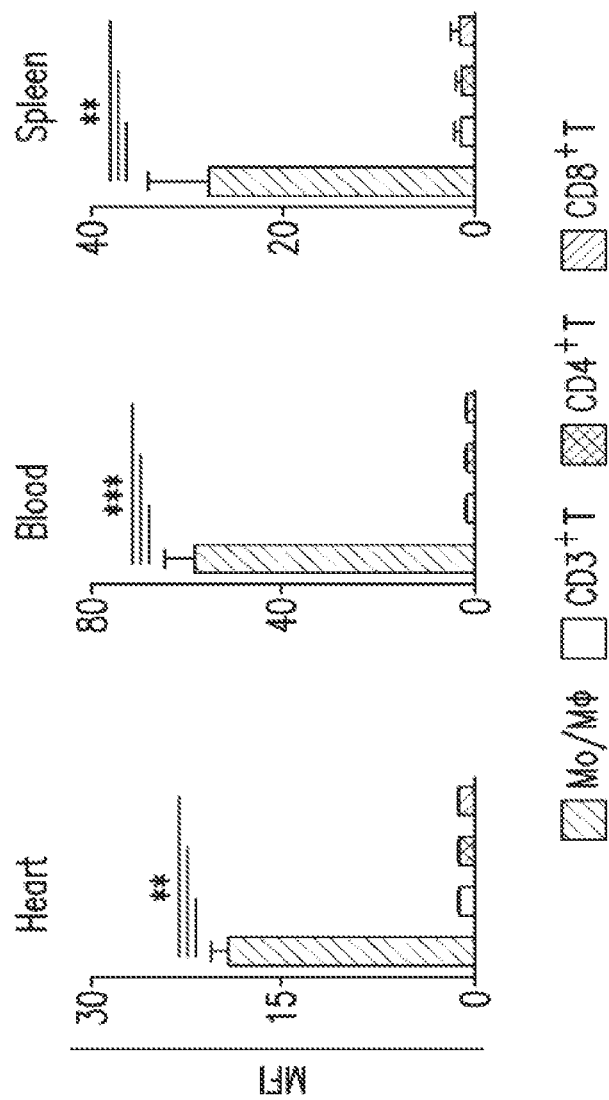

As revealed by transmission electron microscopy (FIG. 4), the mTOR-HDL had the discoidal structure that is typical of HDL-based nanoparticles[16]. The biodistribution and cellular specificity of 1,1'-Dioctadecyl-3,3,3',3'-Tetramethylindotricarbocyanine Iodide (DiR)-labeled mTOR-HDLs were evaluated in C57B1/6 wild type mice using ex vivo near infrared fluorescence (NIRF) imaging and flow cytometry, mTOR-HDL was shown to accumulate primarily in the liver, spleen and kidneys (FIG. 5A) while displaying a higher affinity for monocytes than either dendritic cells (DC) or neutrophils in the blood and spleen (FIG. 5B, C) (respectively, $P \leq 0.001$, $P \leq 0.01$ and $P \leq 0.01$, $P \leq 0.01$).

mTOR-HDL treatment was utilized in a heart transplant mouse model (FIG. 1B). mTOR-HDL's biodistribution, allograft targeting, and cellular specificity were determined using in vivo PET-CT imaging (FIG. 1B) and ex vivo techniques. Subsequently, an array of immunological readouts, including flow cytometry, enzyme-linked immunosorbent assay and mixed lymphocyte reaction were utilized, to evaluate the effects of a short-term mTOR-HDL nanotherapy regimen (FIG. 1B).

mTOR-HDL Nanotherapy Targets the Innate Immune System

Figure 1C:
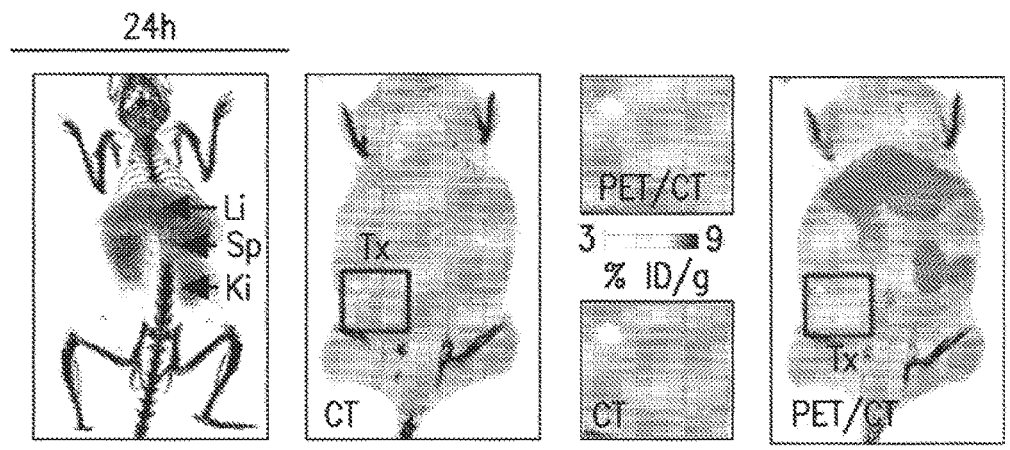
Figure 1D:
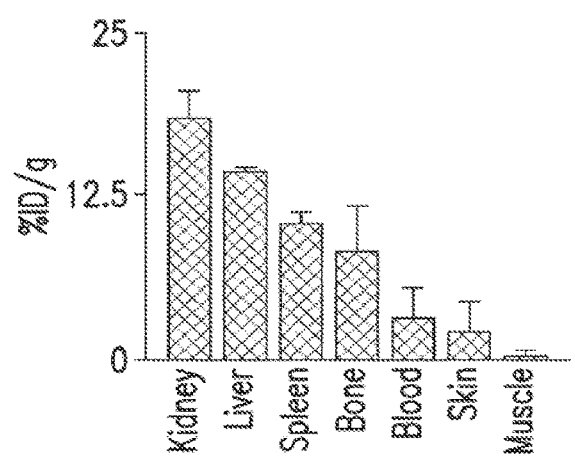
Figure 1E:
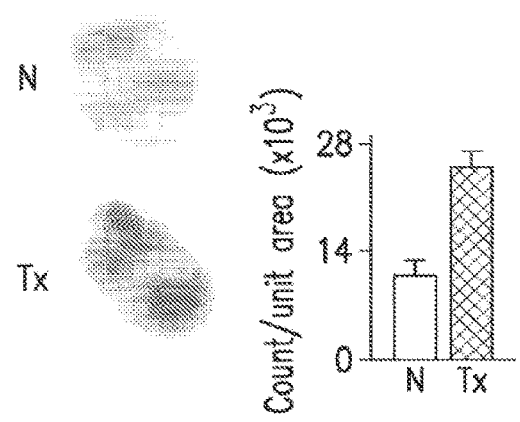
Figure 1F:
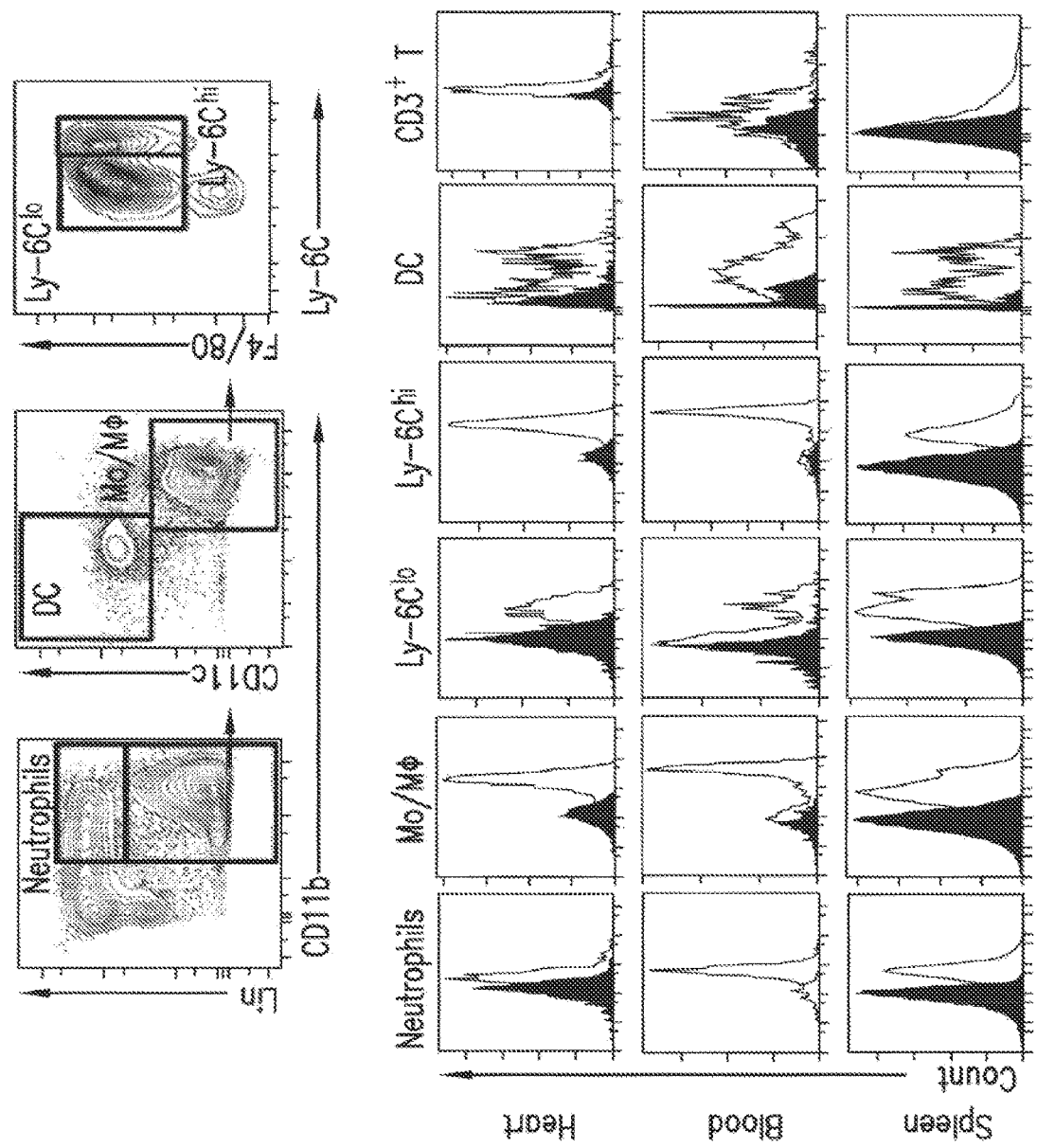

To quantitatively study tissue targeting and specificity, mTOR-HDL nanoparticles were radiolabeled with $^{89}Zr$ ($^{89}Zr$-mTOR-HDL). Six days after having hearts transplanted into their abdomens, mice received $^{89}Zr$-mTOR-HDL intravenously. The nanoparticles were allowed to circulate and distribute for 24 hours before mice underwent in vivo PET-CT imaging. Marked $^{89}$Zr-mTOR-HDL presence was observed in the heart allografts (FIG. 1C). After imaging, mice were sacrificed, and the organs were collected for $^{89}$Zr-mTOR-HDL quantification by ex vivo autoradiography. Allograft heart (Tx) activity ($25.2 \pm 2.4 \times 10^3$ counts/unit area) was determined to be 2.3 fold higher than in native hearts (N) ($11.1 \pm 1.9 \times 10^3$ count/unit area) (FIG. 1F). Gamma counting assessed $^{89}$Zr-mTOR-HDL's full biodistribution. The ex vivo autoradiography indicates that $^{89}$Zr-mTOR-HDL target many tissues (FIG. 1D), suggesting a systemic bio-distribution of the drug, consistent with the typical pattern of distribution for drug-loaded HDL nanoparticles[17].

The favorable organ distribution pattern and heart allograft uptake, lead the inventors to evaluate mTOR-HDL targeting and specificity at the cellular level in the heart allograft, blood, spleen and bone marrow, mTOR-HDL nanoparticles were labeled with the fluorescent dye 3,3'-Dioctadecyloxacartbocyanine Perchlorate (DiO), intravenously administered and allowed to circulate for 24 hours. Drawing on several tissue types, myeloid cells were extracted, including neutrophils; the monocyte/macrophage (Mo/MD) pool, including Ly-6C$^{lo}$ and Ly-6C$^{hi}$ monocytes, DCs, and T cells for analysis by flow cytometry.

Myeloid cell targeting was observed in the heart allograft, blood and spleen (FIGS. 1F and 1G). Importantly, the inventors observed cellular specificity towards the Mo/MΦ pool and neutrophils, with significantly higher mTOR-HDL uptake by the Mo/MΦ pool than either DC or neutrophils in the heart, blood and spleen (respectively: $P \leq 0.01$, $P \leq 0.01$, $P \leq 0.05$ and $P \leq 0.01$, $P \leq 0.01$, $P \leq 0.05$). In contrast, the DiO-labeled mTOR-HDL uptake by T cells was virtually absent (FIG. 1F, 1G), indicative for the nanotherapy's innate immune cell specificity. Overall, the data demonstrate that mTOR-HDL exhibits high specificity for inflamed sites, such as the heart allograft, and is avidly taken up by myeloid cells including monocytes, DC and neutrophils.

mTOR-HDL Significantly Decreases the Myeloid Cell Compartment

Figure 2A:
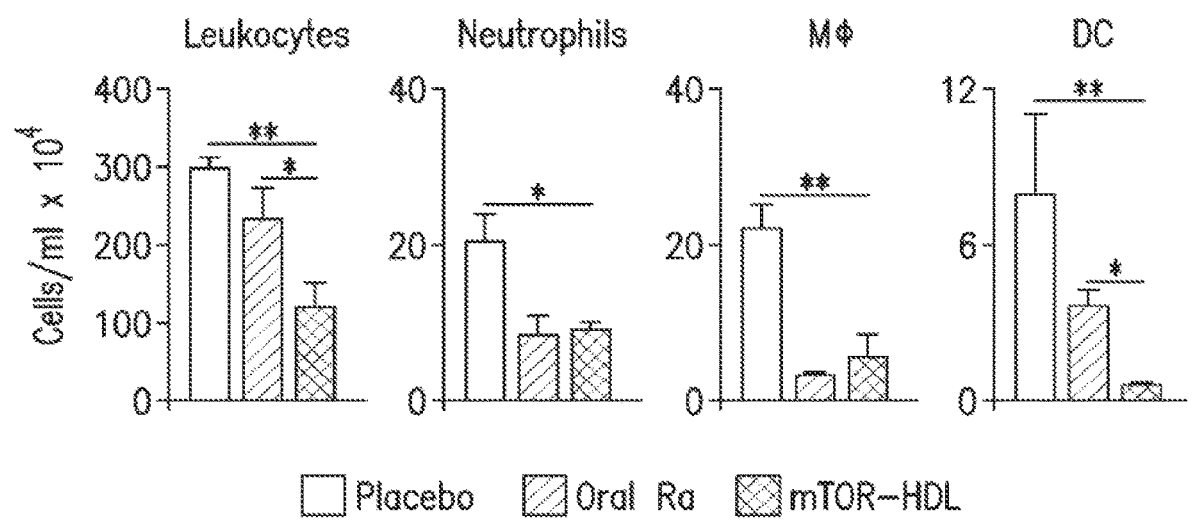
FIG. 2A-C are images and graphs showing that mTOR-HDL nanoimmunotherapy rebalances the innate immune system.
Figure 8:
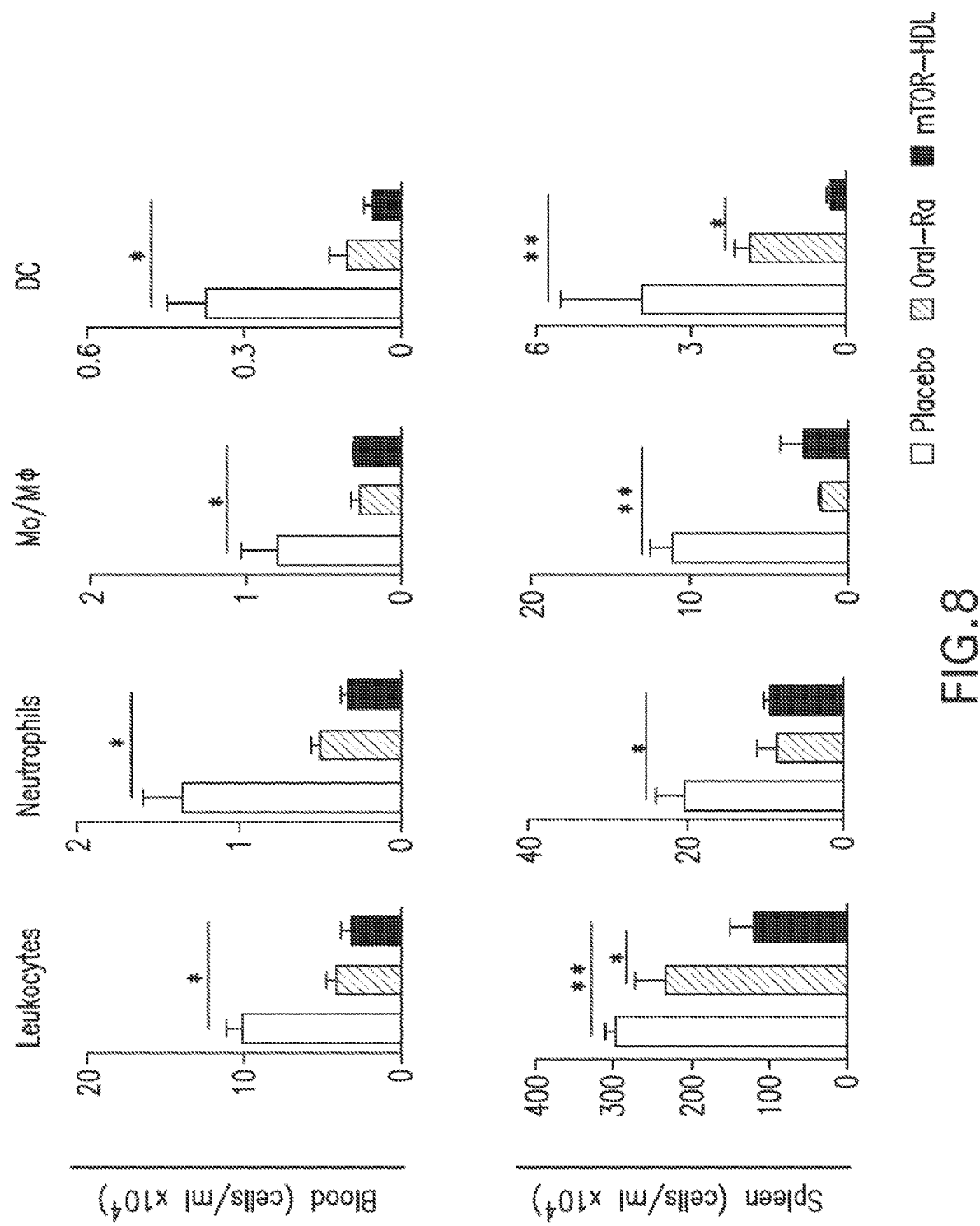
FIG. 8 is graphs showing flow cytometric analysis of cell suspensions retrieved from blood and spleen of placebo. Oral-Ra and mTOR-HDL-treated allograft recipients at day 6 post transplantation. Data are shown as mean±SEM: n=4 per group; *P≤0.05; **P≤0.01.

The leukocyte population was profiled and, more extensively, the myeloid cell compartment, including neutrophils. Mo/MΦ and DC, in the blood, spleens and allografts of mice receiving placebo, oral rapamycin (Oral-Ra) and mTOR-HDL treatments, where the treatment regimen involved three intravenous mTOR-HDL injections, on the day of, as well as at two and five days post transplantation. In line with the targeting data, significantly decreased total leukocytes were observed in the blood, spleens and allografts (FIG. 2A and FIG. 8) of mTOR-HDL-treated recipients as compared to either placebo ($P \leq 0.05$ and $P \leq 0.01$) or Oral-Ra-treated recipients. Additionally, these data show that mTOR-HDL treatment lowered neutrophil levels in the blood, spleen and allograft, as compared to both placebo ($P \leq 0.05$, $P \leq 0.05$ and $P \leq 0.05$) and Oral-Ra-treated recipients ($P \leq 0.05$). In addition, mTOR-HDL treatment dramatically reduced Mo/MΦ numbers in the circulation, spleen and heart allografts, as compared to placebo ($P \leq 0.05$, $P \leq 0.01$ and $P \leq 0.05$) or Oral-Ra-treated recipients ($P \leq 0.05$). Finally, mTOR-HDL treatment dramatically decreased DC in the circulation, spleen and allograft, as compared to placebo ($P \leq 0.05$, $P \leq 0.01$ and $P \leq 0.05$) or Oral-Ra-treated recipients ($P \leq 0.05$). All together, these results demonstrate that mTOR-HDL treatment limits the alloreactive immune response by interfering with myeloid cell accumulation in the transplanted allograft.

Figure 2B:
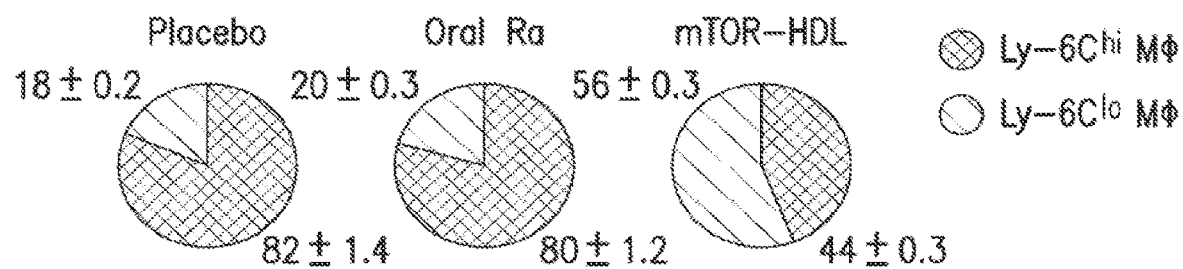
Figure 9A:
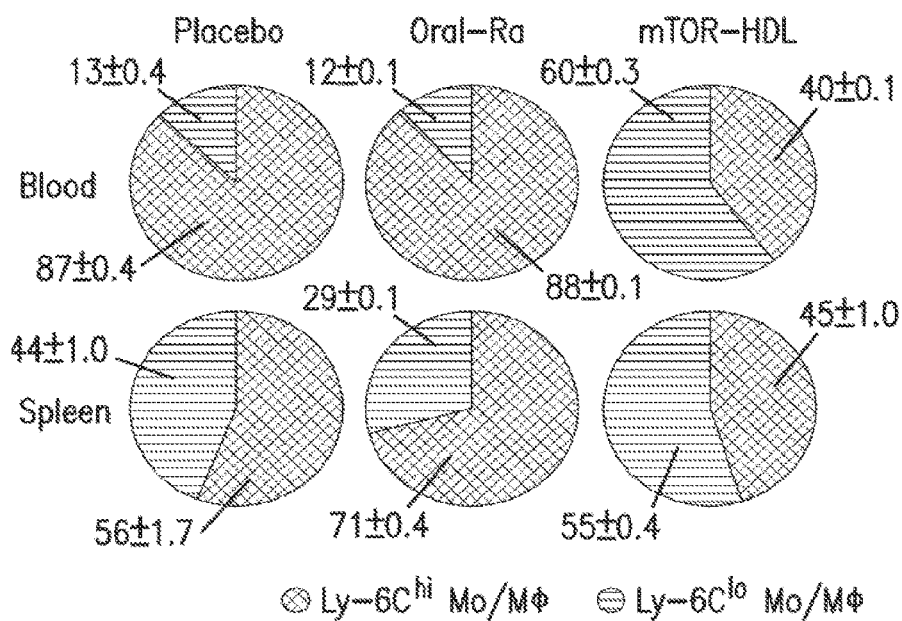
FIGS. 9A-B are diagrams and graphs relating to the frequency of Ly-6C$^{hi}$ vs. Ly-6C$^{lo}$ monocytes in the blood and spleen from placebo, Oral-Ra and mTOR-HDL-treated allograft recipients.
Figure 9B:
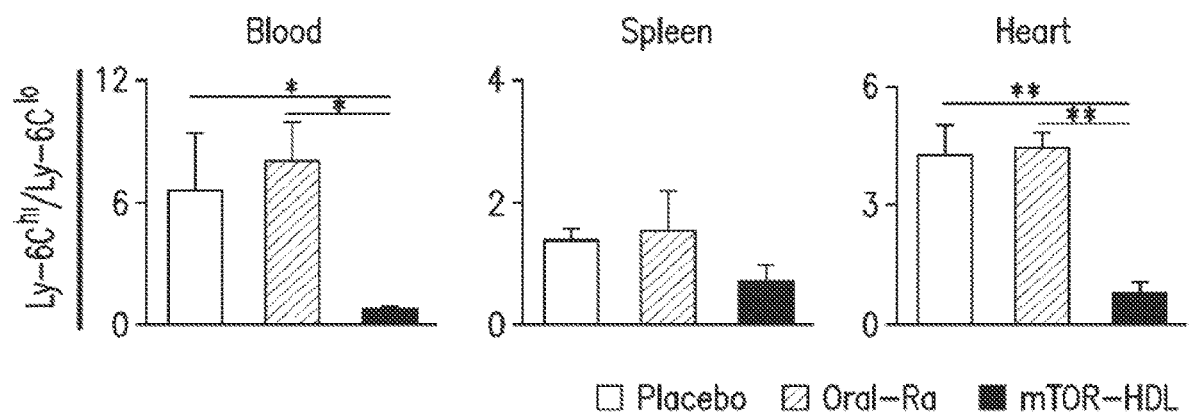

Following these myeloid cell investigations, the effects of mTOR-HDL nanotherapy on Mo/MΦ tissue distribution were evaluated. Mo/MΦ comprise two different subsets (Ly-6C$^{hi}$ and Ly-6C$^{lo}$) with district migratory properties[23]. Six days after transplantation, untreated and Oral-Ra-treated mice had increased numbers of accumulated myeloid cells in their blood, spleen and heart allografts (FIG. 2B and FIG. 9A). Further, the elevated Mo/MΦ populations contained high percentages of inflammatory Ly6C$^{hi}$ monocytes (FIGS. 9A and 2B). By contrast, mTOR-HDL recipients accumulated significantly more Ly-C$^{lo}$ monocytes than placebo and Oral-Ra-treated animals in blood (60% vs. 12% and 13%), spleen (55% vs. 29% and 44%) and heart allografts (56% vs. 20% and 18%) (FIG. 2B, FIG. 9A). Accordingly, notably fewer circulating Ly-6C$^{hi}$ monocytes were identified in the mTOR-HDL-treated group than in either the placebo or the Oral-Ra-treated recipients ($P \leq 0.05$ and $P \leq 0.05$, respectively). The Mo/MΦ subset proportions in the spleen and transplanted organs reflected the levels in peripheral blood (FIG. 1E). The data indicate that while Ly-6C$^{hi}$ monocytes dominate the myeloid response in transplant rejection, Ly-6C$^{lo}$ monocytes dominate the myeloid response during tolerance. This suggests mTOR-HDL treatment promotes the accumulation of regulatory Ly-6C$^{lo}$ MΦ, and can rebalance the myeloid compartment in favor of homeostasis.

mTOR Pathway is Negatively Regulated by mTOR-HDL

Figure 2C:
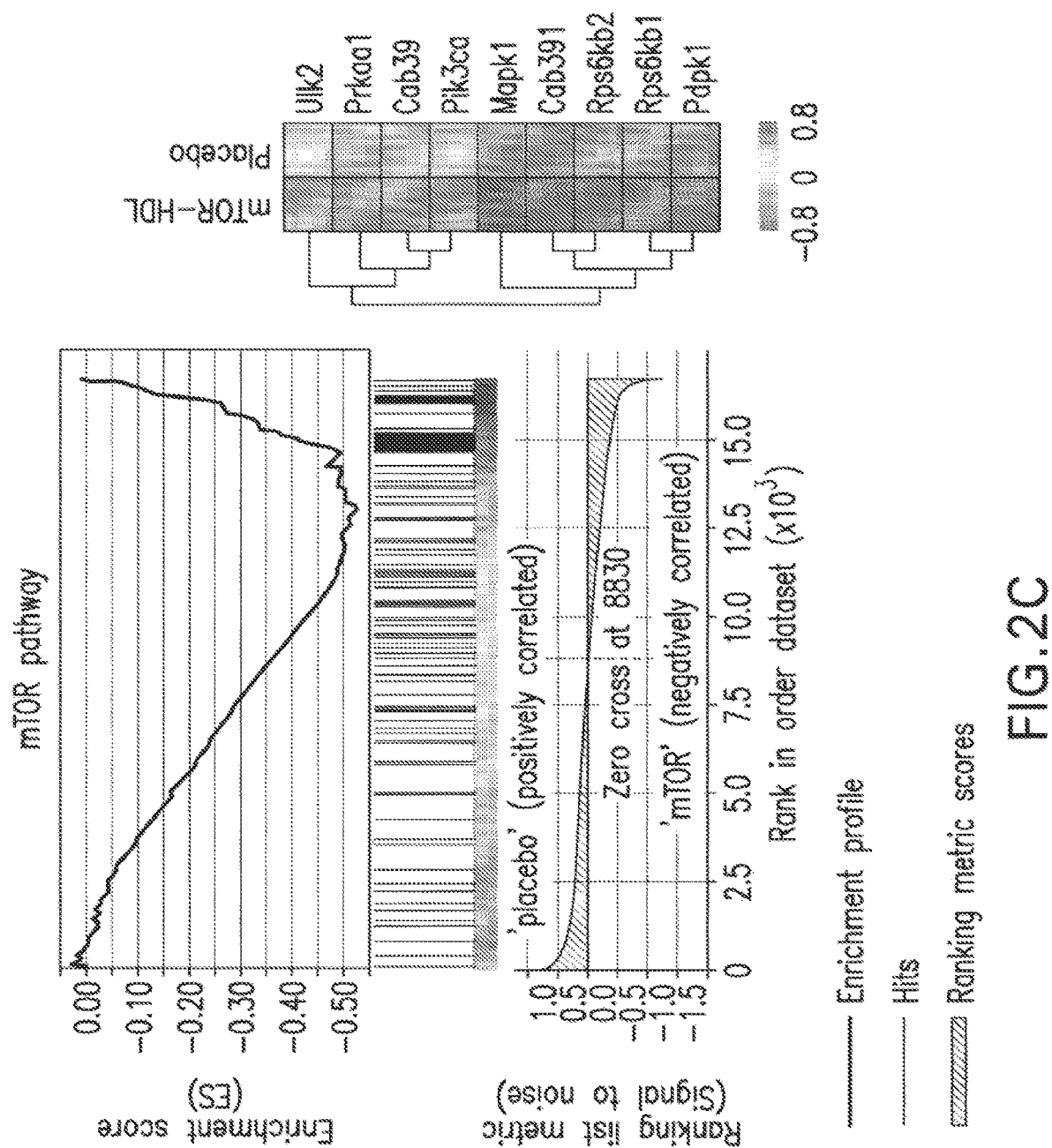

Molecular pathways targeted by mTOR-HDL nanoimmunotherapy were studied using Gene Set Enrichment Analysis (GSEA) of mRNA isolated from flow sorted MΦ from the allografts of either placebo or mTOR-HDL treated recipients. Gene array results indicated that the mTOR (FIG. 2C) pathway is negatively regulated by mTOR-HDL.

mTOR-HDL Treatment Favor the Induction of Transplantation Tolerance by Promoting the Development of Regulatory Ly-6C$^{lo}$ MΦ

Figure 3A:
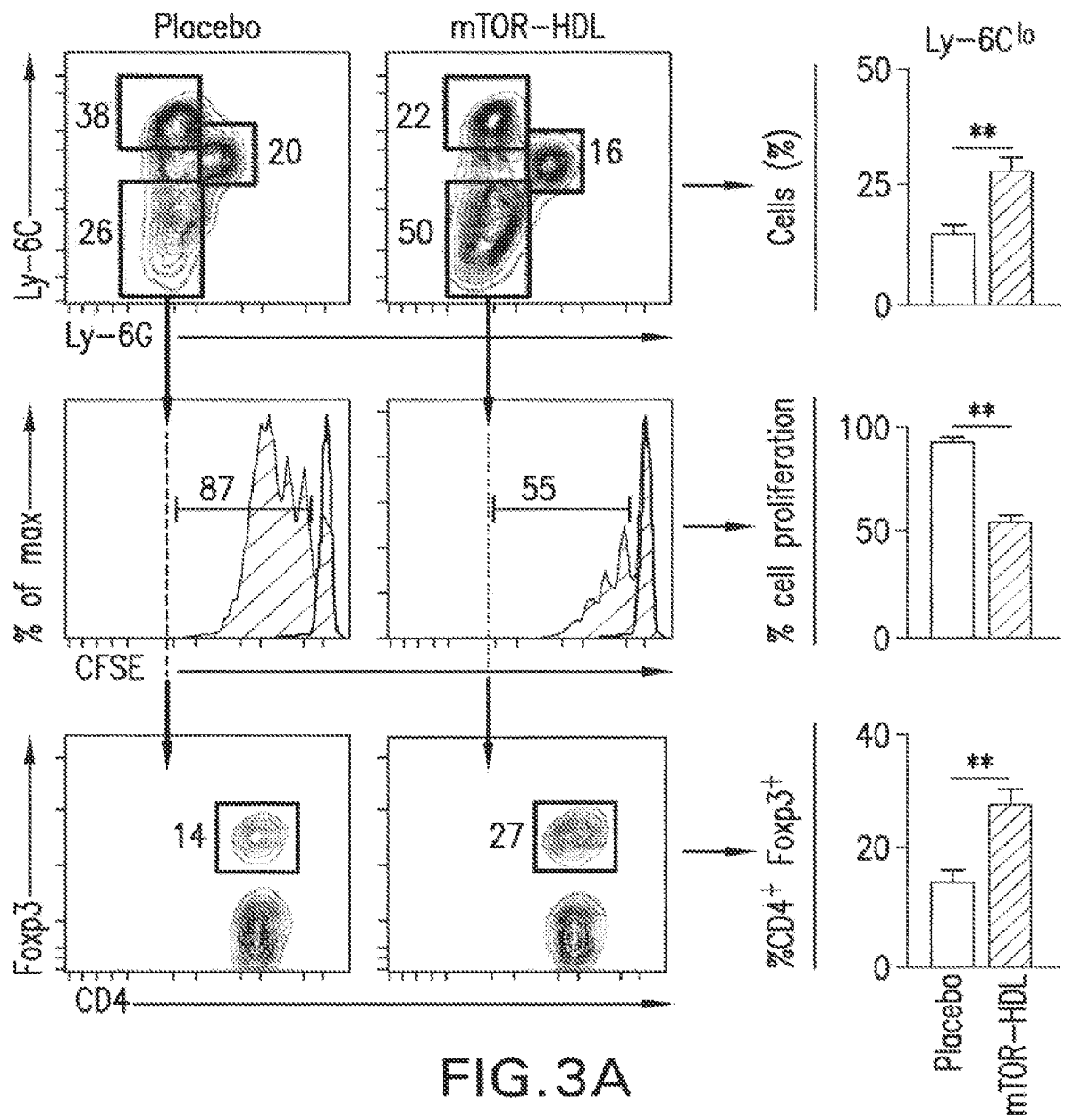
FIG. 3A-G are diagrams and graphs showing that HDL nanoimmunotherapy induces accumulation of regulatory macrophages and promotes graft acceptance.
Figure 10:
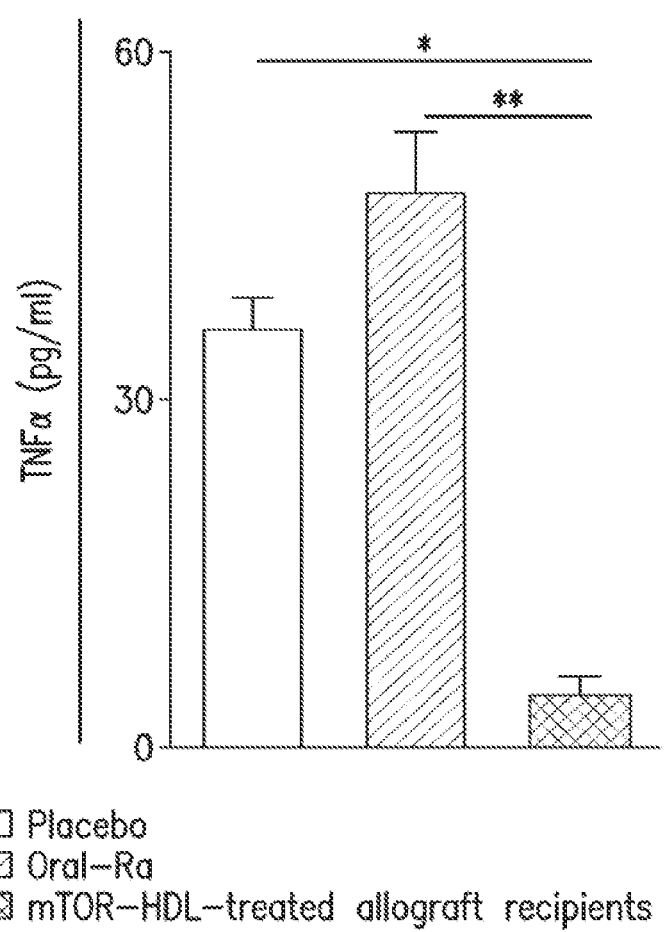
FIG. 10 is a graph showing TNF-α secretion 6 days post-transplantation in sera from placebo, Oral-Ra and mTOR-HDL-treated allograft recipients, as analyzed by ELISA.

Next, the suppressive function of graft-infiltrating Ly-6C$^{lo}$ Mo/MΦ allografts were evaluated in vitro. Ly-6C$^{lo}$ MΦ's regulatory suppressive function was assessed by the capacity to inhibit in vitro proliferation of carboxyfluorescein diacetate succinimidyl ester (CFSE)-labeled CD8+ T cells. The results of the present invention indicate that regulatory Ly-6C$^{lo}$ MΦ obtained from the allografts of mTOR-HDL treated recipient mice prevent T cell proliferation in vitro (FIG. 3A). The inventors also observed that, unlike Ly-6C$^{lo}$ MΦ obtained from the allografts of placebo recipient mice. Ly-6C$^{lo}$ MΦ obtained from the allografts of mTOR-HDL treated recipients expand immunosuppressive Foxp3-expressing T-regs (FIG. 3A). In agreement with these data, the inventors observed a significant increase in the number of allograft CD4$^+$CD25$^+$ T-cells (FIG. 3B; FIG. 10). This suggests that mTOR-HDL treatment may favor the induction of transplantation tolerance by promoting the development of regulatory Ly-6C$^{lo}$ MΦ.

mTOR-HDL Nanotherapy Prevents Potent T Cell Stimulation by Dendritic Cells

Since dendritic cells (DC) take up mTOR-HDL nanoparticles FIGS. 1F-G), the effects of mTOR-HDL on immune cell activation, antigen presentation and DC-mediated T cell stimulation were investigated. First, enzyme-linked immunosorbent assay (ELISA) were utilized to assess the expression of tumor necrosis factor alpha (TNF-α). These data indicate that mTOR-HDL treatment significantly reduces the serum TNF-α levels, as compared to placebo and Oral-Ra (FIG. 10; $P \leq 0.05$ and $P \leq 0.01$). Next, the expression of co-stimulatory and adhesion molecules that are upregulated during acute rejection[25,26] were examined. Flow cytometry indicates that both CD40 and CD54 molecules are significantly reduced in leukocytes from mTOR-HDL treated recipients compared to the placebo and Oral-Ra-treated recipients (FIG. 10). Using the Y-Ae monoclonal antibody (mAb), which recognizes a donor-derived I-E$^d$ peptide presented by recipient MHC class II I-A$^b$ molecules, mTOR-HDL's effects on antigen presentation were evaluated. Significantly fewer antigen-presenting Y-Ac$^+$ cells were observed in the para-aortic lymph nodes and spleens of mTOR-HDL-treated recipients than those from either placebo or Oral-Ra. Next, the capacity of DC obtained from mTOR-HDL recipients was evaluated to stimulate antigen-specific T cells in vitro. CD11c$^+$MHC-II$^+$ DC extracted from the spleens of placebo and mTOR-HDL-treated mice were used as initiators to stimulate a mixed lymphocyte reaction (MLR) in vitro. Antigen-specific TEa CD4$^+$ T cells were isolated as responders, as these T cells recognize the same I-E$^d$-I-A$^b$ complex of peptide and MHC as do Y-Ae mAb, labeled the cells with carboxyfluorescein succinimidyl ester (CFSE) and cultured with CD11c$^+$MHC-II$^+$ splenic DC as previously described[27]. The stimulatory properties of CD11c$^+$MHC-II$^+$ splenic DC were tested by measuring CFSE dilution in T cells by flow cytometry. These data indicate that DC from mTOR-HDL recipients are significantly less capable of stimulating naïve T cell proliferation in vitro than DC obtained from control mice. Next, the proliferative capabilities of T cells obtained from transplanted mice were tested. These data indicate that T cells from mTOR-HDL recipients are able to mount in vitro immune responses similar to T cells obtained from placebo rejecting mice. Overall, these results illustrate that mTOR-HDL nanoparticle treatment prevents DC-mediated graft-reactive T cell immune responses.

mTOR-HIDL Nanotherapy Promotes the Development of Suppressive Macrophages

Having determined that mTOR-HDL nanoparticles target Mo/MΦ (FIGS. 1F and 1G) and affect their tissue distribution), the functional properties of Ly-6C$^{lo}$ Mo/MΦ that accumulate in the allograft during tolerance induction, were tested. Donor heart allografts were harvested six days after transplantation and the myeloid compartment was analyzed by flow cytometry. By focusing on live CD45$^+$CD11b$^+$ recipient graft-infiltrating myeloid cells, we discerned three major populations based on differential expression patterns of Ly-6C$^{hi}$ Mo/MΦ, Ly-6C$^{lo}$ Mo/MΦ and Ly-6G neutrophils (FIG. 1D). Flow cytometric analysis confirmed the presence of more Ly-6C$^{lo}$ than Ly-6C$^{hi}$ Mo/MΦ in the allografts of mTOR-HDL-treated mice as compared to placebo recipients (FIG. 1D). There were no differences in Ly-6G neutrophil frequency between the groups.

Gene army characterization of Ly-6C$^{lo}$ macrophages that accumulate in the allografts of mTOR-HDL treated recipients revealed that the mTORC1 pathway is negatively regulated in these mice. This confirms that mTOR-HDL treatment targets graft-infiltrating macrophages.

Figure 11A:
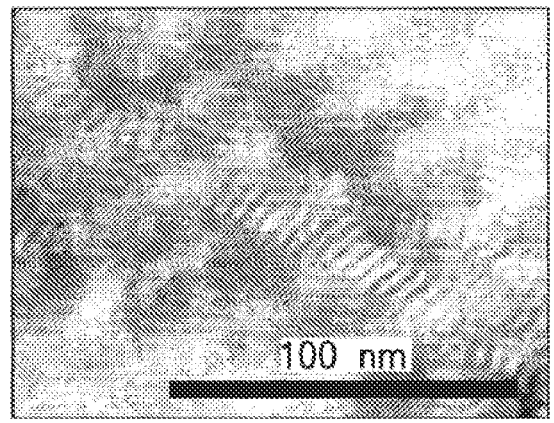
FIGS. 11A-B are transmission electron micrographs showing the discoidal morphology of TRAF6i-HDL. The nanoparticles had a mean hydrodynamic radius of 19.2±3.1 nm and a drug incorporation efficiency of 84.6±8.6%, as determined by DLS and HPLC respectively.
Figure 11B:
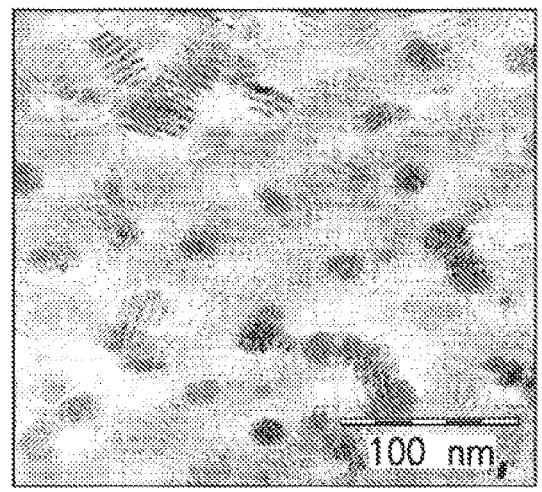

A comprehensive analysis of the costimulatory molecules that prevent successful organ transplantation revealed that mTOR-HDL treatment increased CD40 expression. In line with this observation, the inventors found agonistic CD40 mAb treatment to abrogate the prolonged allograft survival in mTOR-HDL treated recipients FIG. 3F). This suggests that CD40L expressing T cells may stimulate CD40 signaling in recipient MΦ, resulting in eventual graft loss. To suppress detrimental CD40 signaling, the inventors developed a second nanoimmunotherapy treatment consisting of a CD40-TRAF6 inhibitory HDL (referred to as CD40-HDL or TRAF6i-HDL; FIG. 11A-B). The small molecule inhibitor CD40-TRAF6 is directed against the binding domain of CD40 on TRAF6 and blocks CD40 signaling, resulting in Ly6C& inflammatory macrophage polarization towards an anti-inflammatory phenotype.

mTOR-HDL Prolongs Allograft survival Indefinitely

Lastly, nanoimmunotherapy treatment's capacity to prevent organ rejection and prolong allograft survival was evaluated. Balb/c (H2$^d$) donor cardiac allografts were transplanted into fully allogeneic C57Bl/6 (H2) recipients treated with: (1) placebo. (2) Oral-Ra, (3) mTOR-HDL, (4) TRAF6i-HDL, or (4) mTOR-HDL+TRAF6i-HDL. To assess graft survival, recipients underwent abdominal palpation until cardiac contractions completely ceased. The present data indicate that mTOR-HDL nanotherapy dramatically prolongs graft survival with more than 85% allograft survival over a 50-day period (FIG. 3G) By contrast, the oral rapamycin treatment only prolonged allograft survival by 35% during the same period (P≤0.01, P≤0.01). This is a remarkable result, especially considering the regimen involved only three doses during the first week post-transplantation.

Figure 3B:
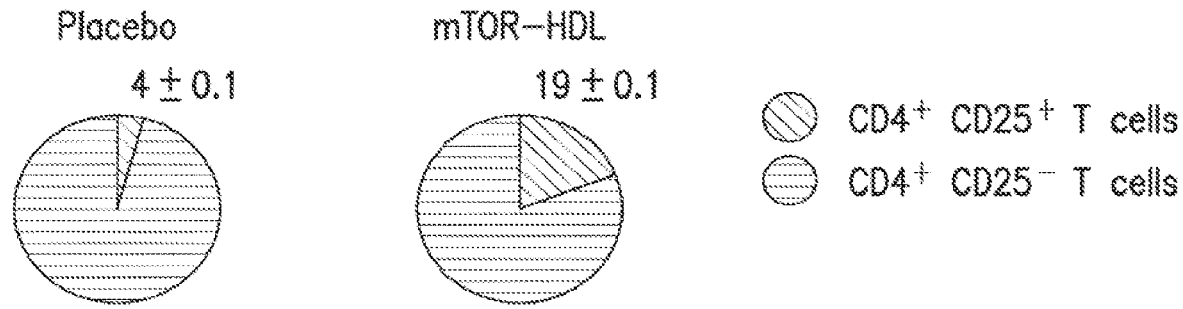
Figure 3C:
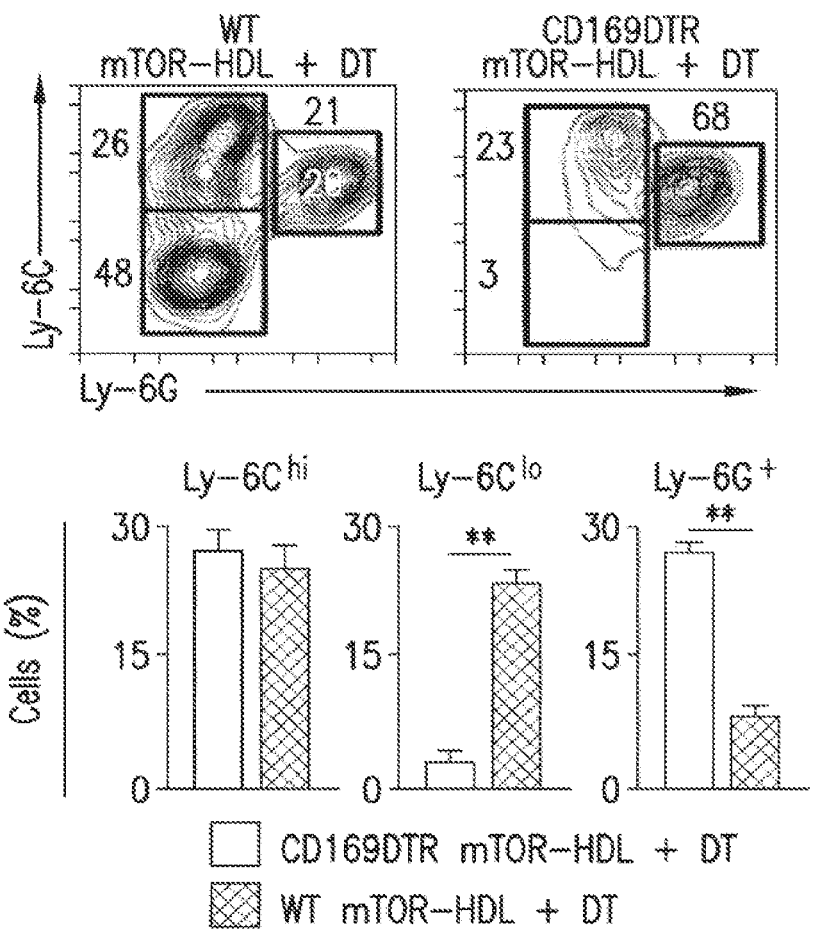
Figure 3D:
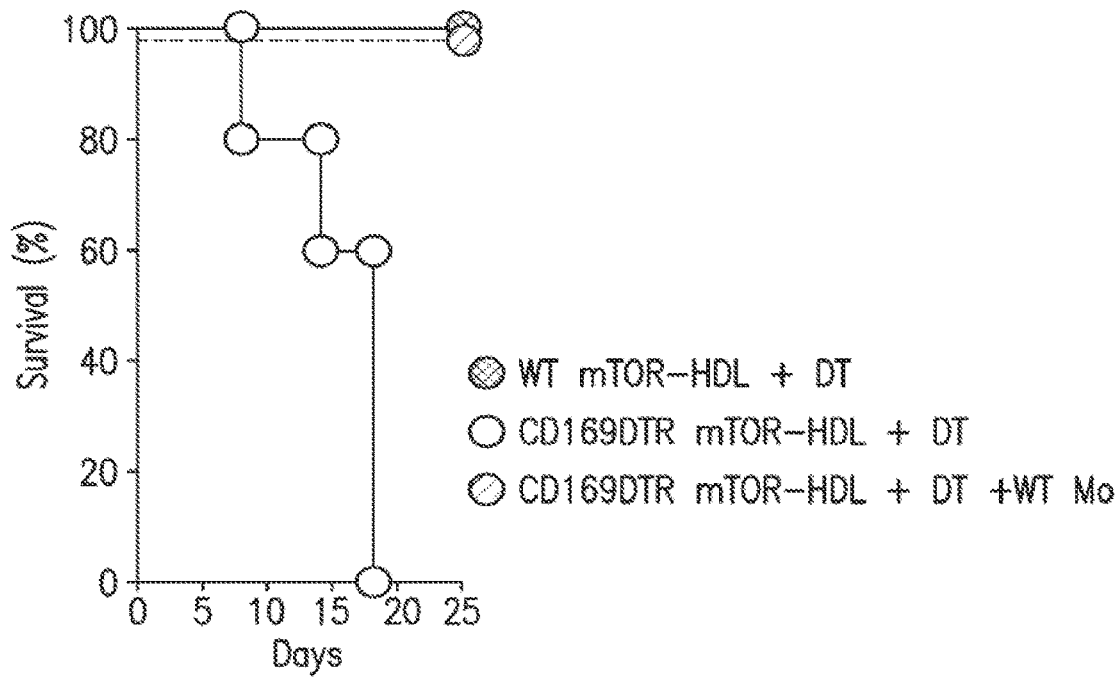
Figure 3E:
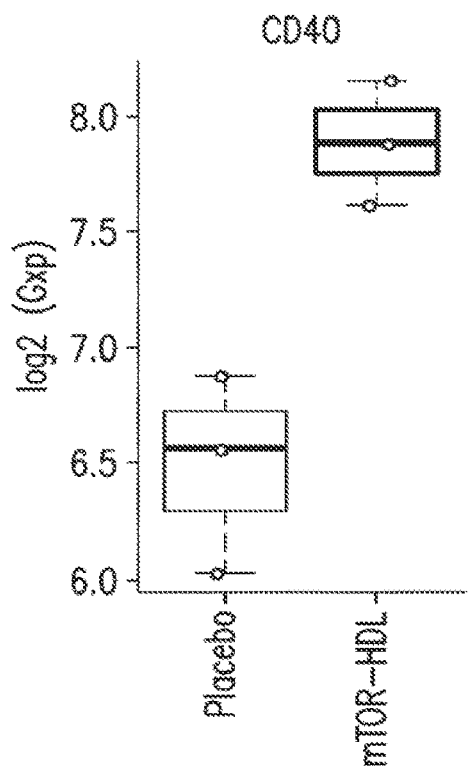
Figure 3F:
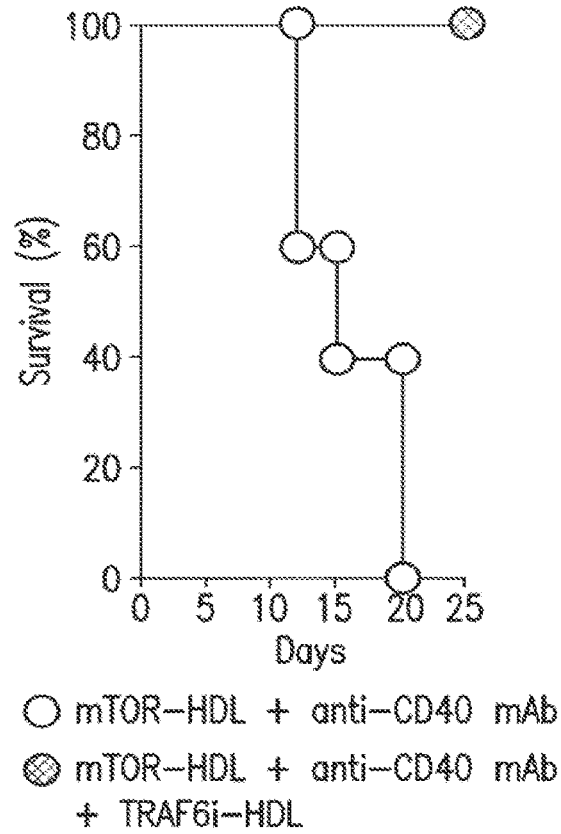
Figure 3G:
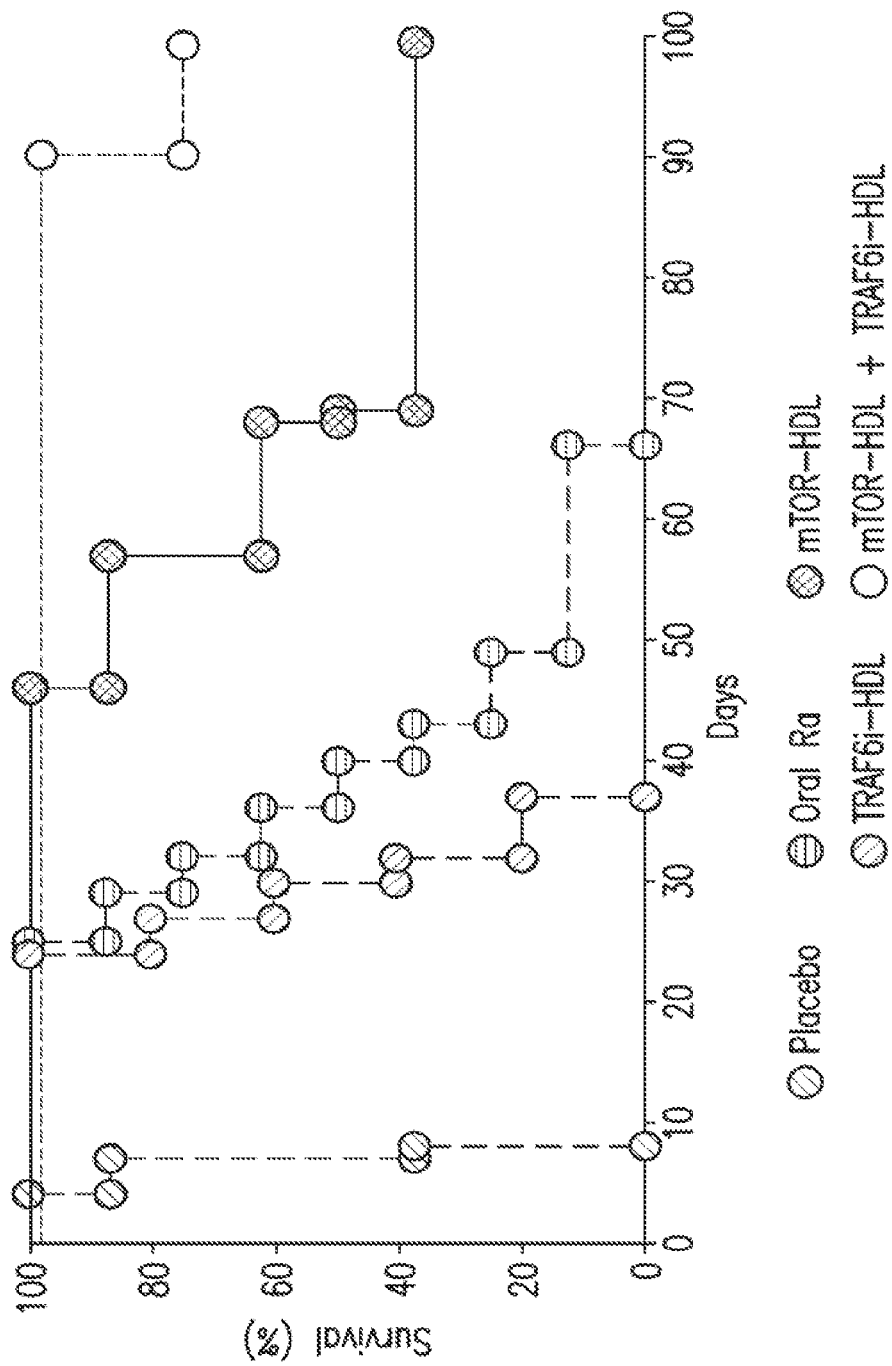
Figure 13A:
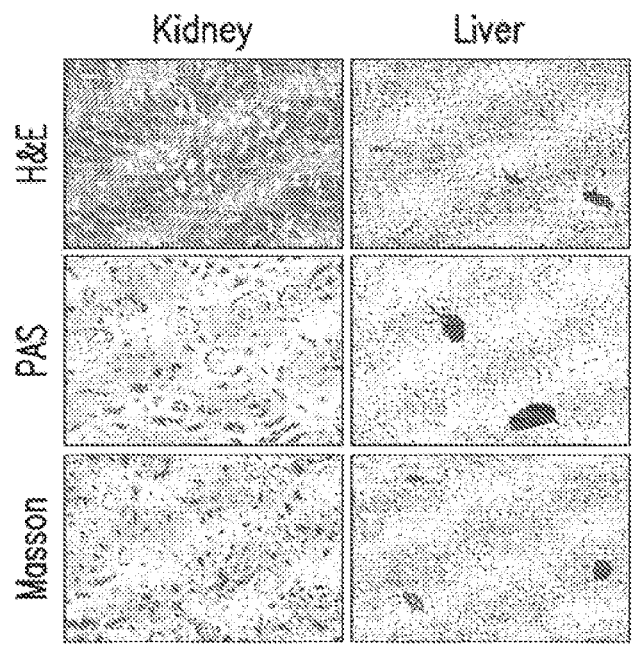
FIGS. 13A-B are graphs showing kidney and liver images (FIG. 13A) and heart immunohistochemistry (IHC) (FIG. 13B) for toxicity evaluation. The kidney and liver representative images of IHC for hematoxylin/eosin (H&E), Periodic acid-Schiff (PAS) and Masson's Trichrome (Masson) show no signs of toxicity. Kidney and liver from mTor/TRAF6i-HDL treated recipients were collected at day 100 after transplantation (n=4; magnification X200).
Figure 13B:
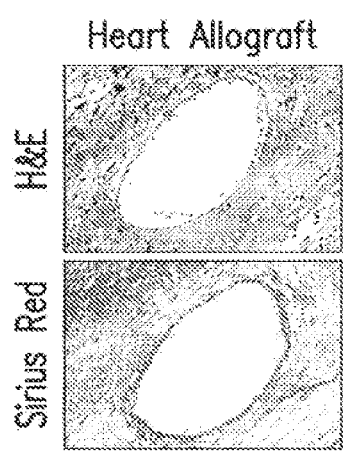

As a secondary endpoint, we evaluated the histology of the allografts 100 days after combined treatment (FIGS. 13A-B). FIG. 13B shows mild circumferential inflammation without arteritis and no signs of intimal hyperplasia. Mouse aortic segments did not exhibit any histological alteration with no intimal thickening and no signs of chronic allograft vasculopathy (CAV). Furthermore, the inventors evaluated a combined treatment regimen involving three injections of both mTOR-HDL and TRAF6i-HDL within the first five days post transplantation using the heart allograft model. As shown in FIG. 3G, combined mTOR-HDL/TRAF6i-HDL treatment promotes organ transplant synergistically, resulting in a more than 70% survival over 100 days post-transplantation, significantly outperforming mTOR-HDL and TRAF6i-HDL monotherapies.

The timing of treatment can vary and can commence either before the transplantation, concomitant with the transplantation, or following transplantation. In one embodiment, the mTOR-HDL or combined mTOR-HDL/TRAF6i-HDL treatment is initiated 1-2 days before organ transplantation.

To test whether in vitro suppressive Ly-6C$^{lo}$ Mo/MΦ mediate prolonged graft survival in mTOR-HDL-treated recipients, the inventors depleted Ly-6C$^{lo}$ Mo/MΦ in vivo, as recently described[9]. Briefly, Balb/c (H2$^d$) donor cardiac allografts were transplanted into fully allogeneic CD169 diphtheria toxin (DT) receptor (DTR) (H12$^b$) recipient mice on the day of transplantation to deplete recipient Ly-6C$^{lo}$ macrophages. Graft-infiltrating leukocytes were examined by flow cytometry six days after transplantation to confirm the specific depletion of Ly-6C$^{lo}$ in vitro suppressive macrophages (FIG. 3B). Subsequent graft survival experiments showed that Ly-6C$^{lo}$ Mo/MΦ depletion resulted in graft rejection by day 15 (12.3±1.8) despite mTOR-HDL treatment (FIG. 3D). Adoptive transfer of wild-type monocytes restored allograft survival, demonstrating that the nanoimmunotherapy exerts its effects through regulatory MΦ. These experiments suggest that mTOR-HDL treatment stimulates in vivo development of regulatory Ly-6C$^{lo}$ macrophages that prevent T cell-mediated immune responses and thereby promotes prolonged allograft survival.

Figure 12A:
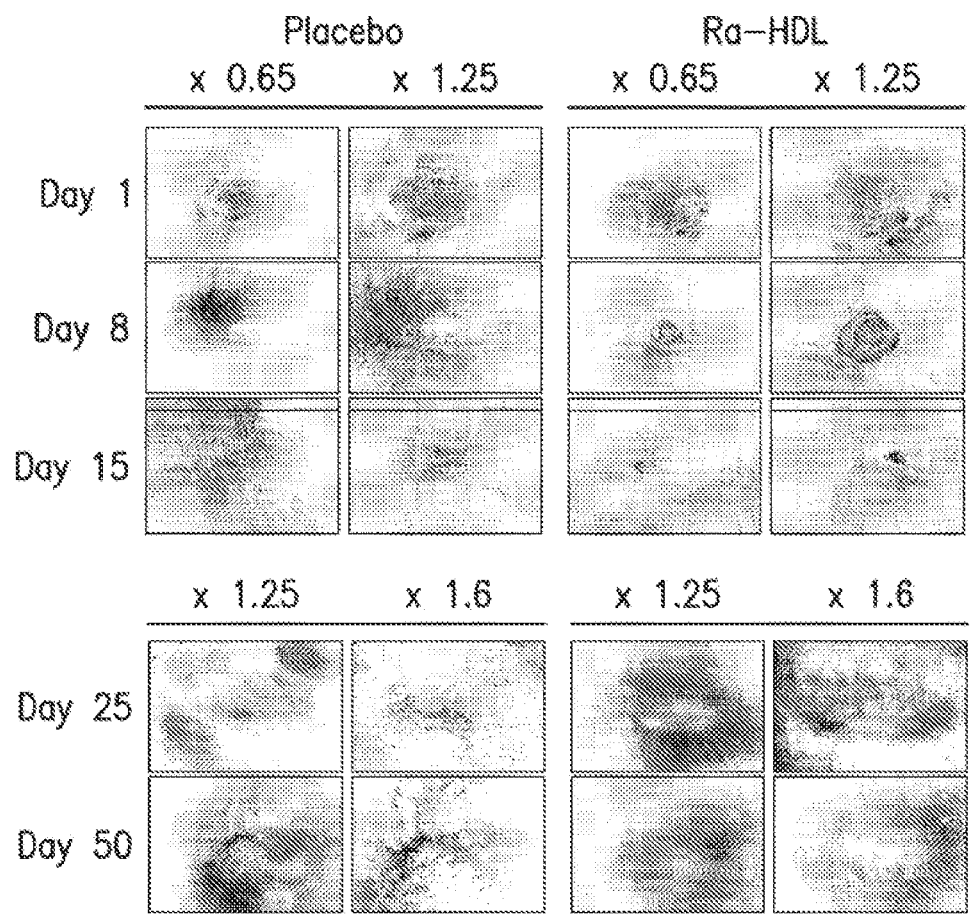
FIGS. 12A-B are images and a Kaplan-Meier curve showing that mTOR-HDL nanoimmunotherapy dramatically prolongs skin allograft survival.
Figure 12B:
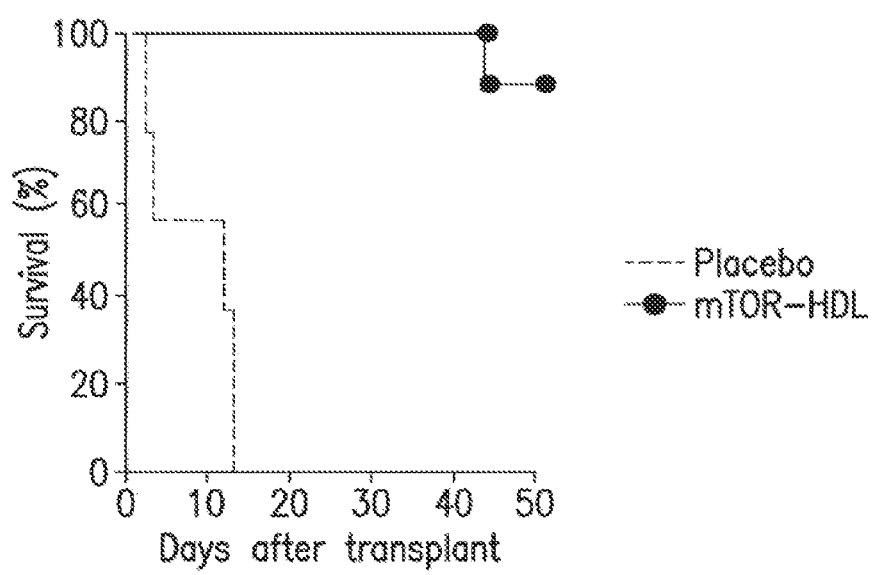

To further investigate the general therapeutic applicability of mTOR-HDL, mTOR-HDL nanotherapy described here was applied to a fully allogeneic skin transplant model in which rejection was macroscopically monitored (FIGS. 12A AND 12B). Using the same three-dose regimen, the mTOR-HDL nanomedicine treatment dramatically enhanced graft survival. The mean survival time significantly increased in mTOR-HDL-treated recipients, with more than 75% survival at day 50; the placebo group, on the other hand, had a 100% rejection rate (P≤0.01) (10.5±2.9 days). Overall, these experiments and results show that mTOR-HDL nanotherapy prevents DC-mediated T cell stimulation, promotes Ly-6C$^{lo}$ Mo/MΦ development and dramatically prolongs allograft survival.

FIGS. 13A-B are graphs showing toxicity associated with Oral-Ra compared with mTOR-HD treatment. Recipient mice either received the mTOR-HDL treatment regimen or were given an Oral-Ra treatment for which the dose was increased to achieve the same therapeutic outcome (n=4, grey) or (n=4, black), mTOR-HDL has no significant effects on blood urea nitrogen (BUN, shown in FIG. 13A) or serum creatinine (shown in FIG. 13B), but kidney toxicity parameters show statistical differences between Oral-Ra and mTOR-HDL, while no differences between syngeneic and mTOR-HDL recipients 30 days after infusion were observed (ANOVA *P≤0.05,**P0.0).

Histology sections from kidneys, stained by H&E, PAS and Masson Trichrome and examined by a renal pathologist show no significant changes in the three compartments of kidney parenchyma (FIG. 13A). There is normal appearing glomeruli, with no evidence of glomerulosclerosis. The tubules show no significant atrophy or any evidence of epithelial cell injury including vacuolization, loss of brush border or mitosis. Arteries and arterioles show no evidence of intimal fibrosis or arteriolar hyalinosis, respectively. Liver sections stained by H&E, PAS and Masson Trichrome and examined by a liver pathologist demonstrate normal acinar and lobular architecture. There is no evidence of inflammation or fibrosis in the portal tract and hepatic parenchyma. Hepatocytes are normal with no evidence of cholestasis, inclusions or apoptosis (FIG. 13A). In FIG. 13B the section shows mild circumferential inflammation without arteritis and no signs of intimal hyperplasia. Mouse aortic segments did not exhibit any histological alteration with no intimal thickening, and no signs of chronic allograft vasculopathy (CAV).

Discussion

Transplant patients are treated with immunosuppressive drugs to avoid organ rejection[30]. Immunosuppressants target the adaptive immune system and have serious side effects[31,32]. Current transplant immunology research seeks to develop novel tolerogenic protocols using different experimental transplantation models. Combining basic immunology with innovative nanomedicine is a promising new approach to encourage immune tolerance. The use of animal models plays an essential role in this research. Unfortunately, while some experimental tolerogenic protocols can induce indefinite allograft survival in mice and primates[31,32], thromboembolic complications have prevented these methods from being translated into clinical treatments[35]. Consequently, them is an ongoing need for alternative approaches to immune regulation, such as targeting the innate immune system, to prevent transplant rejection[11,12,36].

In the current study, the data demonstrate that conservatively-dosed HDL-encapsulated rapamycin prolongs graft survival. This indicates that only encapsulated rapamycin— i.e. not the free form—may be used to induce immunological tolerance, as recently described[37]. The data also mechanistically show that mTOR-HDL decreases leukocytes in the blood, spleen and allograft. Reduced leukocyte adhesion and migration is associated with better graft survival, in agreement with previous studies[38,41]. More specifically, significantly lower Mo/MΦ and neutrophil counts accompanied by less myeloid cell infiltration in allografts were observed. In contrast to the present mTOR-HDL nanotherapy approach which targets the myeloid compartment, 95% of absorbed oral rapamycin binds to erythrocytes[42]. Therefore, the present nanotherapy delivery strategy presents an innovative way to dramatically increase the drug's bioavailability.

In association with its capacity to decrease cellular infiltration in the transplanted organ, in vivo mTOR-HDL administration markedly reduces production of pro-inflammatory molecules and diminishes the ability of DC to induce T cell proliferation. These results accord with a previous report showing that DC conditioned in vitro with rapamycin reduce pro-inflammatory mediators and prolong allograft survival[43]. Additionally, these data indicate that mTOR-HDL nanotherapy further affects DC by inhibiting their stimulatory function, thereby suggesting alloantigen-specific T cell activation can be therapeutically modulated. The present data also demonstrate that mTOR-HDL treatment reduces alloantigen presentation to CD4$^+$ T cells. These immune regulatory effects are of pivotal importance during transplantation, in which antigen-presenting cells mediate the specific alloreactivity against the transplanted organ[44].

The present data illustrate that mTOR-HDL treatment mediates the accumulation of suppressive macrophages that inhibit cytotoxic T cell responses. In addition, Ly-6C$^{lo}$ macrophages from HDL-treated recipients expand Foxp3$^+$ Treg in vitro and correlate with intra-graft Foxp3$^+$ Treg accumulation in vivo. Regulatory Ly-6C$^{lo}$ macrophage accumulation in the transplanted organ appears to be critical to prolonged allograft survival as mediated by TOR-HDL, since depleting Ly-6C$^{lo}$ macrophages prevents tolerance induction despite mTOR-HDL treatment. These results are consistent with studies showing that Ly6C$^{lo}$ macrophages inhibit cytotoxic T cell proliferation, mediate Treg expansion and promote transplantation tolerance[9]. The results demonstrate that HDL-based nanoparticles represent novel a therapeutic approach to develop drug delivery systems that target macrophages in vivo.

Collectively, these data show that HDL nanoparticle technology effectively delivers immunosuppressive drugs to the innate immune system. mTOR-HDL prevents DC activation, promotes the regulatory macrophage development and induces indefinite allograft survival. The mTOR-HDL technology is an innovative, effective, and a potentially translational therapeutic approach that targets innate immune cells to induce long-term allograft survival. Clinical testing and implementation of an optimized GMP protocol will confirm long-term safety and efficacy. As mTOR-HDL combines existing FDA approved agents, its development— or the development of HDL nanoparticles systems that release other FDA-approved immunosuppressive agents—may have an immediate path to translation.

Materials and Methods

Nanoparticle Synthesis

The present targeted approach delivers the drug rapamycin using a novel synthetic high-density lipoprotein nanoparticle platform. mTOR-HDL nanoparticles were synthesized using a modified lipid film hydration method. Briefly, 1,2-dimyristoyl-sn-glycero-3-phosphatidylcholine (DMPC), 1-myristoyl-2-hydroxy-sn-glycero-phosphocholine (MHPC) (both purchased from Avanti Polar Lipids) and rapamycin (Selleckchem) were dissolved in a chloroform/methanol (10:1 v/v) mixture at a 3:1:0.5 weight ratio. After evaporating the solvents, human APOA1 in PBS was added to hydrate the lipid film, in a phospholipid to APOA1 5:1 weight ratio and left to incubate for 20 minutes in an ice-bath. The resulting mixture was homogenized using a probe sonicator in an ice-bath for 15 minutes to yield mTOR-HDL nanoparticles. mTOR-HDL was washed and concentrated by centrifugal filtration using 10 kDa molecular weight cut-off (MWCO) filter tubes. Aggregates were removed using centrifugation and filtration (0.22 μm). Oral rapamycin solution (Oral-Ra) consisted of 4% ethanol, 5% PEG300 and 5% TWEEN80 in PBS, while intravenous rapamycin solution (i.v.-Ra) included 4% ethanol and 5% TWEEN80 in PBS. The animals received oral doses or intravenous tail injections (for mTOR-HDL or i.v.-Ra) at a rapamycin dose of 5 mg/kg on the day of transplantation as well as days two and five post transplantation.

CD40-HDL nanoparticles were synthesized according to a similar procedure as described above. DMPC, MHPC and the TRAF6-inhibitor (2E)-1-phenyl-3-(2,5-dimethyl-anilino)-2-propen-1one] were dissolved in a chloroform/methanol mixture (10:1 v/v) at a 8.7:1:0.6 weight ratio, and then dried under vacuum to create a thin lipid film. PBS containing APOA1 was added to the lipid film, in a phospholipid to APOA1 9.5:1 weight ratio, and left to incubate on ice for 3 hours until the film was hydrated and a homogenous solution was formed. The solution was then sonicated for 1 hour to form CD40-HDL, nanoparticles. Subsequently, the solution was purified by multiple centrifugation and filtration steps.

Mice

Female C57BL/6J (16 WT. H-2b). BALB/c (H-2d) mice were purchased from the Taconic Laboratory, 8 week old C57BL/6J (Foxp3tm1F1v/J) mice were purchased from The Jackson Laboratory. The C57BL/6J CD169$^{DTR}$ mice were from Masato Tanaka (Kawaguchi, Japan). C57BL/6J CD4$^+$ transgenic TEa mice that recognize a peptide representing residues 52 to 68 of the I-Eα chain (Eα peptide) bound to class II I-A$^b$ molecules were from Alexander Rudensky (New York, USA). Animals were enrolled at 8 to 10 weeks of age (body weight, 20-25 g). All experiments were performed with 8 to 12 week old female matched mice in accordance with protocols approved by the Institutional Animal Care and Utilization Committee.

Vascularized Heart Transplantation

BALB/c hears were transplanted as fully vascularized heterotopic grafts into C57BL/6 mice as previously described[45]. Hearts were transplanted into recipients' peritoneal cavities by establishing end-to-side anastomosis between the donor and recipient aortae and end-to-side anastomosis between the donor pulmonary trunk and the recipient inferior vena cava. Cardiac allograft survival was subsequently assessed through daily palpation. Rejection was defined as the complete cessation of cardiac contraction and was confirmed by direct visualization at laparotomy. Graft survival was compared among groups using Kaplan-Meier survival analysis.

Micro-PET/CT Imaging and Biodistribution Studies

Mice (n=6; 3 with heart transplants and 3 with skin grafts) [weight: 18.8±1.0 g]) were injected with $^{89}$Zr-mTOR-HDL (0.17±0.01 mCi, ~0.25 mg APOA 1) in 0.2 mL PBS solution via their lateral tail vein. At 24 h, animals were anesthetized with isoflurane (Baxter Healthcare. Deerfield, IL, USA)/oxygen gas mixture (2% for induction, 1% for maintenance), and a scan was then performed using an Inveon PET/CT scanner (Siemens Healthcare Global, Erlangen, Germany). Whole body PET static scans, recording a minimum of 30 million coincident events, were performed for 15 min. The energy and coincidence timing windows were 350-700 keV and 6 ns, respectively. The image data were normalized to correct for PET response non-uniformity, dead-time count losses, positron branching ratio and physical decay to the time of injection, but no attenuation, scatter or partial-volume averaging correction was applied. The counting rates in the reconstructed images were convened to activity concentrations (percentage injected dose [% ID] per gram of tissue) using a system calibration factor derived from imaging a mouse-sized water-equivalent phantom containing $^{89}$Zr. Images were analyzed using ASIPro VMTM software (Concorde Microsystems, Knoxville, TN, USA). Whole body standard low magnification CT scans were performed with the X-ray tube setup at a voltage of 80 kV and current of 500 μA. The CT scan was acquired using 120 rotational steps for a total of 220 degrees yielding an estimated scan time of 120 s with an exposure of 145 ms per frame. Immediately after the PET/CT scan, animals were sacrificed and tissues of interest-kidney, heart, liver, spleen, blood, bone, skin, and muscle-were collected, weighed and counted on a Wizard2 2480 automatic gamma counter (Perkin Elmer. Waltham, MA) to determine radioactivity content. The values were decay-corrected and converted to percentage of injected dose per gram (% ID/g). To determine radioactivity distribution within the transplanted hearts, the native and grafted specimens were placed in a film cassette against a phosphorimaging plate (BASMS-2325, Fujifilm. Valhalla, NY) for 4 hours at −20° C. The plate was read at a pixel resolution of 25 μm with a Typhoon 7000IP plate reader (GE Healthcare. Pittsburgh, PA). The images were analyzed using Images software.

Isolating Graft-Infiltrating Leukocytes

Mouse hearts were rinsed in situ with HBSS with 1% heparin. Explanted hearts were cut into small pieces and digested for 40 minutes at 37° C. with 400 U/ml collagenase IV (Sigma-Aldrich), 10 mM HEPES (Cellgro) and 0.01% DNase 1 (MP Biomedicals) in HBSS (Cellgro). Digested suspensions were passed through a nylon mesh and centrifuged, and the cell pellet was re-suspended in complete HBSS, stained and analyzed by flow cytometry (BD LSR-II; BD Biosciences).

Flow Cytometry and Cell Sorting

For myeloid cell staining, fluorochrome-conjugated mAbs specific to mouse CD45 (clone 30-F11). CD11b (clone MI/70), CD11c (clone N418), F4/80 (clone CI:A3.1). Ly-6C (clone HK1.4) and corresponding isotype controls were purchased from eBioscience. Ly-6G (clone 1A8) mAb was purchased from Biolegend. F4/80 (clone CI:A3.1) was purchased from AbD Serotec. For T cell staining, antibodies against CD45 (clone 30-F11), CD3 (clone 2C11), CD4 (clone GK1.5), CD8 (clone 53-6.7). CD25 (clone PC61.5), CD40 (clone 1C10) and CD54 (clone YN1/1.7.4) were purchased from eBioscience. The absolute cell counting was performed using count bright beads (Invitrogen). To detect antigen presentation, the Y-Ae mAb was purchased from eBioscience. Flow cytometric analysis was performed on LSR II (BD Biosciences) and analyzed with FlowJo software (Tree Star, Inc.). Results are expressed as percentage of cells staining or cells counting (cells per milliliter) above background. mAbs were titered at regular intervals during the course of these studies to ensure the use of saturating concentrations. To purify graft-infiltrating myeloid cells, donor heart single cell suspensions were sorted with an InFlux cell sorter (BD) to achieve >96% purity at the Flow Cytometry Shared Resource Facility at Icahn School of Medicine at Mount Sinai.

Mixed Lymphocyte Reaction

Spleens of antigen-specific TEa (H-2$^b$) mice were gently dissociated into single-cell suspensions, and red blood cells were removed using hypotonic ACK lysis buffer. Splenocytes were labeled with CFSE cell proliferation marker at 5

μM concentration (molecular probes from Invitrogen) followed by staining with anti-CD4 mAb for 30 minutes on ice. Responder CFSE$^+$CD4$^+$ T cells were sorted using FACS Aria II sorter (BD Biosciences) with a purity of >98%. Splenocytes from mTOR-HDL- and placebo-treated recipients were enriched for CD11c$^+$ cells using the EasySep Mouse CD11c positive selection Kit (StemCell). Enriched CD11c$^+$ splenocytes were stained with anti-mouse CD11c mAb for minutes on ice. CD11c$^+$ cells were sorted using FACS Aria II sorter (BD Biosciences) and then used to stimulate responder CFSE$^+$CD4$^+$ T cells. Cells were cultured for 4 days at 37° C. in a 5% $CO_2$ incubator, and CFSE$^+$CD4$^+$ T cells proliferation was measured by flow cytometric analysis of CFSE dilution on CD4$^+$ T cells.

In Vitro Suppression Assay

Spleens of C57BL/6 (H-2$^h$) mice were gently dissociated into single-cell suspensions, and red blood cells were removed using hypotonic ACK lysis buffer. Splenocytes were labeled with CFSE at 5 μM concentration (molecular probes from invitrogen) followed by staining with anti-CD8 mAb for 30 minutes on ice. Responder CFSE$^+$CD8$^+$ T cells were sorted using FACS Aria II (BD Biosciences) with >98% purity. CFSE$^+$CD8$^+$ T cells were used together with anti-CD3/CD28 microbeads as stimulators. Stimulated CFSE$^+$CD8$^+$ T cells were cultured with graft-infiltrating Ly-6C$^{lo}$ macrophages, mTOR-HDL or placebo for 72 hours at 37° C. in a 5% $CO_2$ incubator. T cell proliferation was measured by flow cytometric analysis of CFSE dilution on CD8$^+$ T cells.

Treg Expansion Assay

Spleens of C57BL/6-Foxp3tm1F1v/J (H-2$^b$) mice were gently dissociated into single-cell suspensions, and red blood cells were removed using hypotonic ACK lysis buffer. Splenocytes were stained with anti-CD4 mAb for 30 minutes on ice. Responder CD4$^+$ were sorted using FACS Aria II (BD Biosciences) with a purity of >98%. CD4$^+$ T cells were used together with anti-CD3/CD28 microbeads as stimulators. Stimulated CD4$^+$ T cells were cultured with graft-infiltrating Ly-6C$^{lo}$ macrophages, mTOR-HDL or placebo for 72 hours at 37'C in a 5% $CO_2$ incubator. Treg expansion was measured by flow cytometric analysis of Foxp3-RFP on CD4$^+$ T cells.

Microarray.

Graft infiltrating recipient Ly-6C$^{lo}$ macrophages were sorted from mTOR-HDL treated and placebo rejecting recipients at day 6 after transplantation. Cells were sorted twice with a FACS Aria II sorter (BD Biosciences) to achieve >98% purity. Microarray analysis of sorted cells was performed with a total of 6 Affymetrix Mouse Exon GeneChip 2.0 arrays were run in triplicate with the samples of interest. Raw CEL file data from Affymetrix Expression Console were background corrected, normalized, and summarized using RMA. The summary expression scores were computed at the transcript meta-probeset level using annotation files supplied by the manufacturer. Gene expression was filtered based on IQR (0.25) filter using gene filter package. The log 2 normalized and filtered data (adjusted P <0.05) was used for further analysis. Gene signature comparisons were performed between intra-graft Ly6C$^{lo}$ macrophages from mTOR-HDL and placebo treated recipients. GSEA was performed using GSEA version 17 from Gene pattern version 3.9.6. Parameters used for the analysis were as follows. Gene sets c2.cp.biocarta.v5.1.symbols.gmt; c2.cp.kegg.v5.1.symbols.gmt; c2.cp.reactome.v5.1.symbols.gmt; c6.all.v5.1.symbols.gmt (Oncogenic Signatures), c7.all.v5.1.symbols.gmt (Immunologic signatures); and h.all.v5.symbols.gmt (Hallmarks) were used for running GSEA and 1000 permutations were used to calculate p value and permutation type was set to gene set. Each gene set was run separately. All basic and advanced fields were set to default. To select the significant pathways from each gene set result, fdr q-value of 0.25 was set as cutoff. Only genes that contributed to core enrichment were considered.

In Vivo Macrophage Depletion

To deplete CD169-expressing Ly-6C$^{lo}$ macrophages, heterozygous CD169-DTR recipients were injected intraperitoneally with 10 ng/g body weight of DT (Sigma-Aldrich) 24, 48 and 72 hours after transplantation[46].

Statistical Analyses

Results are expressed as mean±SEM. Statistical comparisons between 2 groups were evaluated using the Mann Whitney tests. Kaplan-Meier survival graphs were performed, and a log-rank comparison of the groups calculated P values. A value of P≤0.05 was considered statistically significant. IBM SPSS statistics 22 were utilized for statistical analysis.

Near Infrared Fluorescence Imaging

C57/B6 wild type mice received a single intravenous injection of 5 mg/kg mTOR-HDL labeled with either DiR dye or phosphate-buffered saline (PBS). After 24 hours, the mice were sacrificed and perfused with PBS. Liver, spleen, lung, kidney, heart and muscle tissues were collected for NIRF imaging. Fluorescent images were acquired with the IVIS 200 system (Xenogen) with a 2 second exposure time using a 745 nm excitation filter and a 820 nm emission filter. Both the average radiant efficiency within each tissue and the ratio to control have been quantified.

Radiolabeling mTOR-HDL Nanoparticles $^{89}$Zr-mTOR-HDL was prepared according to previously described procedures [15]. Briefly, ready-to-label mTOR-HDL was obtained by adding 1 mol % of the phospholipid chelator 1,2-Distearoyl-sn-glycero-3-phosphoethanolamine-1,8-Diazafluoren-9-one (DSE-DFO) [44] at the expense of 1,2-dimyristoyl-sn-glycero-3-phosphocholine (DMPC) in the initial formulation. Radiolabeling with $^{89}$Zr was achieved by reacting the DFO-bearing nanoparticles with $^{89}$Zr-oxalate in PBS (pH=7.1) at 37° C. for 1 h. $^{89}$Zr-mTOR-HDL was isolated by centrifugal filtration using 10 kDa molecular weight cut-off tubes. The radiochemical yield was 75±2% (n=2).

Biodistribution of $^{89}$Zr-mTOR-HDL

Immediately after the PET/CT scan, mice were sacrificed and tissues of interest (blood, heart, kidneys, lungs, liver, spleen, bone, skin, muscle and graft) harvested, blotted and weighed before radioactivity counting on a Wizard2 2480 automatic gamma counter (Perkin Elmer, Waltham, MA. USA). The radioactivity content was then converted to radioactivity concentration and expressed as percentage of injected dose per gram of tissue (% ID/g).

Enzyme-Linked Immunosorbent Assay (ELISA)

Blood was harvested at day 6 post-transplantation, and sera were purified using 1.1 ml Z-Gel microtubes (Sarstedt) after incubation at room temperature and a brief centrifugation. TNF-α secretion in sera was assessed by ELISA (eBiosciences) according to the manufacturer protocol (n=4 in each group). Allograft cytokine production was determined in supernatants using commercial ELISA kits for IL-6 and TNFα according to the manufacturer guidelines (R&D systems).

Ultrasound Imaging

Cardiac allograft transplant rate (beats per minute, BPM) was monitored using a short axis cross sectional B-Mode image of the transplanted heart, with M-mode cursor line through its largest dimension and tracing of the left ventricular wall.

Skin Transplantation

Full-thickness trunk skin allografts were placed as previously described 1421. Skin was harvested from BALB/C, cut into 0.5-cm pieces and placed in C57BL/6 recipients. The skin allograft was placed in a slightly larger graft bed prepared over the chest of the recipient and secured using Vaseline, gauze and a bandage. The grafts were visually scored daily for evidence of rejection. Skin allograft rejection was monitored by digital microscope photography and was considered fully rejected when it was >90% necrotic. Cruft survival was compared among groups using Kaplan-Meier survival analysis.

REFERENCES

1. Demirkiran, A., et al. Conversion from calcineurin inhibitor to mycophenolate mofetil-based immunosuppression changes the frequency and phenotype of CD4+FOXP3+ regulatory T cells. *Transplantation* 87, 1062-1068 (2009).
2. Gardiner, K. M., Tett, S. E. & Staatz, C. E. Multinational Evaluation of Mycophenolic Acid, Tacrolimus, Cyclosporin, Sirolimus, and Everolimus Utilization, *Annals of transplantation* 21, 1-11 (2016).
3. Lien, Y. H. Top 10 things primary care physicians should know about maintenance immunosuppression for transplant recipients. *The American journal of medicine* (2015).
4. Naesens, M., Kuypers. D. R. & Sarwal, M. Calcineurin inhibitor nephrotoxicity. *Clin J Am Soc Nephrol* 4.481-508 (2009).
5. Wells. A. D., et al. Requirement for T-cell apoptosis in the induction of peripheral transplantation tolerance. *Nature medicine* 5, 1303-1307 (1999).
6. Wu. Z., et al. Homeostatic proliferation is a barrier to transplantation tolerance. *Nature medicine* 10, 87-92 (2004).
7. Auchincloss, H. No tolerance for depletion. *Nature medicine* 10, 21-23 (2004).
8. LaRosa. D. F., Rahman. A. H. & Turka, L. A. The innate immune system in allograft rejection and tolerance. *J Immunol* 178, 7503-7509 (2007).
9. Conde, P., et al. DC-SIGN(+) Macrophages Control the Induction of Transplantation Tolerance. *Immunity* 42, 1143-1158 (2015).
10. Zecher, D., van Rooijen, N., Rothstein. D. M., Shlomchik, W. D. & Lakkis, F. G. An innate response to allogeneic nonself mediated by monocytes. *J Immunol* 183.7810-7816 (2009).
11. Oberbarnscheidt, M. H., et at. Non-self recognition by monocytes initiates allograft rejection. *The Journal of clinical investigation* 124, 3579-3589 (2011).
12. Oberbarnscheidt. M. H. & Lakkis. F. G. Innate allorecognition. Immunol Rev 258, 145-149(2014).
13. Liu. W., Xiao, X., Demirci, G., Madsen. J. & Li. X. C. Innate NK cells and macrophages recognize and reject allogenic nonself in vivo via different mechanisms. *J Immunol* 188, 2703-2711 (2012).
14. Sporri, R. & Reis c Sousa. C. Inflammatory mediators are insufficient for full dendritic cell activation and promote expansion of CD4+ T cell populations lacking helper function. *Nature immunology* 6, 163-170 (2005).
15. Perez-Medina. C., et al. PET Imaging of Tumor-Associated Macrophages with $^{89}$Zr-Labeled High-Density Lipoprotein Nanoparticles. *J. Nucl Med* 56, 1272-1277 (2015).
16. Duivenvoorden. R., et al. A statin-loaded reconstituted high-density lipoprotein nanoparticle inhibits atherosclerotic plaque inflammation. *Nat Commun* 5, 3065 (2014).
17. Tang. J., et al. Inhibiting macrophage proliferation suppresses atherosclerotic plaque inflammation. *Sci Adv* 1(2015).
18. Fantus, D. & Thomson, A. W. The Ups and Downs of TORKinibs in Transplantation. Transplantation 99, c117-118 (2015).
19. Pritchard, D. I. Sourcing a chemical succession for cyclosporin from parasites and human pathogens. *Drug Discov Today* 10, 688-691 (2005).
20. Shuchman, M. Trading restenosis for thrombosis?New questions about drug-eluting stents. *N Engl J Med* 355, 1949-1952 (2006).
21. Chambenoit. O., et al. Specific docking of apolipoprotein A-I at the cell surface requires a functional ABCA1 transporter. *The Journal of biological chemistry* 276, 9955-9960 (2001).
22. Yang, X. P., et al. Scavenger receptor-B1 is a receptor for lipoprotein(a). *Journal of lipid researh* 54, 2450-2457 (2013).
23. Geissmann, F., Jung. S. & Littman, D. R. Blood monocytes consist of two principal subsets with distinct migratory properties. *Immunity* 19, 71-82 (2003).
24. Maury, C. P. & Teppo, A. M. Raised serum levels of cachectin/tumor necrosis factor alpha in renal allograft rejection. *The Journal of experimental medicine* 166, 1132-1137 (1987).
25. Shimizu, K., Schonbeck, U., Mach. F., Libby. P. & Mitchell, R. N. Host CD40 ligand deficiency induces long-term allograft survival and donor-specific tolerance in mouse cardiac transplantation but does not prevent graft arteriosclerosis. *J Immunol* 165, 3506-3518 (2000).
26. Haug. C. E., et al. A phase I trial of immunosuppression with anti-ICAM-1 (CD54) mAb in renal allograft recipients. *Transplantation* 55, 766-772; discussion 772-763 (1993).
27. Ochando. J. C., et at. Alloantigen-presenting plasmacytoid dendritic cells mediate tolerance to vascularized grafts. *Nature immunology* 7, 652-662 (2006).
28. Endo. S., Sakamoto, Y., Kobayashi. E., Nakamura, A. & Takai, T. Regulation of cytotoxic T lymphocyte triggering by PIR-B on dendritic cells. *Proceedings of the National Academy of Sciences of the United States of America* 105, 14515-14520 (2008).
29. Liu, J., et at. Rat CD8+FOXP3+ T suppressor cells mediate tolerance to allogeneic heart transplants, inducing PIR-B in APC and rendering the graft invulnerable to rejection. *Transplant immunology* 13, 239-247 (2004).
30. Thomson, A. W., Turnquist. H. R. & Raimondi, G. Immunoregulatory functions of mTOR inhibition. *Nature reviews* 9, 324-337 (2009).
31. Demir, T., et al. Cancer Screening of Renal Transplant Patients Undergoing Long-Term Immunosuppressive Therapy. *Transplantation proceedings* 47, 1413-1417 (2015).
32. Kupeli. E., et al. Long-term risk of pulmonary embolism in solid-organ transplant recipients. *Exp Clin Transplant* 13 Suppl 1, 223-227 (2015).
33. Hancock. W. W., et at Costimulatory function and expression of CD40 ligand. CD80, and CD86 in vascularized murine cardiac allograft rejection. *Proceedings of* the *National Academy of Sciences of the United States of America* 93, 13967-13972 (1996).
34. Kirk, A. D., et at. Treatment with humanized monoclonal antibody against CD154 prevents acute renal allograft rejection in nonhuman primates. *Nature medicine* 5, 686-693 (1999).
35. Kawai. T., Andrews. D., Colvin. R. B., Sachs, D. H. & Cosimi. A. B. Thromboembolic complications after treatment with monoclonal antibody against CD40 ligand. *Nature medicine* 6, 114 (2000).
36. Nakamura, T., Nakao, T., Yoshimura. N. & Ashihara. E. Rapamycin Prolongs Cardiac Allograft Survival in a Mouse Model by Inducing Myeloid-Derived Suppressor Cells. *Am J Transplant* 15, 2364-2377 (2015).
37. Maldonado, R. A., et al. Polymeric synthetic nanoparticles for the induction of antigen-specific immunological tolerance. *Proceedings of the National Academy of Sciences of the United States of America* 112, E156-165 (2015).
38. Swirski, F. K., et al. Myeloperoxidase-rich Ly-6C+ mycloid cells infiltrate allografts and contribute to an imaging signature of organ rejection in mice. *The Journal of clinical investigation* 120, 2627-2634 (2010).
39. Garcia. M. R., et al. Monocytic suppressive cells mediate cardiovascular transplantation tolerance in mice. *The Journal of clinical investigation* 120, 2486-2496 (2010).
40. Nahrendorf, M., et al. The healing myocardium sequentially mobilizes two monocyte subsets with divergent and complementary functions. *The Journal of experimental medicine* 204, 3037-3047 (2007).
41. Shi, C. & Pamer, E. G. Monocyte recruitment during infection and inflammation. *Nature reviews* 11, 762-774 (2011).
42. Garrod. K. R. & Cahalan. M. D. Murine skin transplantation. *J Vis Exp*, doi:10.3791/634 (2008).
43. Hackstein, H., et al. Rapamycin inhibits IL-4-induced dendritic cell maturation in vitro and dendritic cell mobilization and function in vivo. *Blood* 101, 4457-4463 (2003).
44. Herrera, O. B., et al. A novel pathway of alloantigen presentation by dendritic cells. *J Immunol* 173, 4828-4837 (2004).
45. Corry, R. J., Winn, H. J. & Russell, P. S. Primarily vascularized allografts of hearts in mice. The role of H-2D., H-2K, and non-H-2 antigens in rejection. *Transplantation* 16, 343-350 (1973).
46. Miyake. Y., et al. Critical role of macrophages in the marginal zone in the suppression of immune responses to apoptotic cell-associated antigens. *The Journal of clinical investigation* 117, 2268-2278 (2007).
47. Zarzycka, T. et al. Discovery of small molecule CD40-TRAF6 inhibitors. *J. Chem. Inf. Model.* 55:294-307 (2015).
48. Chatzigeorgiou et al. 2014: Blocking CD40-TRAF6 signaling is a therapeutic target in obesity associated insulin resistance. *Proc Natl Acad Sci USA*. 2014 Feb. 18:111(7):2686-91.
49. Van der Berg et al. 2015; Blocking CD40-TRAF6 interactions by small-molecule inhibitor 6860766 ameliorates the complications of diet-induced obesity in mice. Int J Obes (Lond). 2015 May; 39(5):782-90.

Example 2

Targeted CD40-TRAF6 Inhibition Resolves Macrophage Accumulation in Atherosclerosis.

In atherosclerosis, macrophage accumulation is directly linked to destabilization and rupture of plaque, causing acute atherothrombotic events. Circulating monocytes enter the plaque and differentiate into macrophages, where they are activated by CD4+ T lymphocytes through CD40-CD40 ligand signaling. Here we show that interruption of this signaling pathway in monocytes/macrophages exerts rapid anti-inflammatory effects in an $ApoE^{-/-}$ mouse model of atherosclerosis. For this purpose we developed an infusible reconstituted high-density lipoprotein nanoparticle carrying a small molecule inhibitor of the interaction of CMD40 and tumor necrosis factor receptor-associated factor 6. We show monocyte/macrophage specific targeting of our nanoimmunotherapy, which impairs their migratory capacity. Rapid reduction of plaque inflammation by this therapy represents a novel strategy in the treatment of atherosclerosis, with high potential for clinical translation, as illustrated by the favorable toxicity profile in non-human primates.

The recruitment of circulating monocytes that differentiate into macrophages is a key contributing process in aggravating atherosclerotic plaque inflammation [1]. This dynamic macrophage accumulation in plaque is directly linked to the development of atherothrombotic events [1].

As early as in the 1990s it was recognized that the activation of plaque macrophages by CD4+ T-lymphocytes via CD4)-CD40 ligand (CD40-CD40L) signaling plays a central role in abetting plaque inflammation [2]. Genetic disruption of CD40L in apolipoprotein e knockout ($Apoe^{-/-}$) mice drastically decreases atherosclerotic lesion development and diminishes plaque T-lymphocyte and macrophage content [3]. Treatment of low density lipoprotein receptor knockout ($LDL^{-/-}$) mice and $Apoe^{-/-}$ with an anti-mouse CD40L antibody had similar atheroprotective effects [4-6]. Further studies revealed that tumor necrosis factor receptor-associated factor 6 (TRAF6) is of specific importance in propelling CD40's signaling cascade inside macrophages [7]. TRAFs are adaptor proteins that can bind the cytoplasmic domain of CD40 and couple the receptor complex to several different signal transduction pathways [8]. In fact, deficiency of CD44-TRAF6 interactions in myeloid cells has been shown to decrease monocyte recruitment to plaques and abolish atherosclerotic plaque formation in $Apoc^{-/-}$ mice [7].

Although the CD40-TRAF6 interaction provides a promising therapeutic target, major limitations are associated with its inhibition. In addition to CD40-TRAF6 interaction's role in mycloid cells, it partly controls the maturation of B-lymphocytes and generation of long-lived plasma cells [9]. Therefore, long-term inhibition of the CD40-TRAF6 interaction will likely cause immune deficiencies, rendering it an unfeasible therapeutic approach for atherosclerosis.

To address this issue we developed a targeted immunotherapy with the ability to block the CD40-TRAF6 interaction specifically in monocytes/macrophages. For this purpose, we incorporated a recently developed small molecule inhibitor of the CD40-TRAF6 interaction in reconstituted high density lipoprotein (TRAF6i-HDL) [10, 11]. We show in an $Apoe^{-/-}$ mouse model of atherosclerosis that TRAF6i-HDL targets monocytes/macrophages, while lymphocytes do not take up nanoparticles. After a single week of TRAF6i-HDL immunotherapy a rapid decrease in plaque inflammation and decreased monocyte recruitment was observed. In line with these findings, whole transcriptome analysis indicated that cell migration was among the affected cellular processes. Finally, to assess its translational potential, we evaluated TRAF6i-HDL's pharmacokinetics, biodistribution and safety in non-human primates (NHPs).

Results

Traf6i-HDL Characteristics.

Figure 14A:
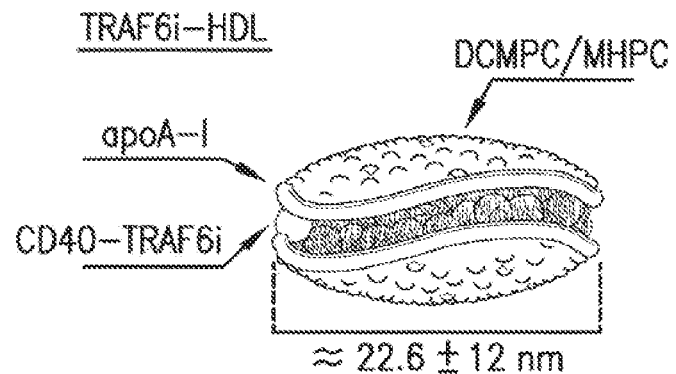
FIGS. 14A-G are images, schematics and graphs showing TRAF6i-HDL nanoparticle biodistribution and uptake. Eight week old Apoc−/− mice were fed a high-cholesterol diet for 12 weeks and then received an IV injection with either 89Zr—, DiR- or DiO-labeled TRAF6i-HDL nanoparticles. Twenty-four hours later, mice were used for PET/CT imaging or sacrificed for ex vivo NIRF imaging or flow cytometry analysis.

The aim of the study was to decrease plaque inflammation by specifically inhibiting the CD40-TRAF6 interaction in monocytes/macrophages via targeted nanoimmunotherapy (TRAF6i-HDL). The TRAF6i-HDL nanoparticle was constructed from human apolipoprotein A-I (apoA-1), and the phospholipids 1-myristoyl-2-hydroxy-sn-glycero-phosphocholine (MHPC) and 1,2-dimyristoyl-sn-glycero-3-phosphatidylcholine (DMPC), in which a lipophilic small molecule inhibitor of CD40-TRAF6 interaction (SMI 68770021 was encapsulated [8, 11]. Because apoA-1 can have modulatory effects by itself, the nanoimmunotherapy was designed with a low apoA-I to drug ratio. The resulting TRAF6i-HDL nanoparticle, schematically shown in FIG. 14A, measured 22.6+/−12 nm in diameter (PDI=0.3), as determined by dynamic light-scattering and transmission electron microscopy (TEM). TRAF6i-HDL variants, incorporating fluorescent dyes (DiO or DiR) or Zirconium-89 ($^{89}$Zr) radiolabeled phospholipids, were synthesized to allow detection by fluorescence techniques, positron emission tomography (PET), gamma counting and autoradiography.

Schematic Overview

Figure 14B:
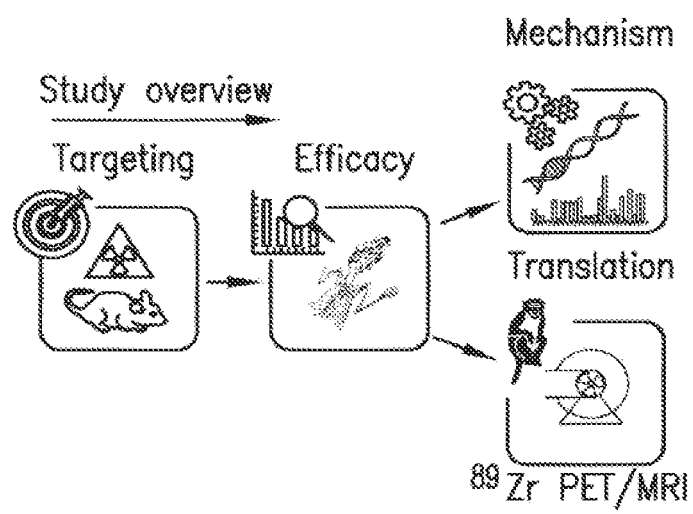

A schematic overview of the study design is shown in FIG. 14B. The first pan of the study was performed in mice with atherosclerosis (Apoe$^{-/-}$ mice on a high cholesterol diet). In these mice, we first studied TRAF6i-HDL's toxicity, pharmacokinetics, biodistribution, and atherosclerotic plaque monocyte/macrophage targeting efficiency. Subsequently, we assessed plaque regression efficacy of a one-week TRAF6i-HDL regimen involving four intravenous infusions. Next, we investigated the mechanism by which TRAF6i-DL affects plaque monocytes/macrophages using whole transcriptome analysis. The second part of the study focused on the translatability of TRAF6i-HDL nanoimmunotherapy. For this purpose we investigated TRAF6i-HDL's toxicity and pharmacokinetics, while in vivo positron emission tomography with magnetic resonance (PET/MRI) was performed to longitudinally study biodistribution and vessel wall targeting in non-human primates.

Toxicity, Pharmacokinetics, and Biodistribution Studies in Apoe$^{-/-}$ Mice.

One week TRAF6i-HDL treatment had no effect on erythrocytes, platelets or leucocyte levels (FIG. 20). The number of reticulocytes and lymphocytes was somewhat increased when compared to placebo. The numbers of T cells and B cells in bone marrow blood and spleen were not affected by TRAF6i-HDL therapy. No toxic effects were observed on kidney and hepatic function, although alkaline phosphatase was somewhat increased (FIG. 21). Lipids, glucose, protein and electrolytes were unaffected.

Figure 14C:
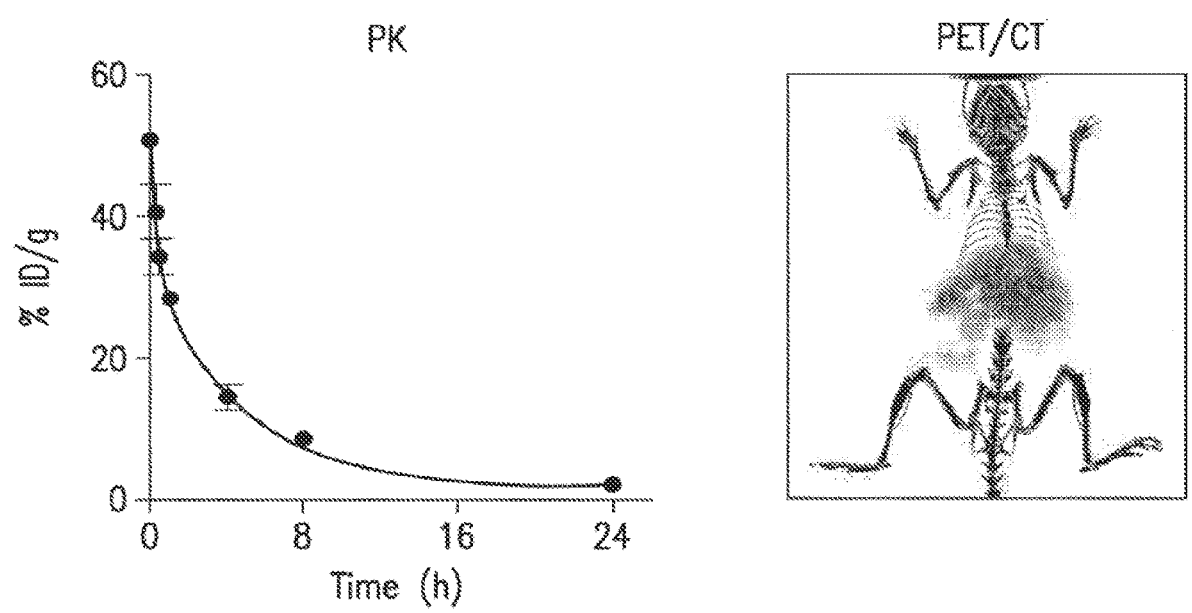
Figure 14D:
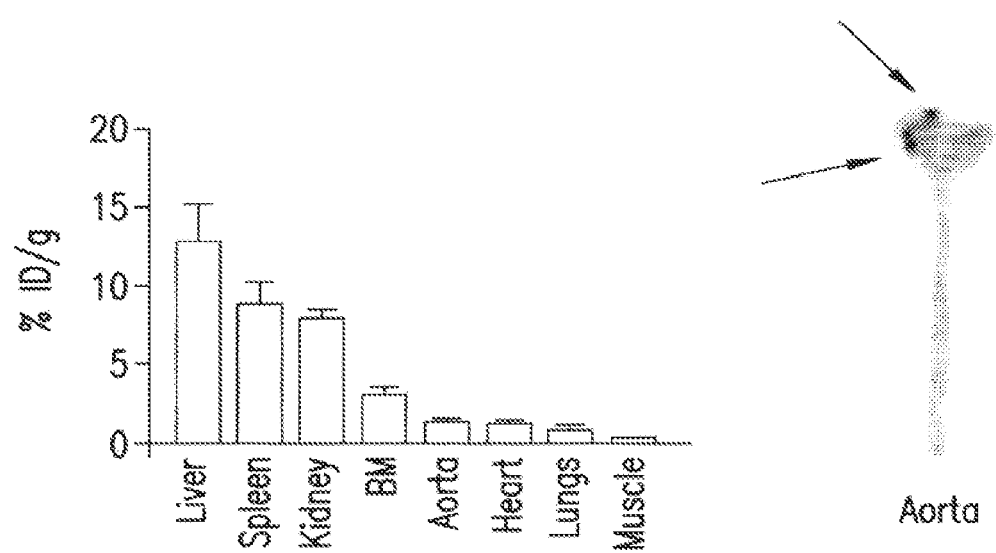

To investigate its pharmacokinetics and biodistribution, Apoe$^{-/-}$ mice received a single infusion of $^{89}$Zr-radiolabeled TRAF6i-HDL. Blood radioactivity clearance of $^{89}$Zr—TRAF6i-HDL was measured over 24 hours and data were fitted using a two-phase decay non-linear regression. The weighted blood half-life (t½) was finally calculated to be 124.4 min based on a t½-fast of 13.7 min and a t½-slow of 195 min (FIG. 14C). Biodistribution was evaluated by in vivo PET/CT imaging (FIG. 14C) and validated by ex vivo gamma counting, the latter expressed as a percentage of injected dose per grain tissue (% ID/g; FIG. 14D). As expected. PET/CT imaging showed that TRAF6i-HDL primarily accumulated in the liver, spleen and kidney, organs known to take up and metabolize HDL. Gamma counting data confirmed these results, showing nanoparticle uptake of 12.8% ID/g in the liver, 8.9% ID/g in the spleen, and 7.9% ID/g in the kidneys. In comparison, the heart, a similar sized organ, only contained 1.1% ID/g (FIG. 14D). Ex vivo near infrared fluorescence (NIRF) imaging, 24 hours after infusion, corroborated the PET/CT and gamma counting observations, showing that TRAF6i-HDL accumulates mostly in the liver, spleen and kidneys.

Flow cytometry analysis revealed that Ly6Chi monocytes and macrophages in blood, bone marrow, and spleen took up DiO labeled TRAF6i-HDL. Neutrophils, Ly6Clo monocytes and dendritic cells also took up DiO-TRAF6i-HDL, while lineage positive CD1 b negative cells (all non-myeloid cells) did not (FIG. 14G), indicative of myeloid cell specificity.

TRAF6I-HDL Accumulation in Atherosclerotic Lesions.

Figure 14E:
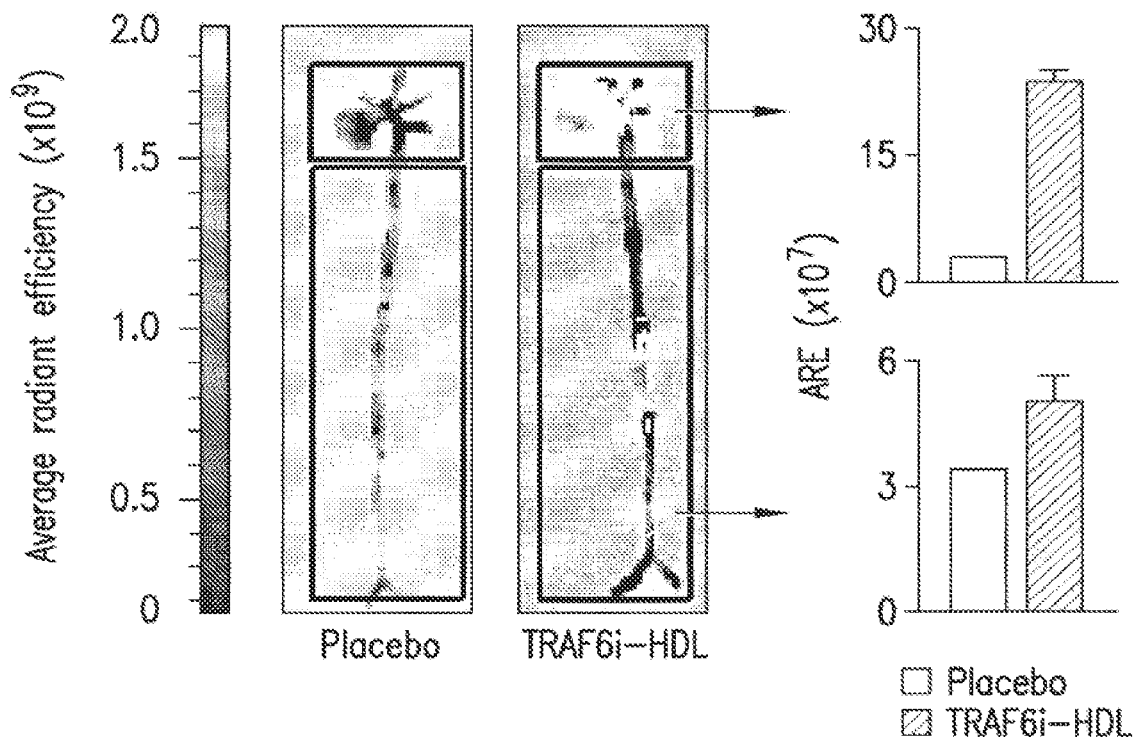
Figure 14F:
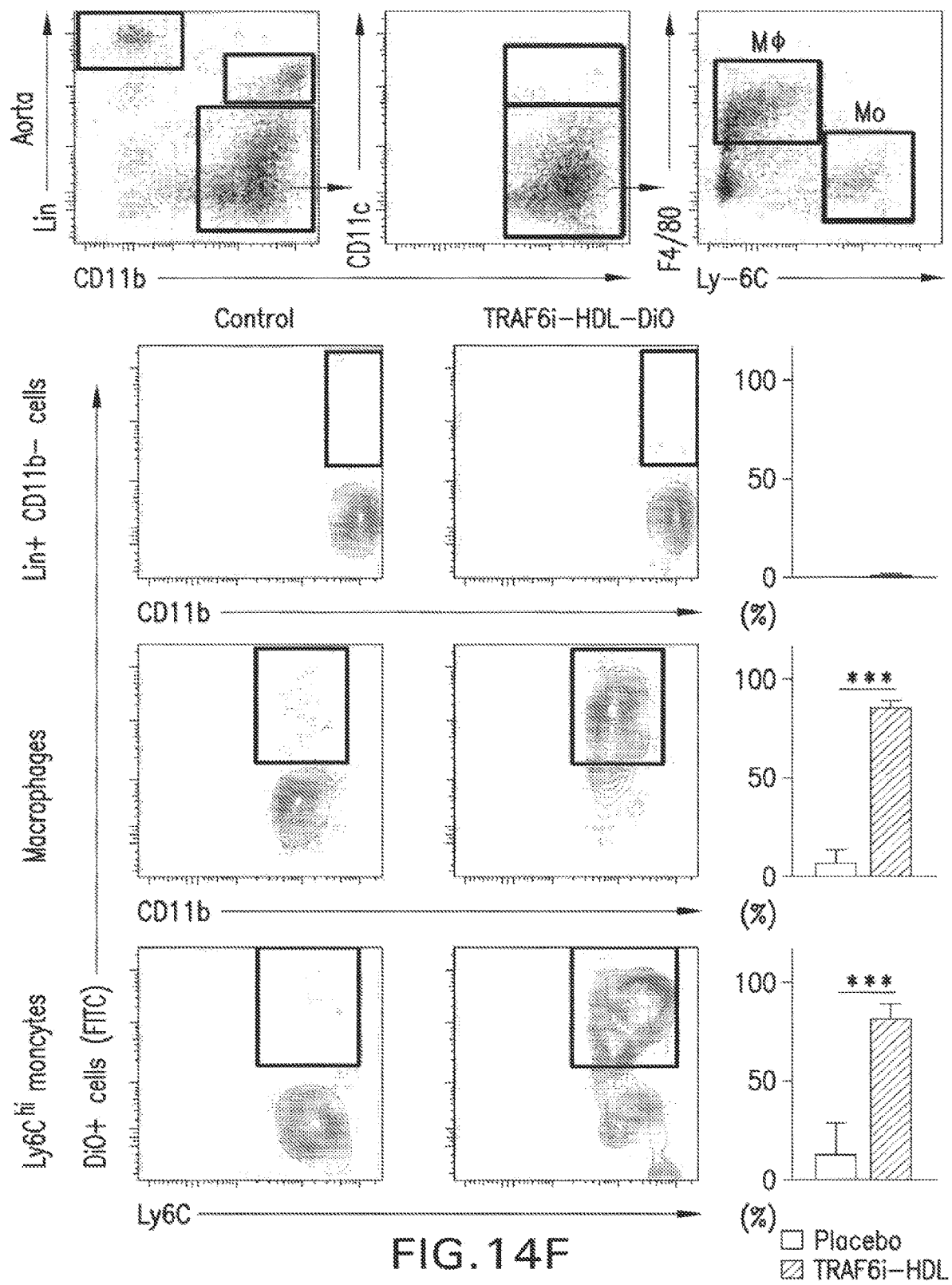
Figure 14G:
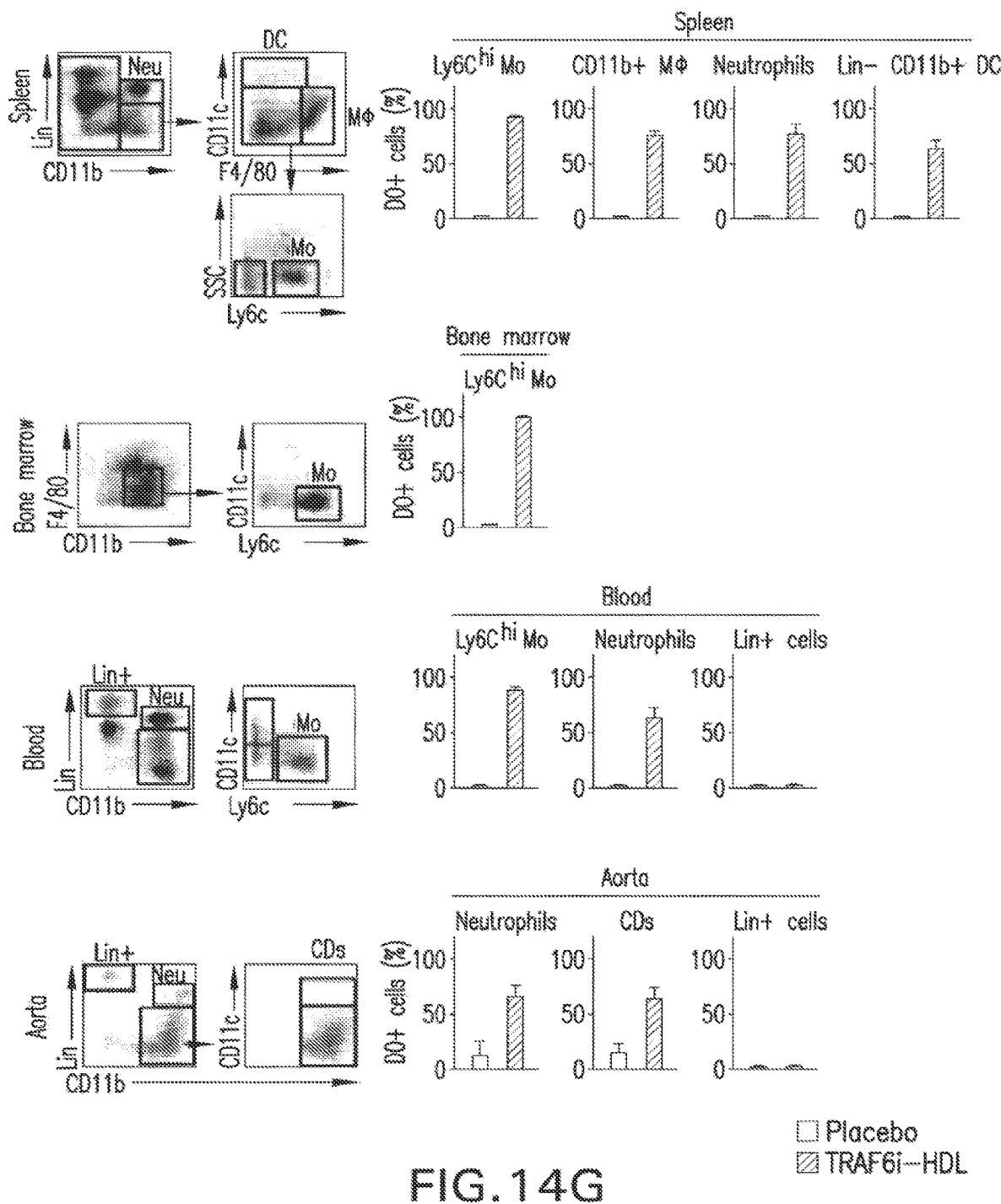

Fr vivo gamma counting of whole the aortas showed that 1.3% ID/g of 89Zr-TRAF6i-HDL had accumulated 24 hours after infusion (FIG. 14D). Looking specifically at TRAF6i-HDL nanoparticle distribution throughout the aorta, the uptake was highest in the aortic sinus area, which is the preferential site of plaque development in this mouse model. While only accounting or 6.4% of the total area, the aortic sinus area generated approximately 29% of the signal, corresponding to 5.9% ID/g (FIG. 1d). NIRF imaging showed similar preferential accumulation of DiR-labeled TRAF6i-HDL in the aortic sinus area (FIG. 14E). Cell specificity of DiO labeled TRAF6i-HDL uptake in aortic plaque was assessed by flow cytometry. We found that 86% of macrophages and 81% of Ly6Chi monocytes had taken up DiO-TRAF6i-HDL, while lineage positive cells (all non-myeloid cells) had taken up virtually none (FIG. 14F). Furthermore, the majority of neutrophils (64%) and dendritic cells (61%) in the aortic plaque were found to contain labeled nanoparticles (FIG. 14G). These results mirror our findings in blood, bone marrow and spleen, showing that cells of the myeloid lineage, and in particular the Ly6Chi monocyte subset and macrophages, are preferentially targeted by TRAF6i-HDL nanoparticles.

In Vivo Effects of TRAF6l-HDL on Plaque Inflammation.

To assess the therapeutic efficacy of TRAF6i-HDL, we used 20 week old Apoe$^{-/-}$ mice that had been on a high cholesterol diet for 12 weeks in order to develop atherosclerotic lesions. While all mice remained on a high-cholesterol diet, they received four intravenous infusions of placebo, control HDL nanoparticles without payload, or TRAF6i-HDL over a period of 7 days. The CD40-TRAF6 inhibitor dose administered per infusion was 5 mg/kg. To limit a dominant therapeutic effect of apoA-1 itself, we used a low apoA-l dose of 9 mg/kg. All mice were sacrificed 24 hours after the final infusion.

Figure 15A:
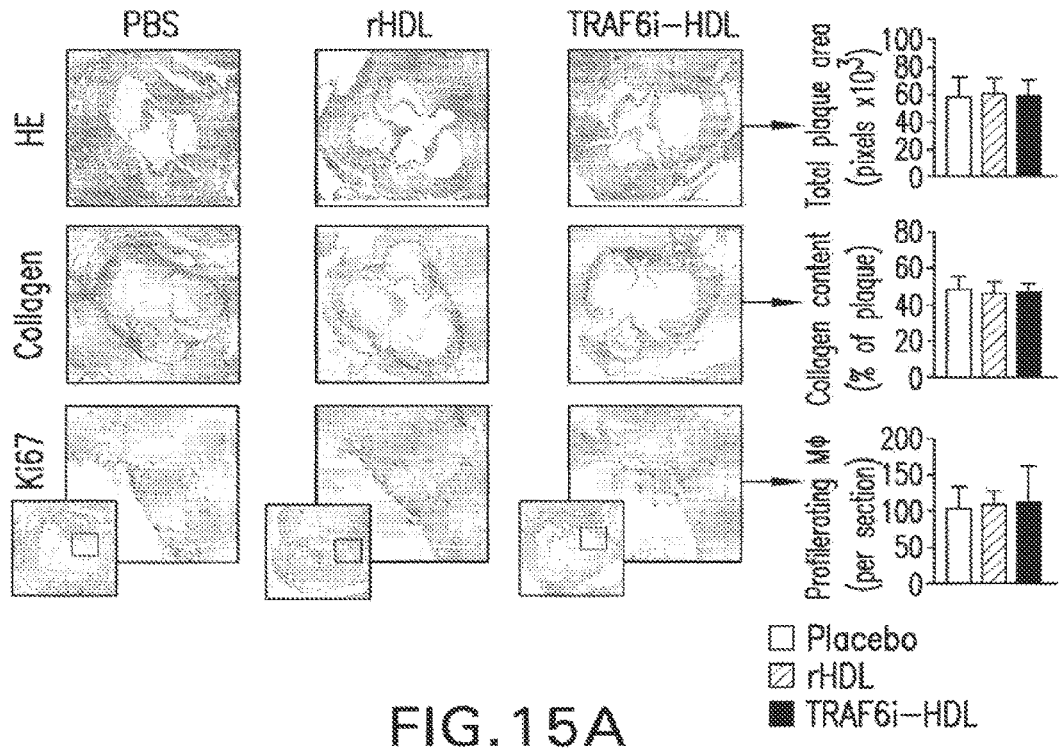
FIGS. 15A-B ae images and graphs illustrating that TRAF6i-HDL therapy decreased plaque macrophage content as assessed by histology. Eight week old Apoe−/− mice were fed a high-cholesterol diet for 12 weeks and subsequently received treatment with four i.v. injections of either PBS (n=10), rHDL (n=10) or TRAF6i-HDL (n=10), over the course of seven days. Twenty-four hours after the last injection, aortic roots were sectioned (4 µM and stained with immunohistochemistry methods.
Figure 15B:
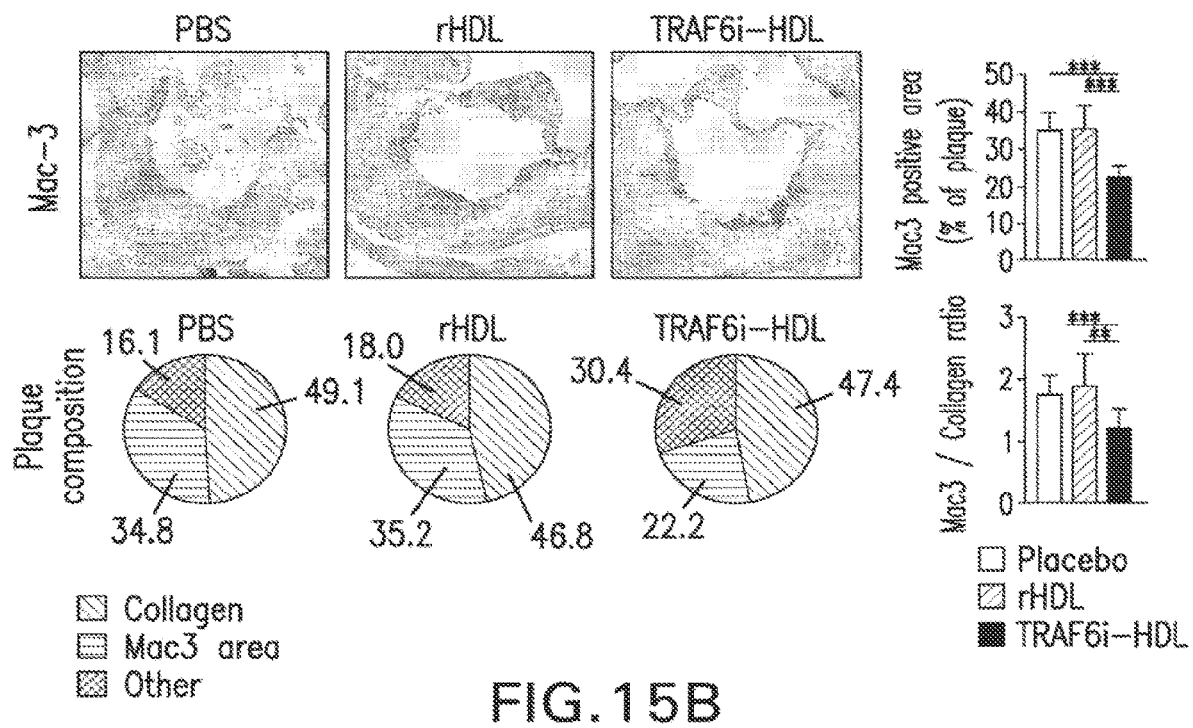

For the first experiment we performed quantitative histologic analysis of plaques in the aortic sinus area in mice treated with placebo, HDL or TRAF6i-HDL (n=10 per group). Cross-sections were stained with Hematoxylin and Eosin (H&E) and Sirius Red (collagen), and immunostained for Mac3 (macrophages) and Ki67 (proliferating cells). No significant difference in plaque size or collagen content was observed across the groups (FIG. 15A). The percentage of Mac3 positive area was however markedly decreased by 36% (p=0.001) and 37% (p<001) as compared to the placebo and HDL groups, respectively (FIG. 15B). As a result, also the Mac3 to collagen ratio in the plaque was favorably affected towards a more stable plaque phenotype in the TRAF6i-HDL group, as the ratio was decreased by 31% (p<0.001) and 36% (p=0.004) compared to the placebo and HDL groups (FIG. 15B). The number of proliferating macrophages was similar in all groups (FIG. 15A), indicating that the observed decrease in plaque macrophages was not caused by a decrease in local proliferation of macrophages. Previous studies showed that in addition to monocyte recruitment, local macrophage proliferation plays a pivotal role in fueling plaque inflammation [12].

Figure 16A:
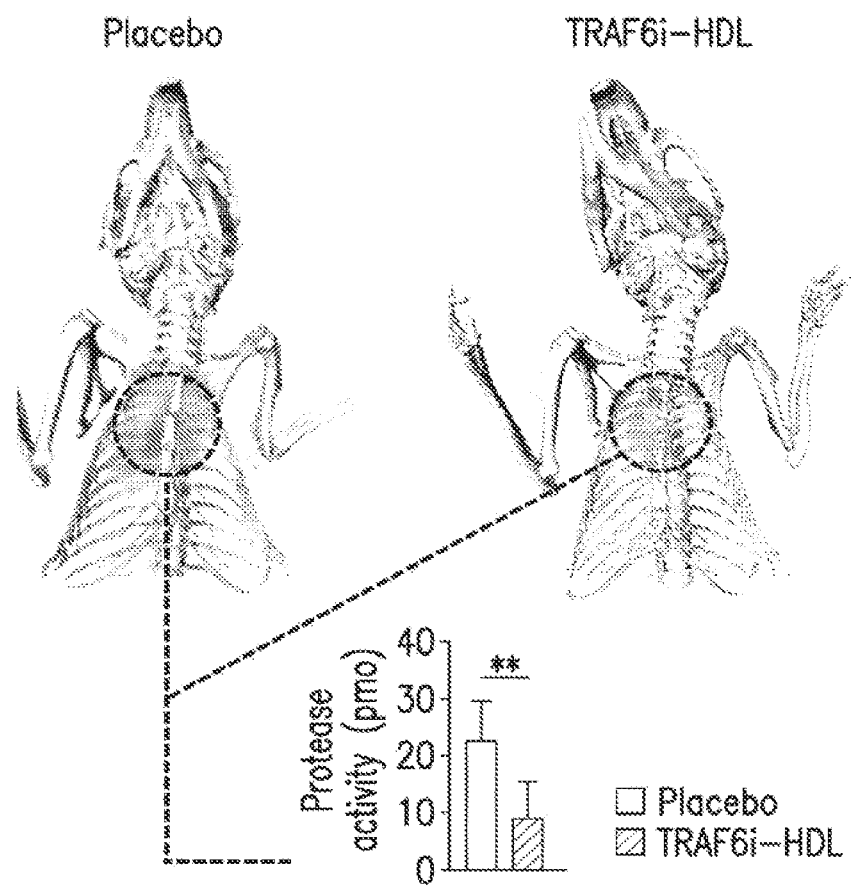
FIGS. 16A-E are images and graphs showing that TRAF6i-HDL decreases plaque inflammation due to impaired Ly6$^{hi}$ monocyte recruitment. Eight week old Apoc−/− mice on a high-cholesterol diet for 12 weeks and were treated with four i.v. injections of either placebo (PBS), rHDL, or TRAF6i-HDL within a single week.
Figure 16B:
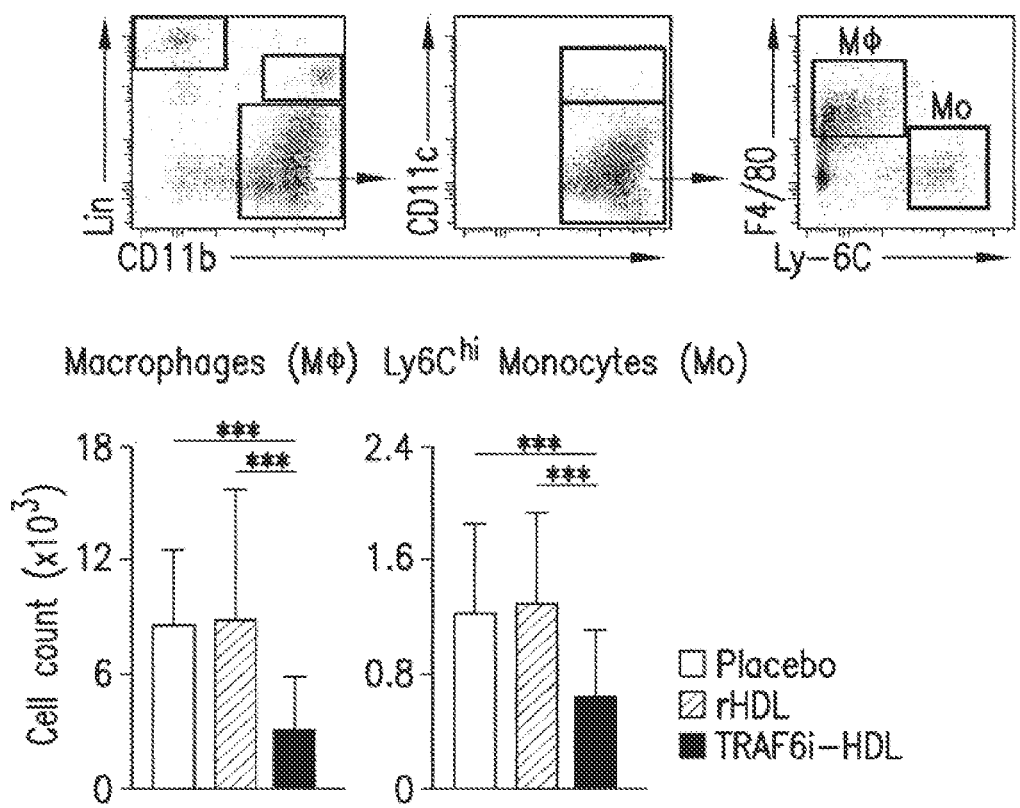

Subsequently, we performed fluorescence molecular tomography fused with computed tomography (FMT/CT) imaging to visualize protease activity in the aortic sinus area. Placebo (n=8) and TRAF6i-HDL (n=7) treated Apoe mice all received one injection of an activatable pan-cathepsin protease sensor 24 hours before imaging. The protease sensor is taken up by activated macrophages, followed by cleavage of the protease sensor within the endolysosomal, yielding fluorescence as a function of enzyme activity. TRAF6i-HDL therapy decreased protease activity by 60% (p=0.002, FIG. 16A). Next, we focused on quantification of aorta macrophage content by flow cytometry of whole aortas. Again, 20 week old Apoc$^{-/-}$ on a high cholesterol diet were treated with either placebo (n=27), HDL (n=27) or TRAF6i-HDL (n=27). Aorta macrophage content decreased markedly in the TRAF6i-HDL treated group, by 66% and 67% (p<0.001 for both comparisons), as compared to the placebo and HDL groups (FIG. 16B). These results corroborate the observations made by histologic analysis and FMT-CT. Furthermore, in the TRAF6i-HDL treated group aorta T lymphocyte content was decreased by 65% and 49% when compared to placebo and HDL respectively. Altogether these data indicate a potent anti-inflammatory effect of TRAF6i-HDL in atherosclerotic plaques after only a single week of therapy.

Figure 16C:
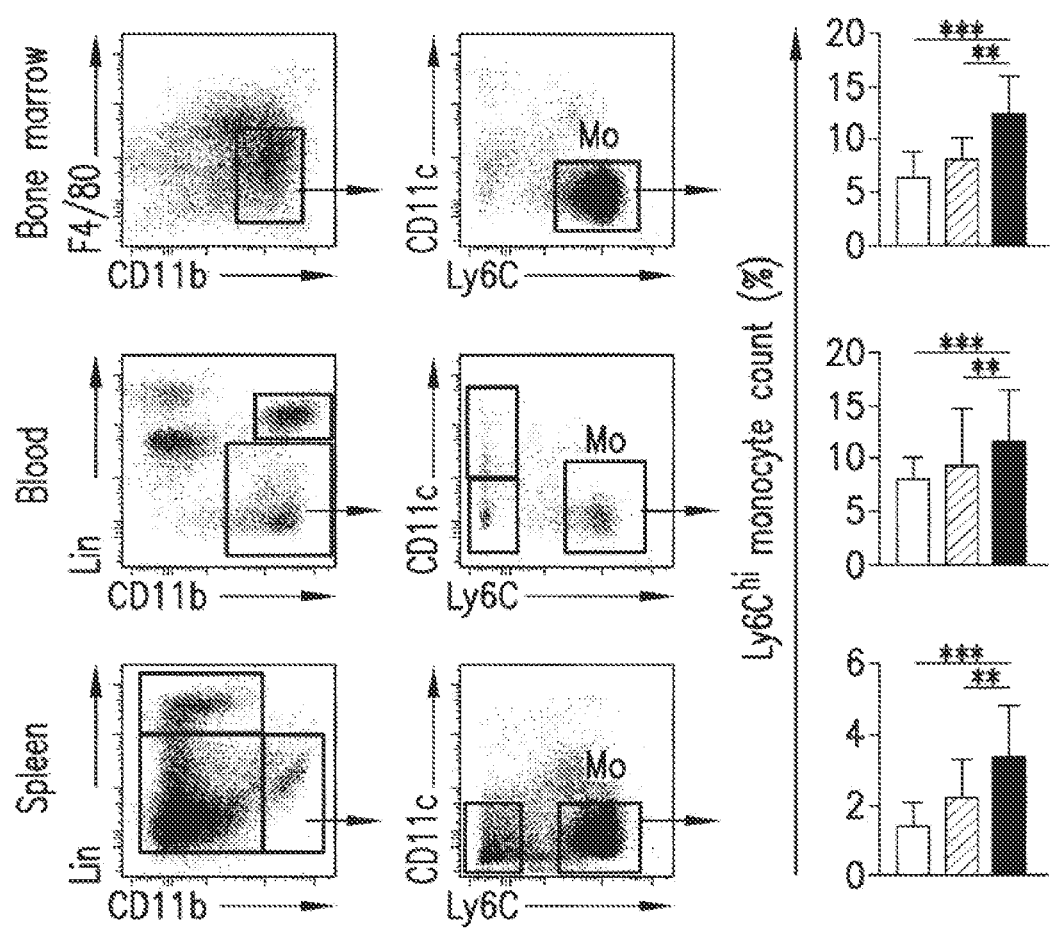

Since we had already observed that the number of proliferating Ki67+ macrophages was not affected by therapy, we hypothesized that the decrease in plaque macrophages content and inflammation might be caused by decreased monocyte recruitment instead [13,14]. To further investigate this, we first quantified aortic Ly6C$^{hi}$ monocytes in the same flow-cytometry experiment as the one in which we measured macrophage content. We observed that the decrease in macrophages was paralleled by a 49% and 52% (p<0.001 for both comparisons) decrease in Ly6C$^{hi}$ monocytes in the aorta, as compared to the placebo and HDL groups respectively (FIG. 16B). Interestingly, the reduction in aortic Ly6C$^{hi}$ monocyte content could not be explained by a systemic decrease in Ly6$^{hi}$ monocytes (FIG. 16C).

Figure 16D:
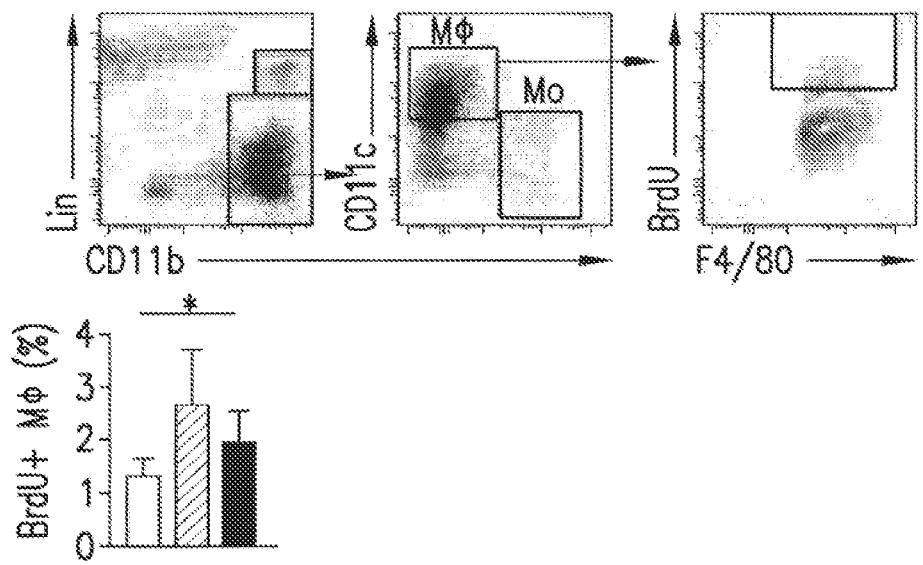
Figure 16E:
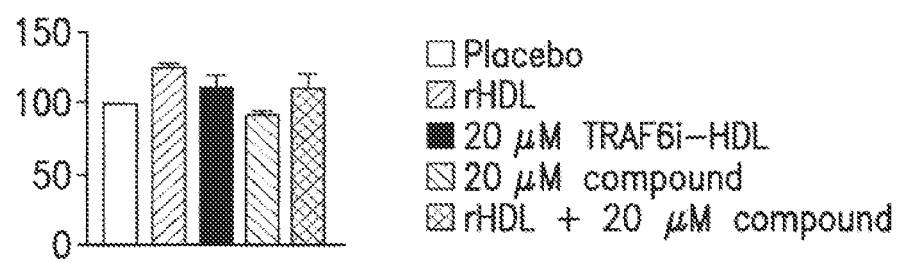

Secondly, we performed an experiment in which the thymidine analogue 5-bromo-2'-deoxyuridine (BrdU) was injected intraperitoneally 2 hours prior to sacrificing the mice. BrdU incorporates into newly synthesized DNA, and therefore can be used as a marker for proliferation. FIG. 16D shows that the percentage of plaque macrophages that had incorporated BrdU was not decreased by TRAF6i-HDL therapy. This result is in line with the histology observation on Ki67 expression. In an in vitro experiment with RAW 264.7 cell line of murine macrophages, characterized by a high proliferation rate [15], incubation with the CD40-TRAF6 inhibiting compound or TRAF6i-HDL did not affect the proliferation rate (FIG. 16E).

Taken together, these data indicate that plaque macrophage content as well as protease activity was decreased by TRAF6i-HDL therapy. The mechanism of action by which TRAF6i-HDL decreases plaque inflammation is likely mediated through the abatement of monocyte recruitment, while local macrophage proliferation is not affected.

Comparative Whole Transcriptome Analysis of Plaque Monocytes/Macrophages.

In order to gain insight into the effects of TRAF6i-HDL on gene expression of plaque monocytes/macrophages, we isolated CD68 positive cells from aortic sinus plaques by laser capture microdissection of mice either treated with placebo or TRAF6i-HDL. Whole RNA of these cells was isolated for sequencing.

Figure 17A:
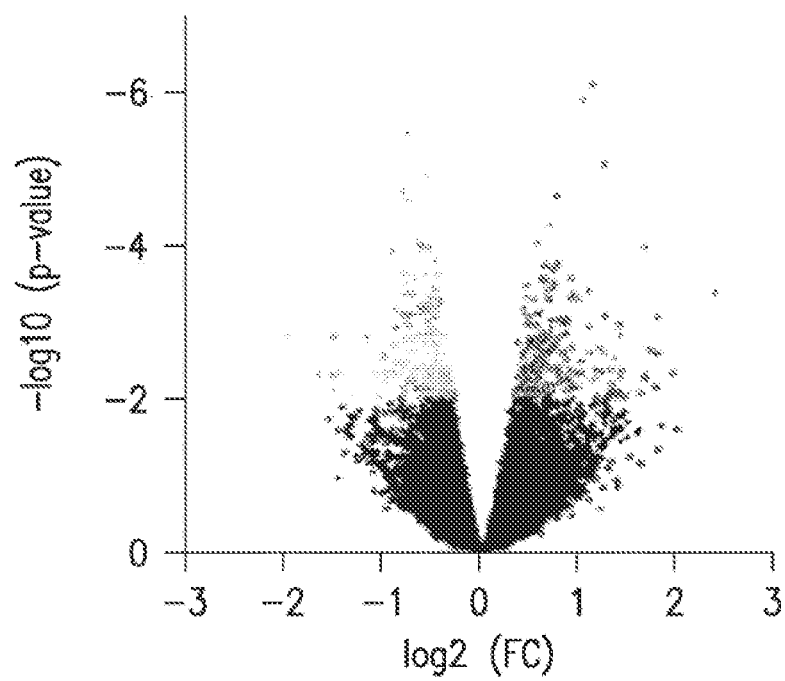
FIGS. 17A-D are graphs and diagrams reflecting data from whole transcriptome analysis of plaque monocytes/macrophages illustrating the effect of TRAF6i treatment on cell migration, among other affected processes. Eight week old ApoE−/− mice were fed a high-cholesterol diet for 12 weeks and were then treated with four i.v. injections of either placebo (n=10) or TRAF6i-HDL (n=10) over seven days. Twenty-four hours after the last injection, mice were sacrificed and frozen sections of aortic roots were used for the isolation of plaque macrophages by laser capture microdissection, followed by RNA isolation and sequencing.
Figure 17B:
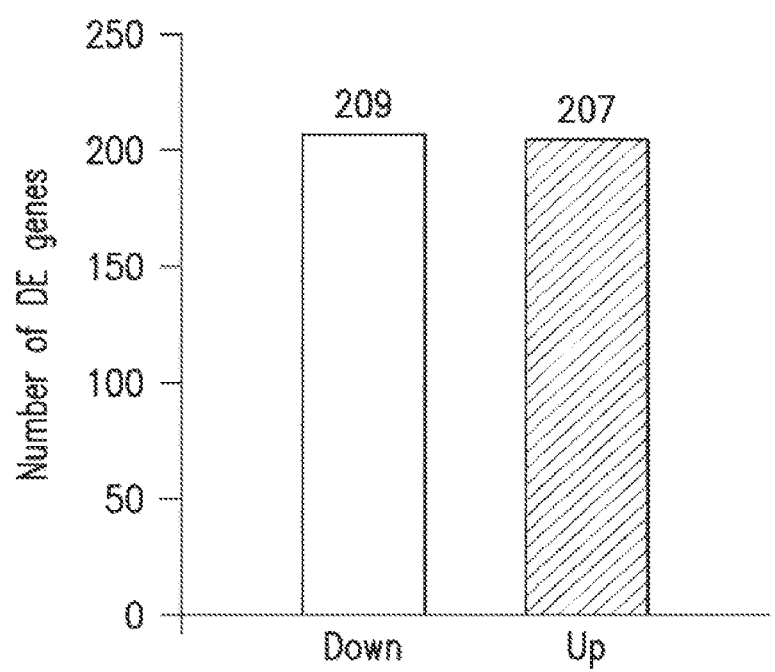
Figure 17C:
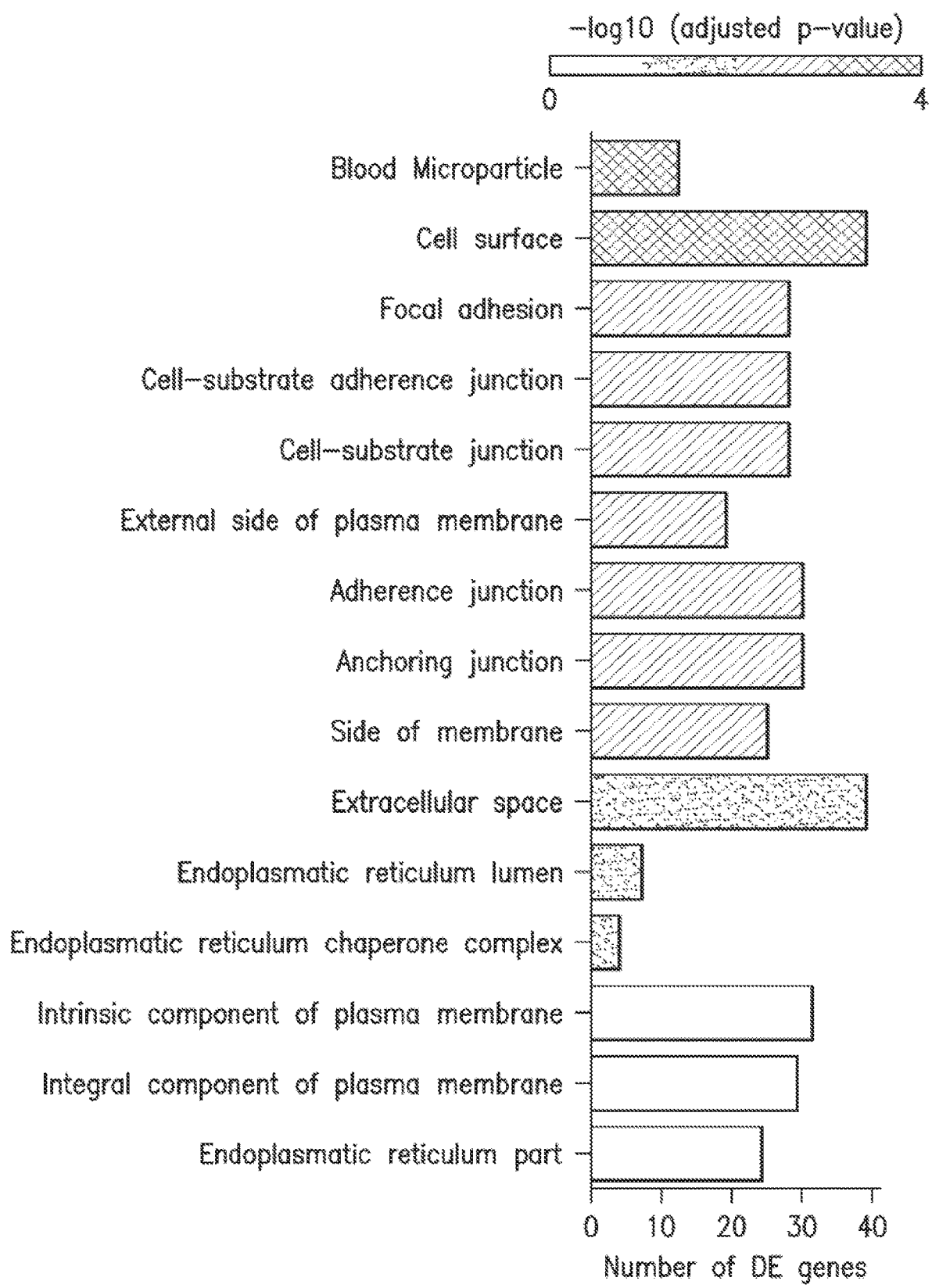

We identified genes that were differentially expressed (DE) between placebo and TRAF6i-HDL treated mice. Correction for multiple testing was performed with a false discovery rate (FDR)<0.2 (FIG. 17A). A total of 416 DE genes were identified, of which 209 genes were down-regulated and 207 up-regulated (FIG. 17B). Gene ontology (GO)-function was used to annotate the DE genes, and to find cellular components that significantly enriched with DE genes (FIG. 17C). In the 15 enriched GO terms that significantly enriched with DE genes. "focal adhesion" is of most interest. Other enriched GO terms, such as "cell-substrate adherent junction", "cell-substrate junction". "adherence junction", and "anchoring junction" are closely related to "focal adhesion" and the genes in these GO terms overlapped to a high degree (FIG. 22). Focal adhesion is a dynamic process in which protein complexes connect to the extracellular matrix, and plays a central role in monocyte/macrophage migration [16]. In a subsequent analysis, the same 416 DE genes were mapped with the Kyoto Encyclopedia of Genes and Genomes (KEGG) pathway tool, by which we identified two significantly altered pathways, namely "focal adhesion" and "endocytosis" (FIG. 17D, FIG. 23).

Figure 17D:
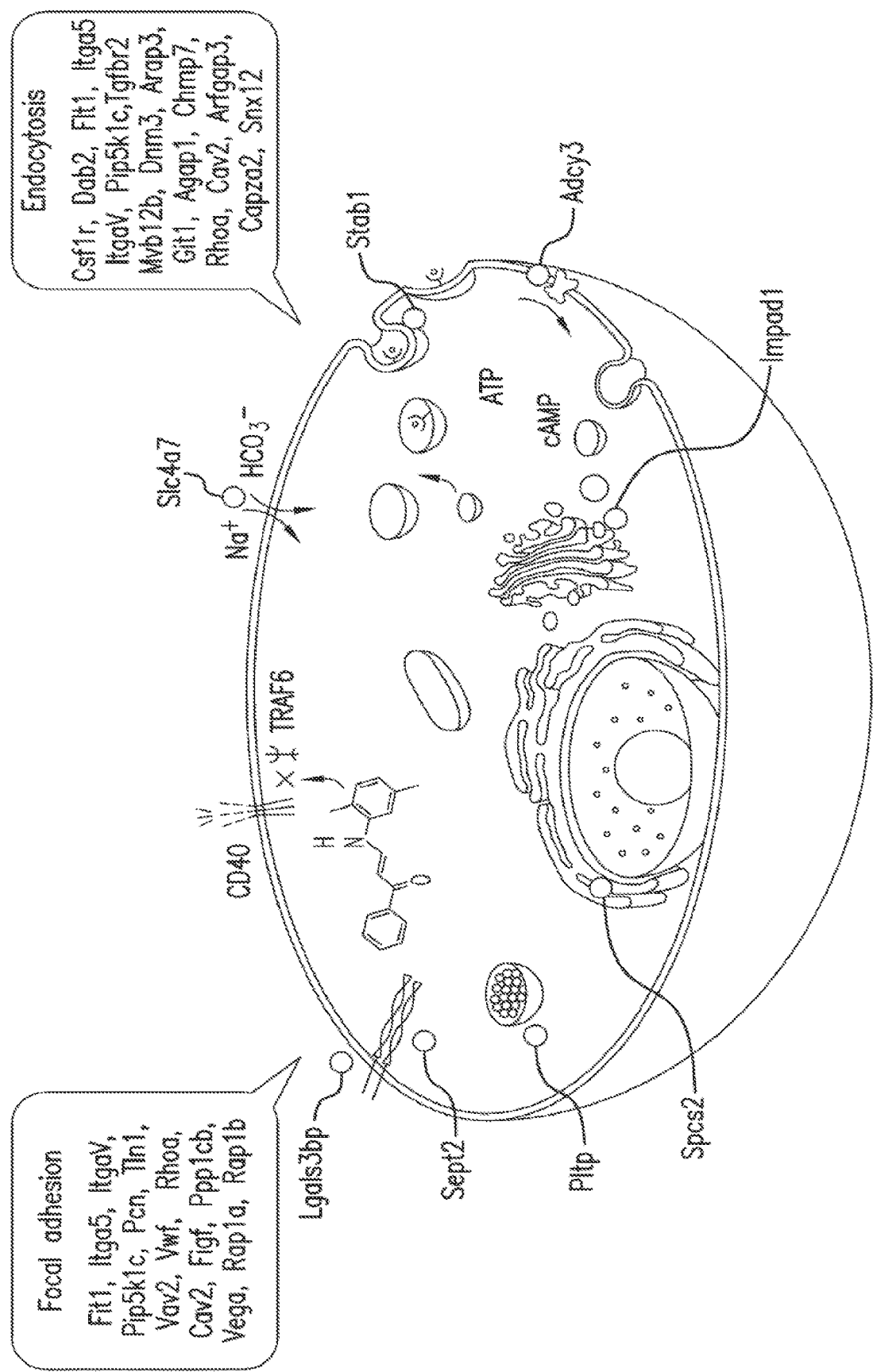

The most significant DE genes, all with FDR<0.05 (FIG. 17D. FIG. 24) were Adcy3, Lgals3 bp, Pltp and Stab1 (up-regulated) and Impad1. Sept2, Slc4a7 and Spcs2 (down-regulated). Among these genes, macrophage derived PLTP is known to exert antiatheroaclerotic effects 1171, and Stab1 (encodes for Stabilin-1) has functions in lymphocyte homing and cell adhesion and is associated with an atheroprotective macrophage phenotype [18, 19], Sept2 (encoding for Sep-tin2) is known to be abundantly expressed in macrophages and is required for phagosome formation [20]. Together, the transcriptome data analyses indicate that among various affected processes, focal adhesion is significantly affected by TRAF6i-HDL therapy. The fact that focal adhesion, a process involved in cell migration, is importantly affected is consistent with our aforementioned observation of decreased Ly6C monocyte recruitment in TRAF6i-HDL treated mice. We did not observe an effect on gene expression related to macrophage proliferation, apoptosis or migratory egress (FIG. 25).

TRAF6I-HDL Toxicity, Pharmacokinetics, and Biodistribution Studies in Non-Human Primates.

In order to assess the translatability of TRAF6i-HDL therapy, we performed, comprehensive blood testing, histological analysis, and advanced pharmacokinetics and biodistribution studies in TRAF6i-HDL treated non-human primates (NHP). Six NHPs were used for complete haematological analyses and post mortem histological analysis and another six for biodistribution imaging (PET/MRI) and blood chemistry analysis. The NHPs were injected with either placebo or a single dose of TRAF6i-HDL 01.25 mg/kg) and either sacrificed after 72 hours or imaged at multiple time points and then sacrificed.

Figure 18A:
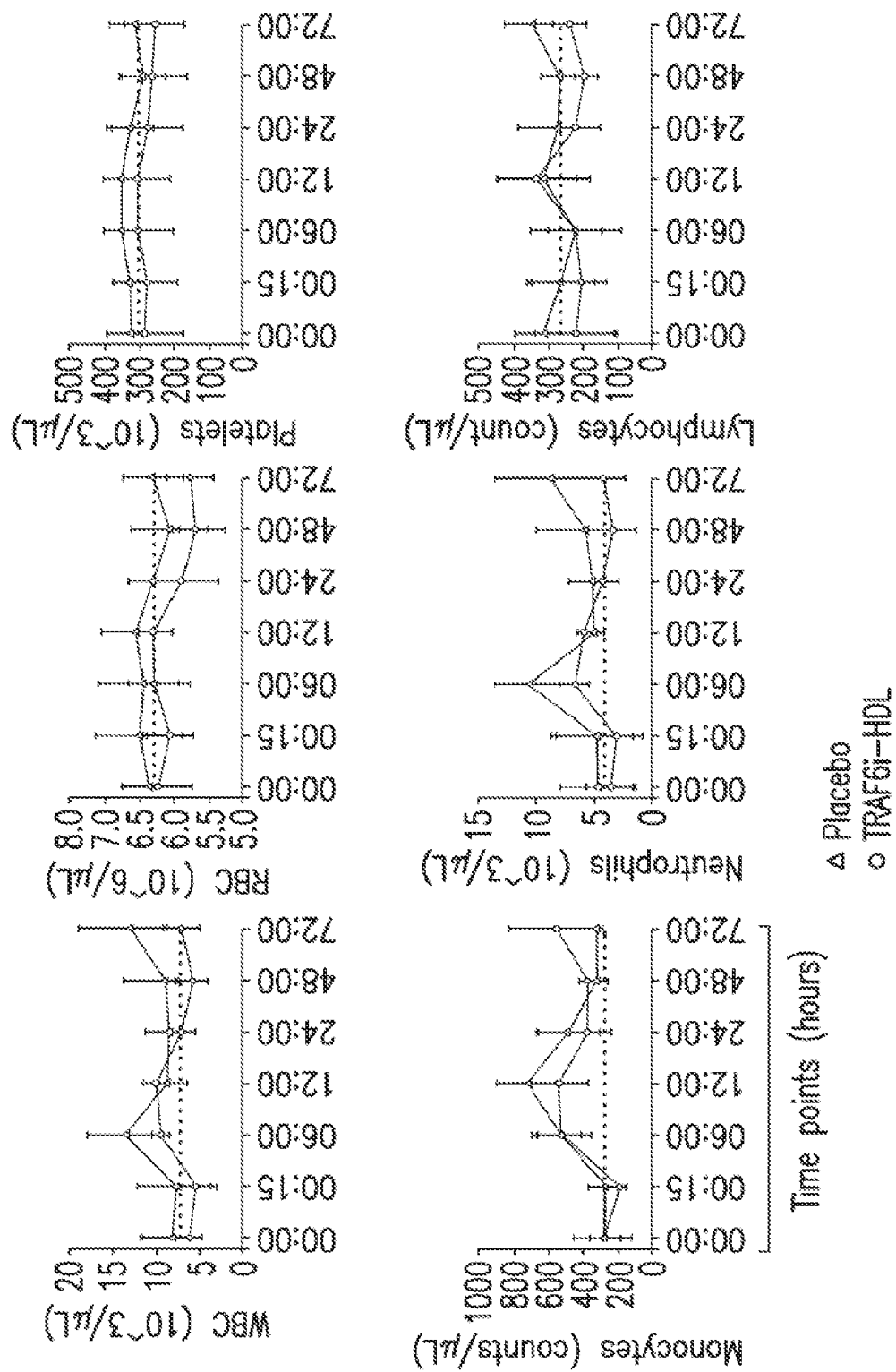
FIGS. 18A-C are graphs and images illustrating that TRAF6i-HDL therapy shows no toxic effects in non-human primates. Six non-human primates were infused with either placebo (n=3) or 1.25 mg/kg TRAF6i-HDL (n=3). Blood was collected at multiple time points and the animals were sacrificed 72 hours after infusion.
Figure 18B:
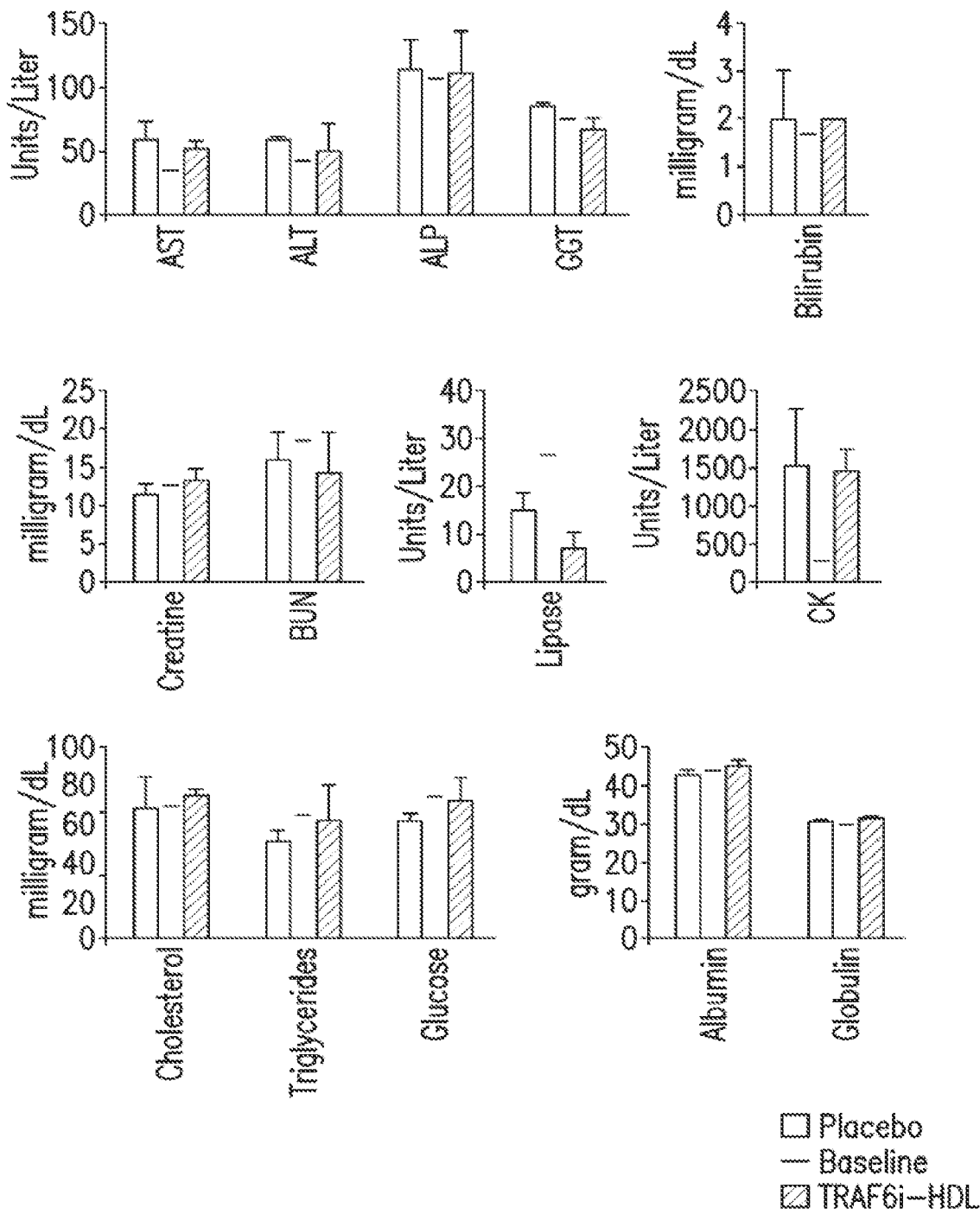
Figure 18C:
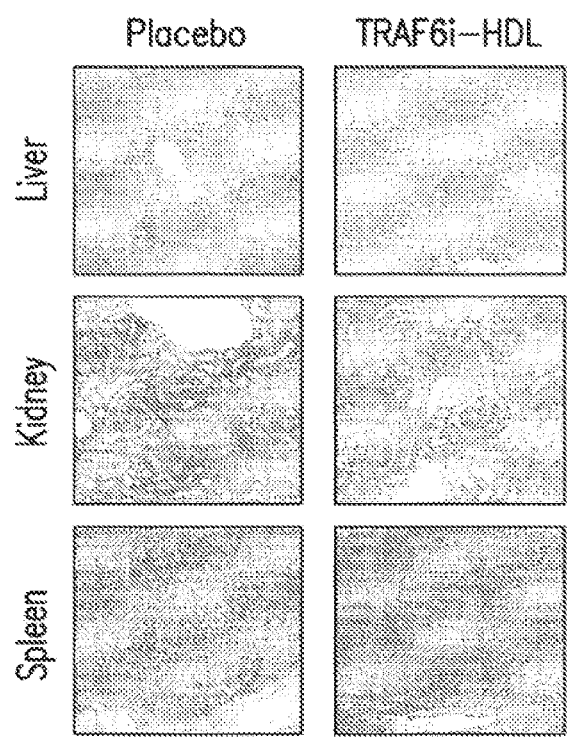

Complete blood count data from 7 time points within 72 hours after injection showed no differences between placebo and TRAF6i-HDL treated animals in white blood cells, monocytes, neutrophils, lymphocytes, red blood cells, platelets or any of the other indices, (FIG. 18A). Additionally, blood chemistry analysis showed no signs of hepatic, renal, pancreatic or muscle cell toxicity in the TRAF6i-HDL treated group as compared to the placebo group (FIG. 18B). Furthermore, lipid, glucose, and protein (albumin and globulin) levels were equal in both groups (FIG. 18B). Electrolytes were also unaffected. Specimens from liver, kidneys and spleen were sectioned and stained (H&E) for histology and evaluated by a pathologist. No signs of tissue damage or disturbances in tissue architecture were found (FIG. 18C).

Figure 19A:
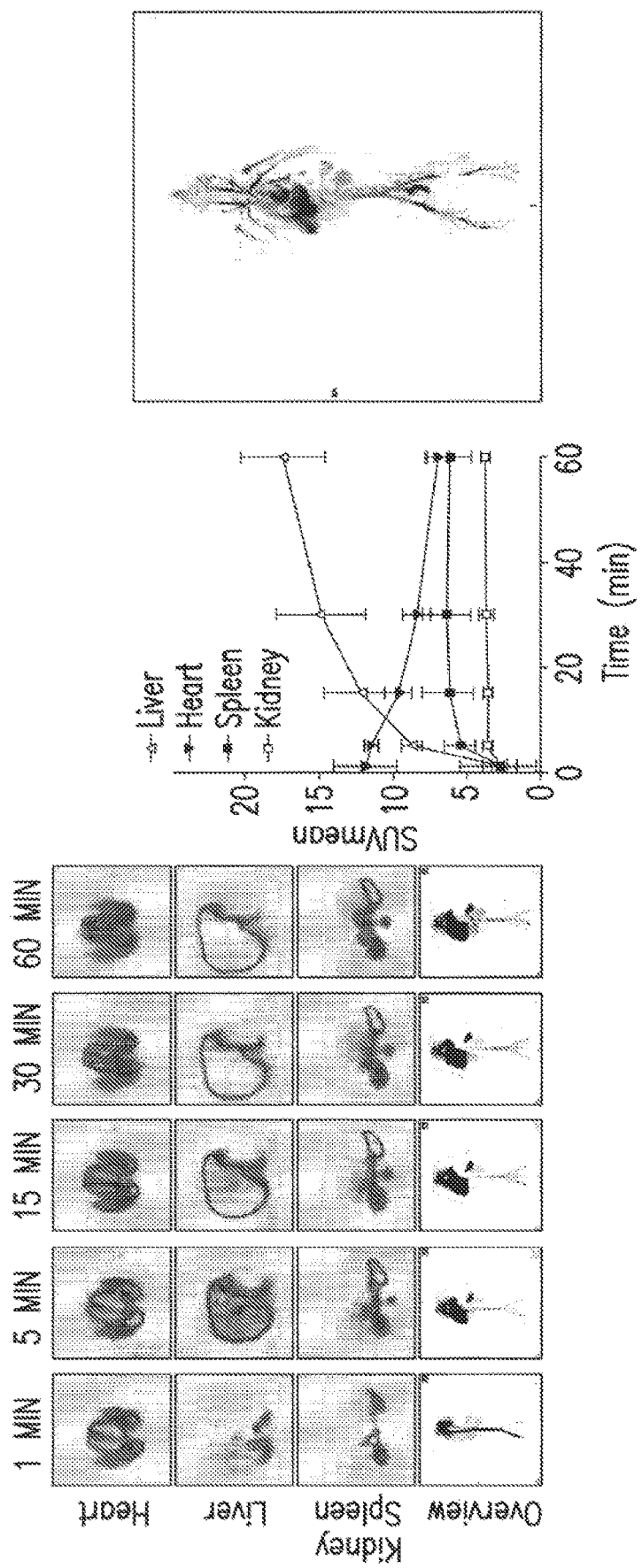
FIGS. 19A-D are images and graphs showing TRAF6i-HDL biodistribution in non-human primates. Six non-human primates were infused with either $^{89}$Zr-labeled TRAF6i-HDL (1.25 mg/kg). Dynamic PET images were acquired within 60 minutes after infusion. Static PET/MRI scans were performed at 24, 48 and 72 hours. NHP were sacrificed after 72 hours. Organs were collected for ex vivo analysis.
Figure 19B:
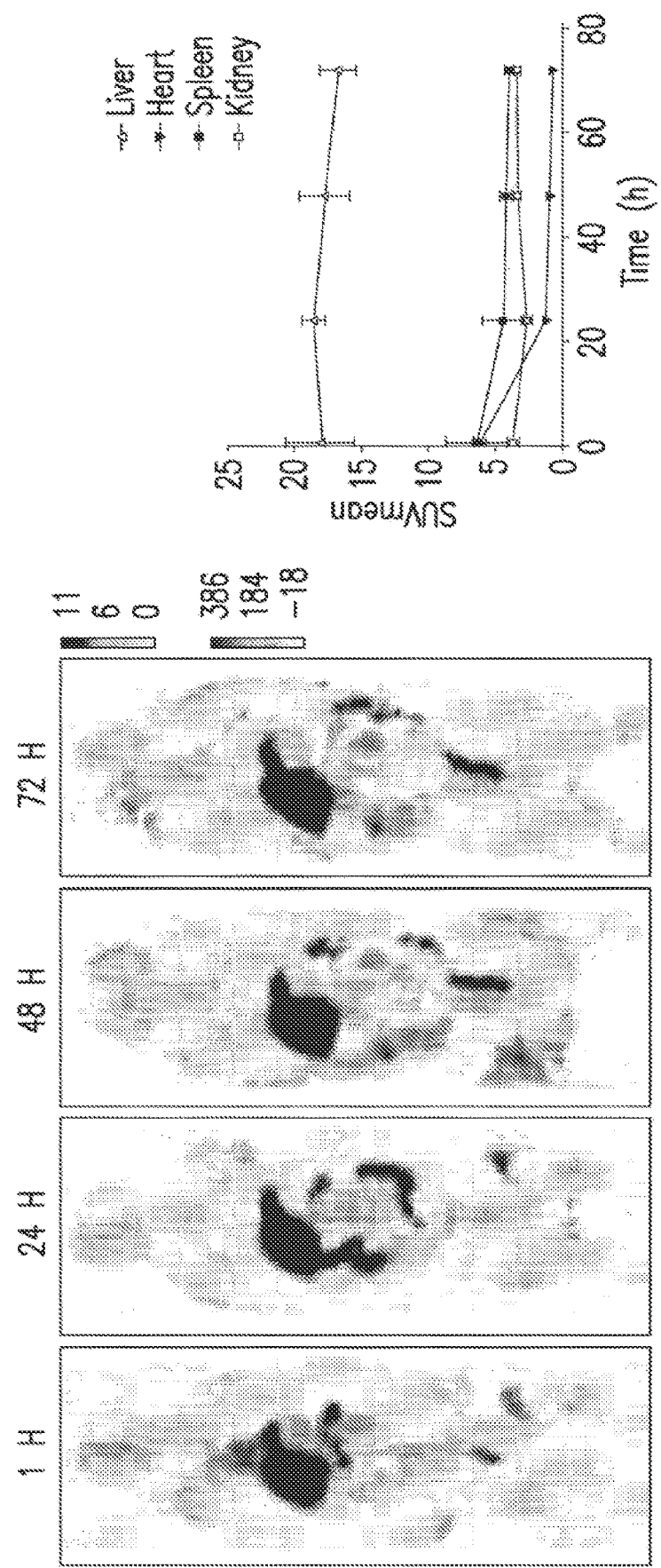
Figure 19C:
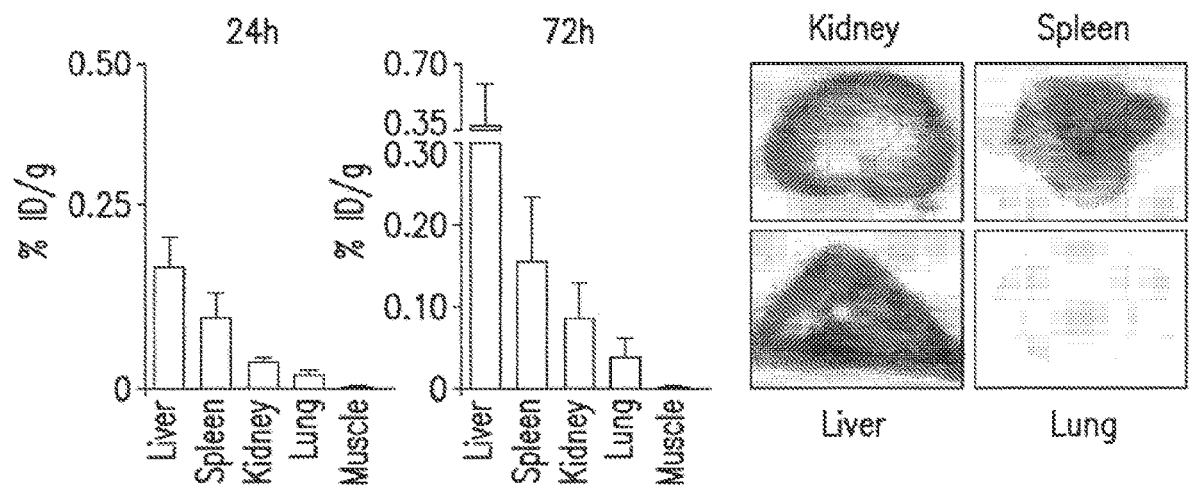
Figure 19D:
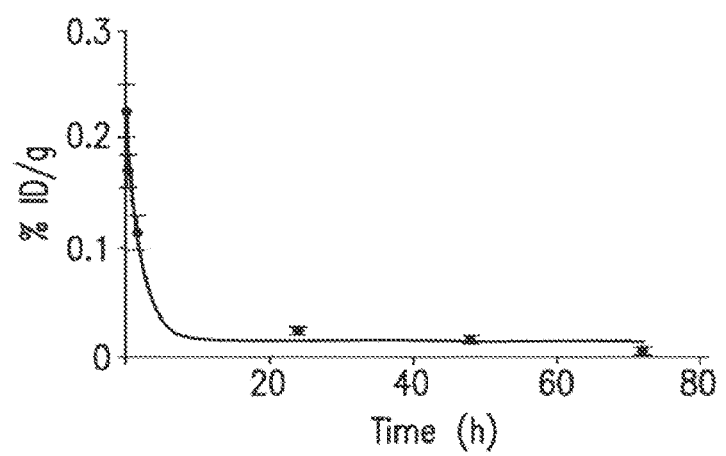

To assess biodistribution, six NHPs were subjected to full body PET/MR imaging after intravenous administration of 89Zr-labeled TRAF6i-HDL The animals were dynamically imaged over the course of the first hour post administration, while subsequent static scans were performed at 1, 24, 48 and 72 hours. Dynamic PET imaging showed rapid radioactivity accumulation in the liver, spleen and kidneys, followed by a significant uptake in the bone marrow (FIG. 19A). One hour post injection. PET images were dominated by the strong signal from the kidneys, followed by the liver and spleen at the 1 hour time point (FIG. 19A). At 24, 48 and 72 hours, radioactivity accumulated mostly in the liver and spleen (FIG. 19B). After sacrificing the animals at the 72 hour time point, tissue gamma counting showed that the largest amount of the injected dose (% ID/g) could be traced back to the liver and spleen, followed by the kidneys, which corroborates the findings of the PET/MRI imaging (FIG. 19C). Blood was collected at different time points and the data were fitted using a two-phase decay non-linear regression. The t½-fast was 14.2 min and the t½-slow was 513 min, resulting in a weighted blood half-life (t½) of 272 min (FIG. 19D).

Discussion

In the current study we describe the development of an HDL based nanoimmunotherapy targeted against the CD40-TRAF6 interaction in monocytes/macrophages. Our data show that TRAF6i-HDL accumulates in atherosclerotic lesions, and has a strong affinity for monocytes/macrophages. A single week of therapy rapidly reduces plaque macrophage content, which can in part be attributed to the inhibition of monocyte recruitment. The fact that TRAF6i-HDL proved to be safe in non-human primates illustrates the translational potential of this therapy.

The CD40-CD40L signaling axis has long been recognized to play an imperative role in eliciting immune responses in atherosclerosis [2-5]. While its identification gave rise to high anticipation, therapeutic targeting of this costimulatory receptor-ligand pair proved cumbersome. An anti-CD40L antibody was effective in diminishing atherosclerosis development in mice [3-5], but thromboembolic complications due to C140 expressed on platelets prohibited its application in humans [21, 22]. Furthermore. CD40 is expressed on B lymphocytes, and prolonged blocking would impair their maturation causing immunodeficiency [9]. In the current study, we addressed these issues by targeting TRAF6's interaction with the cytoplasmic domain of CD40 specifically in monocytes/macrophages. This was accomplished by using HDL as a nanoparticle carrier loaded with a small molecule inhibitor of CD40-TRAF6 interaction. These data show that our HDL based nanoparticles exposed over 80% of monocytes and macrophages to its cargo, while lymphocytes did not take up any nanoparticles.

In addition to restricting the delivery of CD40-TRAF6 inhibitor to the monocyte/macrophage population, we also aimed to minimize systemic immunosuppressive effects by using short duration of therapy of only a single week. Previous therapeutic studies targeting the CD40-CD40L signaling axis used prolonged treatment times [3-5]. The fact that we found a 49% and 66% decrease in plaque Ly6Chi monocyte and macrophage content within one week indicates the high potency of TRAF6i-HDL therapy. Of note, we proved the contribution of apoA-I to the therapeutic effect of TRAF6i-HDL to be minor. We used 4 infusions of 9 mg/kg apoA-1, which is relatively low compared to previously published studies [24], and we found no effects of empty HDL on plaque monocyte/macrophage content compared to placebo.

The mechanism by which TRAF6i-HDL decreased plaque inflammation on such a short timescale can in part be explained by decreased monocyte recruitment. In general, plaque macrophage content is determined by a balance of monocyte recruitment as well as macrophage proliferation, apoptosis and migratory egress. The first two processes are considered the most important determinants [25-28]. Our data did not reveal an effect on macrophage proliferation, apoptosis or migratory egress, while we did observe a decrease in plaque Ly6Chi monocyte content, suggestive of decreased monocyte recruitment. Moreover, we did not find a decrease in blood monocytes that could account for the decreased number of monocytes in the plaque. Previous studies showed high kinetics of monocytes [13, 14, 26-28], and decreased recruitment was shown to cause over 70% reduction in plaque macrophage content within 4 weeks [26]. Vice versa, a sudden increase in monocyte recruitment, induced by myocardial infarction, caused a marked increase in plaque macrophage content within 1-3 weeks [27]. These observations are in line with our findings of decreased monocyte recruitment causing a 66% decrease of plaque macrophage content within one week.

Our transcriptome analysis data support that monocyte recruitment is affected. The analyses did not show a clear role for chemokine receptors or ligands. However, the GO function analysis showed that "focal adhesion", a pivotal process in cell migration, was significantly enriched with DE genes. The KEGG pathway analysis also showed enrichment for "focal adhesion". Genes in the "focal adhesion" pathway of specific interest are Rhoa, Rap1b and Rap1b, which play a central role in the regulation of monocyte migration by activating integrins [16]. They were all significantly down regulated. This is in line with previous observations in a knockout mouse model with defective CD40-TRAF6 signaling, in which luminal adhesion of circulating monocytes to carotid arteries was impaired in vivo as assessed by intravital microscopy [7]. Also, the migratory capacity of macrophages was markedly affected [7].

The effects of TRAF6i-HDL are not limited to "focal adhesion", as attested by various other gene expressions that were shown to be affected. Together, the present data indicate that TRAF6i-HDL affects various biological processes in plaque monocytes/macrophages, including impairment of monocyte/macrophage migration. The extensive experiments on pharmacokinetics, biodistribution and safety in non-human primates (NHPs) illustrate the translatability of this treatment. The use of reconstituted HDL has previously proved to be safe in humans with apoA-I doses of 40 ng/kg [24]. Since we used 9 mg/kg apoA-1, this poses no safety issues. The small molecule inhibitor of CD40-TRAF6 interaction that was recently developed, has not been evaluated in humans to date. Biodistribution of $^{89}$Zr labeled TRAF6i-HDL was similar to previous observations with $^{89}$Zr labeled HDL in murine, rabbit, and porcine atherosclerosis models [29]. We observed the highest accumulation in the liver, spleen and kidneys. The liver and kidneys are the main sites of apoA-1 and HDL catabolism, and the spleen is the major secondary lymphoid organ containing many mycloid cells that clear the nanoparticles from the circulation. There were no signs of toxic effects in the liver, kidney or spleen and all tissues showed normal tissue architecture on histological analysis. Furthermore, complete blood count did not show any effects on the numbers of platelets, lymphocytes, monocytes, neutrophils or red blood cells. Safety data was assessed up until 72 post administration. Long term safety was not assessed in the current study.

Currently there are no specific therapies available that address plaque inflammation, although chronic therapy with an anti-interleukin-1β antibody and low dose methotrexate is currently being investigated in large Phase III clinical trials [30-32]. The challenge with immunosuppression in a chronic disease such as atherosclerosis is balancing the risk against the benefit. In contrast to the aforementioned strategy of chronic immunosuppression, we conceive that a short term induction nanotherapy with immune modulating properties can be used to rapidly suppress plaque inflammation in patients at high risk of cardiovascular events. While targeted delivery enhances the local efficacy of the drug, its short term application minimizes the risks associated with prolonged immunosuppression. Patients admitted for an acute coronary syndrome may be an appropriate population for such induction therapy of inflammation since they have a markedly increased risk of recurrent myocardial infarction of up to 17.4% within the first year [33]. Recent studies have proposed that it is the initial myocardial infarction itself that evokes monocyte recruitment to atherosclerotic plaques causing them to become inflamed and vulnerable for plaque rupture [27]. In this pathophysiological context, our concept of rapid suppression of monocyte recruitment in the vulnerable phase is expected to be relevant. This study provides an innovative therapeutic approach of a rapid induction therapy to treat inflammation in atherosclerosis, by targeting CD40-TRAF6 signaling in monocytes/macrophages. The infusible TRAF6i-HDL nanoimmunotherapy has promising potential for translation as attested by the favorable safety data in non-human primates.

In view of these results, it is expected that the TRAF6i-HDL nanoparticles will also be useful in conditions associated with or related to obesity and insulin resistance. Such conditions and complications include: insulin resistance, type 2 diabetes mellitus and cardiovascular disease. It is expected that blocking the CD40-TRAF pathway will lead to a lack of insulin resistance and a reduction in both adipose tissue (AT) inflammation and hepatosteatosis in diet-induced obesity, and similar conditions. It will further be expected that the TRAF6i-HDL nanoparticles of the present invention will be able to protect against AT inflammation and metabolic complications associated with obesity. Thus, administering the TRAF6i-HDL nanoparticles, alone or in combination with other standard of care treatments, may improve patient outcomes and prevent or reverse damage associated with these conditions.

Methods

Synthesis of rHDL Based Nanoparticles.

The synthesis of TRAF6i-HDL was based on a previously published method [34, 23]. In short, the CD40-TRAF6 inhibitor 6877002 [10] was combined with 1-myristoyl-2-hydroxyn-glycero-phosphocholine (MHPC) and 1,2-dimyristoyl-sn-glycero-3-phosphatidylcholine (DMPC) (Avanti Polar Lipids) in a chloroform/methanol mixture (9:1 by volume) and then dried in a vacuum, yielding a thin lipid film. A PBS solution of human apolipoprotein A1 (apoA-1) was added to the lipid film. The mixture was incubated on ice for 1 hour or until the film was hydrated and a homogenous solution was formed. The solution was then sonicated for 20 minutes to form TRAF6i-HDL nanoparticles. Subsequently, the solution was purified by multiple centrifugal filtration steps. For targeting, imaging and biodistribution experiments, analogs of TRAF6i-HDL were prepared through incorporation of the fluorescent dyes DiR or DiO (Invitrogen), or the phospholipid chelator DSPF-DFO (I mol % at the expense of DMPC, which allows radiolabeling with $^{89}Zr$ [35].

Animals and Diet for the Mouse Studies.

Female Apoe$^{-/-}$ mice (B6.129P2-Apoe$^{tm1Unc}$, n=103) were used for this study. All animal care and procedures were based on an approved institutional protocol from Icahn School of Medicine at Mount Sinai. Eight-week-old Apoe$^{-/-}$ mice were purchased from The Jackson Laboratory. All mice were fed a high-cholesterol diet (HCD) (0.2% weight cholesterol; 15.2% kcal protein, 42.7% kcal carbohydrate, 42.0% kcal fat; Harlan TD. 88137) for 12 weeks.

The treatment protocol in each experiment was identical: twenty-week-old Apoe$^{-/-}$ mice were randomly assigned to either placebo (saline), empty rHDL or TRAF6i-HDL (5 mg/kg) groups. Mice were treated with 4 intravenous injections over 7 days, while kept on a HCD during treatment. Animals were sacrificed 24 hours after the last injection.

Flow Cytometry.

Apoe$^{-/-}$ mice were euthanized and perfused with PBS, after which the aorta from the aortic root to the iliac bifurcation was gently cleaned from fat and collected. Whole aortas were put in an enzymatic digestion solution containing liberase TH (4 U/mL) (Roche), deoxyribonuclease (DNase) I (40 U/ml) (Sigma-Aldrich) and hyaluronidase (60 U/mL) (Sigma-Aldrich), minced and placed in a 37° C. incubator for 60 min. Cells were run through a 70 μm strainer, and twice spun down and resuspended in serum containing media. Spleens were weighed and pushed through a 70 μm cell-strainer, spun down, resuspended in red cell lysis buffer for 4 minutes, and then inactivated using serum containing media, spun down and resuspended in 1000 μL serum containing media per 100 mg of spleen tissue. EDTA treated blood was spun down, resuspended in red cell lysis buffer for 4 minutes, and then inactivated using serum containing media, spun down and resuspended in 100 μl of serum containing media. Bone marrow was obtained from a single femur. The intact femurs were rinsed with 70% ethanol followed by three subsequent washes in ice-cold sterile PBS. The epiphyses were cut off and the bone marrow was flushed out with PBS. Cells were run through a 70 μm strainer, spun down and resuspended in red cell lysis buffer for 30 seconds, and then inactivated using serum containing media, spun down and resuspended in 1000 pit, of serum containing media. The following antibodies were used: F4/80-PE-Cy7 (clone BM8, Biolegend); CD11b-PerCP/Cy5.5 (clone M1/70, BioLegend); CD11c-APC (clone N418. Biolegend); CD45-brilliant violet 510 (clone 30-F11, BioLegend); Ly-6C-PE (clone AL-21, BD Biosciences); Ly6CFITC (clone AL-2), BD Biosciences); CD90.2-eFluor 450 (clone 53-2.1. eBioscience); CD90.2-PE (clone 53-2.1. BD Biosciences); Ter119-eFluor 450 (clone TER-119. eBioscience); NK1.1-eFluor 450 (clone PK136, eBioscience); NK1.1-PE (clone PK136, BD Biosciences); CD49b-eFluor 450 (clone DX5, eBioscience); CD45R-eFluor450 (clone RA3-6B2, eBioscience): Ly-6G-Pacific Blue (clone 1A8, BioLegend); Ly-6G-PE (clone 1A8, BD Biosciences); CD3-PE (clone 17A2; Biolegend); CD19-PE (clone ID3. BD Bioscience).

The antibody dilutions ranged from 1:200 to 1:100. Contribution of newly made cells to different populations was determined by in vivo labeling with bromodeoxyuridine (BrdU). Incorporation was measured using APC-conjugated anti-BrdU antibodies according to the manufacturer's protocol (BD APC-BrdU Kit, 552598). Monocytes and macrophages were identified using a method similar to one described previously [28]. Specifically, Ly6C$^{hi}$ monocytes were identified as CD11b$^{low}$, CD11c$^{low}$, Lin$^{low}$ (with Un defined as CD90.2+, CD45R+, CD49b+. NK1.1+, Ly-6G+, Ter119+ or CD90.2+, NK1.1+, Ly-6G+, CD19+, CD3+) F4/80$^{low}$ that were also Ly-6C$^{hi}$. Macrophages were identified as CD11b$^{hi}$, CD11c$^{low}$, Lin$^{low}$, F4/80$^{hi}$, CD11$^{low}$. Data were acquired on an LSRII flow cytometer (BD Biosciences) and analyzed with FlowJo v10.0.7 (Tree Star, Inc.).

Histology and Immunohistochemistry.

Tissues for histological analysis were collected and fixed overnight in formalin and embedded in paraffin. Aortic roots were sectioned into 4 μm slices, generating a total of 90-100 cross-sections per root. Eight cross-sections were stained with hematoxylin and eosin (HE) and used for atherosclerotic plaque size measurement. Other sections were deparaffinized, blocked, incubated in 95° C. antigen-retrieval solution (DAKO), and immunolabeled with either MAC-3 rat monoclonal antibody (1:30; BD Biosciences) or anti-Ki67 rabbit polyclonal antibody (1:200, Abcam). Sirius red staining was used for analysis of collagen content. Antibody staining was visualized by either Impact AMEC red (Vectorlabs) or diaminobenzidine (DAB). Sections were analyzed using a Leica DM6000 microscope (Leica Microsystems) or the VENTANA iScan HT slide scanner (Ventana).

Laser Capture Microdissection and RNA Sequencing.

LCM was performed on 24 aortic root sections (6 μm) as previously described (20). In short, frozen sections were dehydrated in graded ethanol solutions (70% twice, 95% twice, 100% once), washed with DEPC treated water, stained with Mayer's hematoxylin, eosin and cleared in xylene. For every 8 sections, 1 section was used for CD68 staining (Abdserotec, 1:250 dilution) which was used to guide the LCM. CD68 rich areas within the plaques were identified and cut out using the ArcturusXT LCM System. The collected CD68 positive cells were used for RNA isolation (PicoPure RNA Isolation Kit, Arcturus) and subsequent RNA amplification and cDNA preparation according to the manufacturers protocols (Ovation Pico WTA System, NuGEN). Quality and concentration of the collected samples were measured with the Agilent 2100 Bioanalyzer.

RNA sequencing. Pair-end libraries were prepared and validated. The purity, fragment size, yield and concentration were determined. During cluster generation, the library molecules were hybridized onto an Illumina flow cell. Subsequently, the hybridized molecules were amplified using bridge amplification, resulting in a heterogeneous population of clusters. The data set was obtained using an Illumina HiSeq 2500 sequencer.

Differential Expression and Function Annotation Analysis.

The pair-ended sequencing reads were aligned to human genome hg19 using tophat aligner (bowtie2) [36]. Following read alignment. HTSeq [37] was used to quantify gene expression at the gene level based on GENCODE gene model release 22 [38]. Gene expression raw read counts were normalized as counts per million using trimmed mean of M-values normalization method to adjust for sequencing library size difference among samples [39]. Differential expressed genes between drug treatments and placebo were identified using the Bioconductor package limma [40]. In order to correct the multiple testing problem, limma was used to calculate statistics and p-values in random samples after a permutation of labels. This procedure was repeated 1,000 times to obtain null t-statistic and p-value distribution for estimating the false discovery rate (FDR) of all genes. The differentially expressed (DE genes were identified by a cutoff of corrected p-value less than 0.2. GO-function [41] was used to annotate the DE genes, and to find cellular components that significantly enriched with the DE genes. DE genes were also mapped to the Kyoto Encyclopedia of Genes and Genomes (KEGG) pathway with KEGG Mapper [42].

Fluorescence Molecular Tomography with CT.

Female Apoe$^{-/-}$ mice fed a high-fat diet for 12 weeks, were treated with either four TRAF6i- HDL infusions (5 mg/kg, n=7) or saline (n=8) over 7 days. Five nanomoles of pancathepsin protease sensor (ProSense 680, PerkinElmer, Cat no. NEV10003) was intravenously administered 24 hours prior to imaging. For the FMT/CT imaging, animals were placed in a custom-built imaging cartridge, which was equipped for isoflurane administration during imaging. Animals were first scanned with high-resolution computed tomography (CT; Inveon PET-CT, Siemens), with a continuous infusion of CT-contrast agent (isovue-370, Bracco Diagnostics) at a rate of 55 μl/min through a tail vein catheter. Animals were subsequently scanned with an FMT scanner (PerkinElmer) in the same cartridge. The CT X-ray source with an exposure time of 370-400 ms was operated at 80 kVp and 500 mA. Contrast-enhanced high-resolution CT images were used to localize the aortic root, which was used to guide the placement of the volume of interest for the quantitative FMT protease activity map. Image fusion relied on fiducial markers. Image fusion and analysis was performed with OsiriX v.6.5.2 (The Osirix Foundation, Geneva).

Radiolabeling of HDL Nanoparticles.

Ready-to-label HDL nanoparticles were prepared by including 1 mol % the phospholipidchelat or DSPE-DFO (35) in the formulation mix at the expense of DMPC. The DFO-containing nanoparticles were then labeled with Zirconium-89 ($^{89}$Zr) as previously described (35). Briefly, the nanoparticles were reacted with $^{89}$Zr-oxalate in phosphate buffered saline (PBS. pH 7.1) at 37° C. for 1 hour. Purification was carried out by centrifugal filtration using 10 kDa molecular weight cut-off filter tubes, and washing twice with fresh sterile PBS. The radiochemical yield was 90 t 4% (n=3) and radiochemical purity >97%, as determined by size exclusion chromatography.

Pharmacokinetics, Biodistribution and PET/CT Imaging Studies in Mice

Female Apoe$^{-/-}$ mice fed a high-fat diet for 12 weeks (n=4, 25.5±2.6 g body weight) were injected with $^{89}$Zr-TRAF6i-HDL nanoparticles (183±16 μCi, 5 mg TRAF6i-HDL/kg). At predetermined time points (2, 15 and 30 min, and 1, 4, 8 and 24 hours) blood samples were taken, weighed and measured for radioactivity content using a 2470 Wizard automatic gamma counter (Perkin Elmer). Data were convened to percentage of injected dose per gram tissue [% ID/g], plotted in a time-activity curve and fitted using a non-linear two phase decay regression in Prism GraphPad (GraphPad Software inc, USA). A weighted blood radioactivity half-life (t½) was finally calculated.

Twenty-four hours after injection, the animals were scanned on an Inveon PET/CT scanner (Siemens Healthcare Global) under isoflurane/oxygen gas mixture anesthesia (2% for induction, 1% for maintenance). The PET static scan recorded a minimum of 25 million coincident events and lasted 10 min. The energy and coincidence timing windows were 350-700 keV and 6 ns, respectively. Image data were normalized to correct for nonuniformity of response of the PET, dead-time count losses, positron branching ratio, and physical decay to the time of injection, but no attenuation, scatter, or partial-volume averaging correction was applied. The counting rates in the reconstructed images were converted to activity concentrations (% ID/g) by use of a system calibration factor derived from the imaging of a mouse-sized water-equivalent phantom containing $^{89}$Zr. Images were analyzed using ASIPro VMTM (Concorde Microsystems) and Inveon Research software (Siemens Healthcare Global). Quantification of activity concentration was done by averaging the maximum values in at least 5 ROIs drawn on adjacent slices of the tissue of interest. Whole body standard low magnification CT scans were performed with the X-ray tube setup at a voltage of 80 kV and current of 500 µA. The CT scan was acquired using 120 rotational steps for a total of 220 degrees yielding and estimated scan time of 120 s with an exposure of 145 ms per frame. Immediately after the PET/CT scan, animals were sacrificed and perfused with PBS. Tissues of interest (liver, kidneys, spleen, lungs, muscle, heart, aorta, bone and brain) were collected, blotted and weighed. Radioactivity was measured by gamma counting and radioactivity concentration expressed as percentage of injected dose per gram [% ID/g].

Autoradiography.

Following radioactivity counting, aortas were placed in a film cassette against a phosphorimaging plate (BASMS-2325, Fujifilm. Valhalla, NY) for 24 hours at −20° C. in order to determine radioactivity distribution. The plates were read at a pixel resolution of 25 µm with a Typhoon 7000IP plate reader (GE Healthcare, Pittsburgh. PA).

Ex Vivo Near Infrared Fluorescence Imaging (NIRF).

Female Apoe$^{-/-}$ mice fed a high-fat diet for 12 weeks, received a single IV injection with DiR (0.5 mg/kg) labeled TRAF6i-HDL (5 mg/kg, n=2) or saline (n=1). Mice were sacrificed 24 hours after the injection and perfused with 60 mL PBS. Liver, spleen, lung, kidneys, heart and muscle tissue were collected for NIRF imaging. Fluorescent images were acquired with the IVIS 200 system (Xenogen), with a 2 second exposure time, using a 745 nm excitation filter and a 820 nm emission filter. ROIs were drawn on each tissue with software provided by the vendor, after which a quantitative analysis was done with the average radiant efficiency within these ROIs.

Blood Tests.

In mice blood was collected by heart puncture at the time of sacrifice. Serum was sent to IDEXX laboratories (Totowa, New Jersey. USA) and analyzed with an Olympus AU400 chemistry analyzer. Whole blood was collected in EDTA containing tubes and analyzed with an IDEXX procyte DX hematology analyzer for complete blood count analysis. In non-human primates blood was collected at 0 and 15 minutes and 6, 12, 24, 28, 48 and 72 hours after infusion. Serum was analyzed with an Olympus AU400 chemistry analyzer. Whole blood samples were also analyzed with an IDEXX procyte DX hematology analyzer.

Non-Human Primate Studies

Adult male cynomolgus monkeys (*Macaca fascicularis*) were used for the non-human primate studies conducted at the University of Kentucky and Icahn School of Medicine at Mount Sinai. Animals were on average 7.3 years of age, and their weight was 7.3±1.98 kg (mean±SD). All animal care, procedures and experiments were based on approved institutional protocols from Icahn School of Medicine at Mount Sinai and the University of Kentucky Institutional Animal Care and Use Committee. Monkeys were pair-housed when possible in climate-controlled conditions with 12-hour light/dark cycles. Monkeys were provided water ad libitum and fed Teklad Global 20% Protein Primate Diet. For the experiment at the University of Kentucky, the six male monkeys were used. After an overnight fast, monkeys were anesthetized with ketamine (5 mg/kg) and dexmedetomidine (0.075-0.015 mg/kg), and blood was collected from the femoral vein. The monkeys were then injected IV via the saphenous vein with either vehicle (PBS, USP grade) or TRAF6i-HDL such that the dose of CD40-TRAF6 inhibitor 6877002 was 1.25 mg/kg. Blood was collected 15 minutes, 6, 12, 24, and 48 hours post-injection. Following the blood draw anesthesia was reversed with atipamezole (0.075-0.15 mg/kg). 72 hours postinjection, fasted monkeys were anesthetized with ketamine (25 mg/kg), bled a final time, and euthanized by exsanguination with whole-body saline perfusion while anesthetized with isoflurane (3-5% induction, 1-2% maintenance). Tissues were promptly removed and fixed in 10% neutral-buffered formalin. Blood was subjected to complete blood count (CBC) test (ANTECH Diagnostics).

For the experiment at Icahn School of Medicine at Mount Sinai six female monkeys were used. For the $^{89}$Zr-PET/MRI imaging, animals were infused with 58.9±17.9 MBq of $^{89}$Zr-labeled TRAF6i-HDL (1.25 mg/kg) and imaged by PET/MRI at different time points. Dynamic PET imaging was performed during the first 60 minutes after infusion. Additional PET/MRI scans were performed at 24, 48 and 72 hours. PET and MR images were acquired on a combined 3T PET/MRI system (Biograph mMR, Siemens Healthineers, Erlangen, Germany). On day 1, dynamic PET imaging was performed for 60 minutes using one bed position covering the chest and abdomen, directly after injection with $^{89}$Zr-labeled TRAF6i-HDL. Simultaneously, anatomical vessel wall MR images were acquired using a proton density (PD) weighted Sampling Perfection with Application optimized Contrasts using different flip angle Evolution (SPACE) sequence. MR imaging parameters were: acquisition plane, coronal; repetition time (TR), 1000 ms; echo time (TE), 79 ms; field of view (FOV), 300×187 mm2; number of slices, 144: number of averages, 4; bandwidth. 601 Hz/pixel; turbo factor (TF), 51; echo trains per slice, 4; echo train length, 192 ms; echo spacing, 3.7 ms; acquisition duration, 33 minutes and 36 seconds. After dynamic PET acquisition, static whole-body PET imaging was acquired from the cranium to the pelvis, using 3 consecutive bed positions, of 10 minutes each. Simultaneously with each bed, MR images were acquired as described above, except using only 1.4 signal average (acquisition duration, 11 min 44 seconds per bed). Whole-body PET and MR imaging was also performed at 24, 48 and 72 hours after injection, using 3 bed positions (PET duration per bed, 30 min; MR duration per bed, 33 min and 36 s). Whole-body MR images from each bed were automatically collated together by the scanner. After acquisition, PET raw data from each bed were reconstructed and collated together offline using the Siemens proprietary c7tools with an Ordered Subset Expectation Maximization (OSEM) algorithm with Point Spread Function (PSF) Correction. A dual-compartment (soft tissue and air) attenuation map was used for attenuation correction.

Statistical Analysis,

Continuous variables are expressed as means±standard deviation, unless otherwise stated. Significance of differences was calculated by use of the nonparametric Mann-Whitney U test and Kruskal-Wallis test. Probability values of P≤0.05 were considered significant. Statistical analyses were done using Statistical Package for the Social Sciences (SPSS) version 22.0.0.0.

REFERENCES

1. F. K. Swirski, M. Nahrendorf. Leukocyte behavior in atherosclerosis, myocardial infarction, and heart failure. *Science* 339, 161-166 (2013).
2. U. Schönbeck, P. Libby. CD40 signaling and plaque instability. *Circ Res.* 89, 1092-1103(2001).
3. E. Lutgens, L. Gorelik. M. J. Daemen, E. D. de Muinck, 1. S. Grewal. V. E. Koteliansky, R. A. Flavell, Requirement for CD154 in the progression of atherosclerosis. *Nat. Med.* 5, 1313-1316 (1999).
4. F. Mach, U. Schönheck, G. K. Sukhova, E. Atkinson, P. Libby, Reduction of atherosclerosis in mice by inhibition of CD40 signalling. *Nature* 394, 200-203 (1998).
5. U. Schönbeck, G. K. Sukhova, K. Shimizu, F. Mach. P. Libby. Inhibition of CD40 signaling limits evolution of established atherosclerosis in mice. *Proc. Natl. Acad. Sci. U.S.A.* 97, 7458-7463 (2000).
6. E. Lutgens, K. B. Cleutjens, S. Heeneman, V. E. Koteliansky. LC. Burkly. M. J. Daemen. Both early and delayed anti-CD40L antibody treatment induces a stable plaque phenotype. *Proc. Natl. Acad. Sc. U.S.A.* 97, 7464-7469 (2000).
7. E. Lutgens. D. Lievens, L. Beckers, E. Wijnands, O. Soehnlein, A. Zernecke, T. Seijkens, D. Engel, J. Cleutjens, A. M. Keller, S. H. Naik, L. Boon, H. A. Oufella, Z. Mallat, C. L. Ahonen, R. J. Noelle, M. P. de Winther, M. J. Daemen, E. A. Biessen, C. Weber, Deficient CD40-TRAF6 signaling in leukocytes prevents atherosclerosis by skewing the immune response toward an antiinflammatory profile. *J. Exp. Med.* 207, 391-404 (2010).
8. S. S. Pullen, H. G. Miller, D. S. Everdeen, T. T. Dang, J. J. Crute, M. R. Kehry, CD40-tumor necrosis factor receptor-associated factor (TRAF) interactions: regulation of CD40 signaling through multiple TRAF binding sites and TRAF hetero-oligomerization. *Biochemistry* 37, 11836-11845 (1998).
9. C. Ahonen, E. Manning, L. D. Erickson. B. O'Connor, E. F. Lind, S. S. Pullen, M. R. Kehry, R. J. Noelle, The CD40-TRAF6 axis controls affinity maturation and the generation of long-lived plasma cells. *Nat. Immunol.* 3, 451-456 (2002).
10. B. Zarzycka, T. Seijkens, S. B. Nabuurs, T. Ritschel, J. Grommes, O. Soehnlein, R. Schrijver, C. M. van Tiel, T. M. Hackeng, C. Weber, F. Giehler, A. Kieser, E. Lutgens, G. Vriend, G. A. Nicolaes, Discovery of small molecule CD40-TRAF6 inhibitors. *J. Chem. Inf Model.* 55, 294-307 (2015).
11. A. Chatzigeorgiou, T. Seijkens, B. Zarzycka. D. Engel. M. Poggi. S. van den Berg, S. van den Berg, O. Soehnlein, H. Winkels, L. Beckers, D. Lievens, A. Driessen, P. Kusters, E. Biessen, R. Garcia-Martin, A. Klotzsche-von Ameln, M. Gijbels. R. Noelle, L. Boon, T. Hackeng, K. M. Schulte, A. Xu, G. Vriend, S. Nabuurs, K. J, Chung. K. Willems van Dijk, P. C. Rensen. N. Gerdes. M. de Winther, N. L. Block, A. V. Schally, C. Weber, S. R. Bornstein, G. Nicolaes, T. Chavakis, E. Lutgens, Blocking CD40-TRAF6 signaling is a therapeutic target in obesity-associated insulin resistance. *Proc. Natl. Acad. Sci. U.S.A.* 111, 2686-2691 (2014).
12. C. S. Robbins, I. Hilgendorf, G. F. Weber, I. Theurl, Y. Iwamoto, J. L. Figueiredo, R. Gorbatov, G. K. Sukhova, L. M. Gerhardt, D. Smyth, C. C. Zavitz, E. A. Shikatani, M. Parsons, N. van Rooijen, H. Y. Lin, M. Husain, P. Libby, M. Nahrendorf, R. Weissleder, F. K. Swirski, Local proliferation dominates lesional macrophage accumulation in atherosclerosis. *Nat. Med.* 19, 1166-1172 (2013).
13. F. K. Swirski. P. Libby. E. Aikawa, P. Alcaide, F. W. Luscinskas, R. Weissleder, M. J. Pittet. Ly-6Chi monocytes dominate hypercholesterolemia-associated monocytosis and give rise to macrophages in atheromasia. *J Clin Invest.* 117, 195-205 (2007).
14. F. K S. wirski, M. J. Pittet. M. F. Kircher, E. Aikawa, F. A. Jatter, P. Libby, R. Weissleder. Monocyte accumulation in mouse atherogenesis is progressive and proportional to extent of disease. *Proc Ned Acad Sci USA.* 103, 10340-10345 (2006).
15. S. B. Iloki Assanga, A A. Gil-Salido, L. M. Lewis Luján. A. Rosas-Durazo, A. L. Acosta-Silva, E. G. Rivera-Castaneda, J. L. Rubio-Pino, Cell growth curves for different cell lines and their relationship with biological activities. *Int. J. Biotechnol. Mol Biol. Res.* 4.60-70 (2013).
16. B. A. Imhof, M. Aurrand-Lions. Adhesion mechanisms regulating the migration of monocytes. *Nat. Rev. Immunol.* 4, 432-444 (2004).
17. D. T. Valenta, J. J. Bulgrien, D. J. Bonnet, L. K. Curtiss, Macrophage PLTP is atheroprotective in LDLr-deficient mice with systemic PLTP deficiency. *J. Lipid. Res.* 49, 24-32 (2008).
18. G. D. Wenger, M. S. O'Dorisio, Induction of cAMP-dependent protein kinase I during human monocyte differentiation. *J. Immunol.* 134, 1836-1843 (1985).
19. G. Chinetti-Gbaguidi, S. Colin, B. Staels, Macrophage subsets in atherosclerosis. *Nat. Rev. Cardiol.* 12, 10-17 (2015).
20. Y. W. Huang. M. Yan, R. F. Collins. J. E. Diciccio. S. Grinstein, W. S. Trimble, Mammalian septins are required for phagosome formation. *Mol. Biol. Cell.* 19, 1717-1726 (2008).
21. T. Kawai, D. Andrews, R. B. Colvin, D. H. Sachs A. B. Cosimi, Thromboembolic complications after treatment with monoclonal anti-body against CD40 ligand. *Nat. Med.* 6, 114 (2000).
22. P. André, K. S. Prasad, C. V. Denis, M. He, J. M. Papalia. R. O. Hynes, D. R. Phillips, D. D. Wagner, CD40L stabilizes arterial thrombibyabeta3 integrin-dependent mechanism. *Nat. Med.* 8, 247-252 (2002).
23. R. Duivenvoorden, J. Tang, D. P. Cormode. A. J. Mieszawska. D. Izquierdo-Garcia, C. Ozcan. M. J. Otten, N. Zaidi, M. E. Lobatto, S. M. van Rijs, B. Priem, E. L. Kuan, C. Martel, B. Hewing, M. Sager, M. Nahrendorf, G. J. Randolph, E. S. Stroes, V. Fuster, E. A. Fisher, Z. A. Fayad, W. J. Mulder, A statin-loaded reconstituted high-density lipoprotein nanoparticle inhibits atherosclerotic plaque inflammation. *Nat. Commun.* 5, 3065 (2014).
24. P. K. Shah, J. Nilsson, S. Kaul, M. C. Fishbein, H. Ageland, A. Hamsten, J. Johansson, F. Karpe, B. Cercek. Effects of recombinant apolipoprotein A-1(Milano) on aortic atherosclerosis in apolipoprotein E-deficient mice. Circulation 97, 780-785 (1998).
25. K. J. Moore, F. J. Sheedy. E. A. Fisher, Macrophages in atherosclerosis: a dynamic balance. *Nat. Rev. Immunol.* 13, 709-721 (2013).
26. S. Potteaux, E. L. Gautier. S. B. Hutchison. N. van Rooijen, D. J. Rader. M. J. Thomas, M. G. Sorci-Thomas, G. J. Randolph, Suppressed monocyte recruitment drives macrophage removal from atherosclerotic plaques of $Apoe^{-/-}$ mice during disease regression. *J. Clin. Invest.* 121, 2025-2036 (2011).
27. P. Dutta, G. Courties, Y. Wei, F. Leuschner, R. Gorbatov, C. S. Robbins, Y. Iwamoto, B. Thompson, A. L. Carlson, T. Heidt, M. D. Majmudar, F. Lasitschka, M. Etzrodt, P. Waterman, M. T. Waring, A. T. Chicoine, A. M. van der Laan, H. W. Niessen, J. J. Pick, B. B. Rubin, J. Butany, J. R. Stone, H. A. Katus, S. A. Murphy, D. A. Morrow, M. S. Sabatine, C. Vinegoni, M. A. Moskowitz, M. J. Pittet, P. Libby, C. P. Lin, F. K. Swirski, R. Weissleder, M. Nahrendorf, Myocardial infarction accelerates atherosclerosis. *Nature* 487, 325-329 (2012).

28. C. S. Robbins, I. Hilgendorf, G. F. Weber, I. Theurl, Y. Iwamoto, J. L. Figueiredo, R. Gorbatov, G. K. Sukhova, L. M. Gerhardt, D. Smyth, C. C. Zavitz, E. A. Shikatani, M. Parsons, N. van Rooijen, H. Y. Lin, M. Husain, P. Libby, M. Nahrendorf, R. Weissleder, F. K. Swirski. Local proliferation dominates lesional macrophage accumulation in atherosclerosis. *Nat Med.* 19, 1166-1172 (2013).

29. C. Pérez-Medina, T. Binderup, M. E. Lobatto, J. Tang, C. Calcagno, L. Giesen, C. H. Wessel, J. Witjes, S. Ishino, S. Baxter, Y. Zhao, S. Ramachandran, M. Eldib, B. L. Sánchez-Gaytán, P. M. Robson, J. Bini. J. F. Granada, K. M. Fish, E. S. Stroes. R. Duivenvoorden, S. Tsimikas, J. S. Lewis, T. Reiner, V. Fuster, A. Kjaer, E. A. Fisher, Z. A. Fayad, W. J. Mulder, In Vivo PET Imaging of HDL in Multiple Atherosclerosis Models. *JACC. Cardiovasc. Imaging.* 9, 950-961 (2016).

30. P. M. Ridker, T. Thuren, A. Zalewski, P. Libby, Interleukin-1β inhibition and the prevention of recurrent cardiovascular events: rationale and design of the Canakinumab Anti-inflammatory Thrombosis Outcomes Study (CANTOS). *Am. Heart. J.* 162, 597-605 (2011).

31. B. M. Everett, A. D. Pradhan, D. H. Solomon, N. Paynter, J. Macfadyen, E. Zaharris, M. Gupta, M. Clearfield, P. Libby, A. A. Hasan, R. J. Glynn, P. M. Ridker, Rationale and design of the Cardiovascular Inflammation Reduction Trial: a test of the inflammatory hypothesis of atherothrombosis. *Am Heart J.* 166, 199-207 (2013).

32. M. Bäck. G. K. Hansson, Anti-inflammatory therapies for atherosclerosis. *Nat Rev Cardiol.* 12, 199-211 (2015).

33. G. W. Stone. A. Maehara, A. J. Lansky, B. de Bruyne, E. Cristea, G. S. Mintz, R. Mehran, J. McPherson, N. Farhat, S. P. Marso, H. Parise, B. Templin, R. White. Z. Zhang, P. W. Serruys. A prospective natural-history study of coronary atherosclerosis. *N. Engl. J. Med.* 364, 226-235 (2011).

34. Jonas A. Reconstitution of high-density lipoproteins. *Methods Enzymol* 128, 553-582 (1986).

35. C. Pérez-Medina, J. Tang, D. Abdel-Atti. B. Hogstad. M. Merad, E. A. Fisher, Z. A. Fayad, J. S. Lewis, W. J. Mulder, T. Reiner, PET Imaging of Tumor-Associated Macrophages with 89Zr-Labeled High-Density Lipoprotein Nanoparticles. *J. Nucl. Med.* 56, 1272-1277 (2015).

36. B. Langmead. S. L. Salzberg. Fast gapped-read alignment with Bowtie 2. *Nat Methods* 9, 357-359 (2012).

37. S. Anders, P. T. Pyl. W. Huber. HTSeq—a Python framework to work with high throughput sequencing data. *Bioinformatics* 31, 166-169 (2015).

38. J. M. Mudge, J. Harrow. Creating reference gene annotation for the mouse C57BL6/J genome assembly. *Mamm Genome.* 26, 366-378 (2015).

39. M. E. Ritchie, B. Phipson, D. Wu, Y. Hu. C. W. Law, SW. Shi. G. K. Smyth. Limma powers diffential expression analyses for RNA-sequencing and microarray studies. *Nucleic. Acids. Res.* 43. e47 (2015).

40. J. Wang, X. Zhou, J. Zhu. Y. Gu, W. Zhao, J. Zou, Z. Guo. GO-function: deriving biologically relevant functions from statistically significant functions. *Brief Bioinform* 13,216-227 (2012).

41. M. Kanehisa, S. Goto, Y. Sato, M. Furumichi, M. Tanabe. KEGG for integration and interpretation of large-scale molecular data sets. *Nucleic Acids Res.* 40, D109-114 (2012).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. A method for reducing tissue rejection in a patient in need thereof, the method comprising administering to the patient an effective amount of a composition comprising a high-density lipoprotein (HDL)-derived nanoparticle which comprises an mTOR inhibitor selected from rapamycin or an ester or prodrug thereof, a phospholipid, and an apolipoprotein A-I (apoA-I), wherein the patient has received an allogeneic tissue transplant, and wherein the composition is administered intravenously.

2. The method of claim 1, wherein the phospholipid is a phosphatidylcholine, a phosphatidylethanolamine, a phosphatidylinositol, a phosphatidylserine, or a ceramide.

3. The method of claim 1, wherein the phospholipid is dimyristoylphosphatidylcholine (DMPC), soy lecithin, dipalmitoylphosphatidylcholine (DPPC), distearoylphosphatidylcholine (DSPC), dilaurylolyphosphatidylcholine (DLPC), dioleoylphosphatidylcholine (DOPC), dilaurylolylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), dimyristoyl phosphatidic acid (DMPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), dipalmitoyl sphingomyelin (DPSP), distearoyl sphingomyelin (DSSP), and mixtures thereof.

4. The method of claim 1, wherein the HDL-derived nanoparticle comprises 1,2-(dimyristoyl-sn-glycero-3-phosphocholine (DMPC) and 1-myristoyl-2-hydroxy-sn-glycero-3-phosphocholine (MHPC).

5. The method of claim 1, wherein the mTOR inhibitor is rapamycin.

6. The method of claim 1, wherein the mTOR inhibitor is a prodrug of rapamycin.

7. The method of claim 1, wherein the mTOR inhibitor is an ester of rapamycin.

8. The method of claim 1, wherein the HDL-derived nanoparticle comprises cholesterol.

9. The method of claim 4, wherein the apoA-I is human apoA-I.

10. The method of claim 4, wherein the weight ratio of DMPC:MHPC is about 2:1 to about 4:1.

11. The method of claim 10, wherein the weight ratio of DMPC:MHPC is about 3:1.

12. The method of claim 1, wherein the HDL-derived nanoparticle is discoidal in shape and has a size from about 10 nm to about 250 nm.

13. The method of claim 1, wherein the transplanted tissue is lung tissue, heart tissue, kidney tissue, liver tissue, retinal tissue, corneal tissue, skin tissue, pancreatic tissue, intestinal tissue, genital tissue, ovary tissue, bone tissue, tendon tissue, bone marrow, or vascular tissue.

14. The method of claim 13, wherein the transplanted tissue is an intact organ.

15. The method of claim 1, further comprising administering to the patient one or more immunosuppressant agents.

16. The method of claim 15, wherein the immunosuppressant agent is cyclosporine A or FK506.

17. The method of claim 1, wherein the subject is human.

18. A method for the prophylaxis of tissue rejection in a patient in need thereof, the method comprising administering to the patient an effective amount of a composition comprising a high-density lipoprotein (HDL)-derived nanoparticle which comprises an mTOR inhibitor selected from rapamycin or an ester or prodrug thereof, a phospholipid, and an apolipoprotein A-I (apoA-I)), and wherein the composition is administered intravenously.

* * * * *